US008137509B2

(12) United States Patent
Porco, Jr. et al.

(10) Patent No.: US 8,137,509 B2
(45) Date of Patent: Mar. 20, 2012

(54) ASYMMETRIC SYNTHESIS OF ROCAGLAMIDES VIA ENANTIOSELECTIVE PHOTOCYCLOADDITION MEDIATED BY CHIRAL BRøNSTED ACIDS

(75) Inventors: John A. Porco, Jr., Brookline, MA (US); Baudouin Gerard, Cambridge, MA (US)

(73) Assignee: Trustees of Boston University, Boston, MA (US)

( * ) Notice: Subject to any disclaimer, the term of this patent is extended or adjusted under 35 U.S.C. 154(b) by 536 days.

(21) Appl. No.: 12/301,727

(22) PCT Filed: May 21, 2007

(86) PCT No.: PCT/US2007/012062
§ 371 (c)(1),
(2), (4) Date: Jul. 23, 2009

(87) PCT Pub. No.: WO2007/139749
PCT Pub. Date: Dec. 6, 2007

(65) Prior Publication Data
US 2009/0299081 A1    Dec. 3, 2009

Related U.S. Application Data

(60) Provisional application No. 60/802,560, filed on May 22, 2006.

(51) Int. Cl.
*C07D 307/93* (2006.01)
*C07D 311/94* (2006.01)
(52) U.S. Cl. ............... 204/157.69; 204/157.71; 548/425; 549/386; 549/458
(58) Field of Classification Search ............. 204/157.69, 204/157.71; 548/425; 549/386, 458
See application file for complete search history.

(56) References Cited

U.S. PATENT DOCUMENTS

| 5,169,943 | A | 12/1992 | Lubineau et al. |
| 6,099,751 | A | 8/2000 | Meyer et al. |
| 2008/0177093 | A1 | 7/2008 | Jones et al. |
| 2009/0299081 | A1 | 12/2009 | Porco |

FOREIGN PATENT DOCUMENTS

| WO | WO-2005/092876 | 10/2005 |
| WO | WO 2007/139749 | 12/2007 |

OTHER PUBLICATIONS

Bacher et al., "Thapsakins: possible biogenetic intermediates towards insecticidal cyclopenta[b]benzofurans from *Aglaia edulis*", *Phytochemistry*, 52:253-263 (1999).
Baer, "Oxidative Cleavage of α-Keto Acids and α-Keto Alcohols by Means of Lead Tetra-acetate", *J. Chem. Soc.*, 62:1597-1606 (1940).
Baldwin et al., "Expedient synthesis of a highly substituted tropolone via a 3-oxidopyrylium [5+2] cycloaddition reaction", *Tetrahedron Lett.*, 44:4543-4545 (2003).
Baumann et al., "Inducible Expression and Phosphorylation of Coactivator BOB.1/OBF.1 in T Cells", *J. Biol. Chem.*, 277:44791-44800 (2002).
Bohnenstengel et al., "Structure activity relationships of antiproliferative rocaglamide derivatives from *Aglaia* species (*Meliaceae*)", *Z. Naturforsch*. [C], 54: 55-60 (1999).
Bohnenstengel et al., "1H-cyclopenta[b]benzofuran lignans from *Aglaia* species inhibit cell proliferation and alter cell cycle distribution in human monocytic leukemia cell lines", *Z. Naturforsch*. [C], 54: 1075-1083 (1999).
Chou, "The host/guest type of excited-state proton transfer: a general review", *J. Chin. Chem. Soc.*, 48: 651-682 (2001).
Grout and Rathbone, "Catalysis Di-n-butyltin Oxide of a Tertiary Ketol Rearrangement: Synthesis of Intermediates and Analogues of Valine and Isoleucine Biosynthesis", *J. Chem. Soc. Chem. Commun.*, 290-291 (1987).
Creary et al., "Diels-Alder approach to bicyclic .alpha.-hydroxy ketones. Facile ketol rearrangements of strained .alpha.-hydroxy ketones", *J. Org. Chem.*, 50: 1932-1938 (1985).
Fahrig et al., "A Synthetic Derivative of the Natural Product Rocaglaol Is a Potent Inhibitor of Cytokine-Mediated Signaling and Shows Neuroprotective Activity in Vitro and in Animal Models of Parkinson's Disease and Traumatic Brain Injury", *Mol. Pharmacol.*, 67: 1544-1555 (2005).
Hausott et al., "Flavaglines: A group of efficient growth inhibitors block cell cycle progression and induce apoptosis in colorectal cancer cells", *Int. J. Cancer*, 109: 933-940 (2004).
Hendrickson and Farina, "A new 7-ring cycloaddition reaction", *J. Org.Chem.*, 45: 3359-3361 (1980).
Hwang et al., "Silvestrol and Episilvestrol, Potential Anticancer Rocaglate Derivatives from *Aglaia silvestris*", *J. Org. Chem.*, 69: 3350-3358 (2004).
Itoh, "Fluorescence studies of the excited-state proton transfer in substituted 3-hydroxychromones in supersonic jet", *Pure and Applied Chemistry*, 65: 1629-1634 (1993).
Ishibashi et al., "Insecticidal 1H-Cyclopentatetrahydro[b]Benzofurans from *Aglaia odorata*", *Phytochemistry*, 32: 307-310 (1993).

(Continued)

*Primary Examiner* — Bernard Dentz
(74) *Attorney, Agent, or Firm* — Brenda Herschbach Jarrell; Charles E. Lyon; Choate, Hall & Stewart LLP

(57) ABSTRACT

The present invention provides a new strategies for the synthesis of compounds of the rocaglamide family and related natural products. The synthetic approach generally involves photochemical generation of an oxidopyrylium species from a 3-hydroxychromone derivative followed by an enantioselective 1,3-dipolar cycloaddition of the oxidopyrylium species to a dipolarophile in the presence of a TADDOL derivative. This approach can be used for the formation of adducts containing an aglain core structure. Methods of the conversion of aglain core structures to aglain, rocaglamide and forbaglin ring systems are also provided. The present invention also relates to the use of rocaglamide/aglain/forbaglin derivatives for the manufacture of medicaments for use in the treatment of cancer or cancerous conditions, disorders associated with cellular hyperproliferation, or NF-κB-dependent conditions.

40 Claims, 19 Drawing Sheets

OTHER PUBLICATIONS

Kasha, "Proton-transfer spectroscopy. Perturbation of the tautomerization potential", *J. Chem. Soc. Faraday Trans.* 2, 82: 2379-2392 (1986).

King et al., "X-Ray Crystal Structure of Rocaglamide, a Novel Antileukemic 1H-Cyclopenta[b]benzofuran from *Aglaia elliptifolia*", *J. Chem. Soc., Chem. Commun.*, 1150-1151 (1982).

Klymchenko et al., "3-Hydroxychromone dyes exhibiting excited-state intramolecular proton transfer in water with efficient two-band fluorescence", *New J. Chem.*, 28: 687-692 (2004).

Klymchenko, "Elimination of hydrogen bonding effect on solvatochromism of 3-hydroxyflavones", *J. Phys. Chem. A*, 107: 4211-4216 (2003).

Kraus and Sy, "A synthetic approach to rocaglamide via reductive cyclization of .delta.-keto nitriles", *J. Org. Chem.*, 54: 77-83 (1989).

Kumar et al., "Intramolecular excited-state proton-transfer studies on flavones in different environments", *Spectrochim. Acta, Part A*, 57: 299-308 (2001).

Laermer et al., "Femtosecond spectroscopy of excited-state proton transfer in 2-(2'-hydroxyphenyl)benzothiazole", *Chem. Phys. Lett.*, 148:119-124 (1988).

Lee et al., "Cytostatic mechanism and antitumor potential of novel 1H-cyclopenta[b]benzofuran lignans isolated from *Aglaia elliptica*", *Chem. Biol. Interact.*, 115:215-228 (1998).

Leeand Wu, "Total Synthesis of Kaempferol and Methylated Kaempferol Derivatives", *J. Chin. Chem. Soc.*, 48: 201-206 (2001).

Mandal et al., "Evidence of ground-state proton-transfer reaction of 3-hydroxyflavone in neutral alcoholic solvents", *J. Phys. Chem. A*, 107: 6334-6339 (2003).

Matsuura and Takemo, "Photoinduced reactions. 61. Photorearrangement of 3-hydroxyflavones to 3-aryl-3-hydroxy-1,2-indandiones", *Tetrahedron*, 3337-3340 (1973).

Ohse et al., "Cyclopentabenzofuran Lignan Protein Synthesis Inhibitors from *Aglaia odorata*", *J. Nat. Prod.*, 650-652 (1996).

Paquette and Hofferberth, "Effect of 9,10-cyclic acetal sterochemistry on feasible operation of the alpha-ketol rearrangement in highly functionalized paclitaxel (Taxol) precursors", *J. Org. Chem.*, 68: 2266-2275 (2003).

Piers et al., "Sequential anionic 1,3-ester shifts and intramolecular stille couplings: a new protocol for the concise assembly of functionalized polycyclic dienes", *Synlett.*, 7: 1082-1084 (1999).

Sammes et al., "The preparation and some reactions of 3-oxidopyrylium", *J. Chem. Soc. Perkin Trans. I*, 1261-1265 (1983).

Schwartz et al., "Direct observation of fast proton transfer: femtosecond photophysics of 3-hydroxyflavone", *J. Phys. Chem.*, 96: 3591-3598 (1992).

Shipman et al., "Synthesis of 1,3,2-dioxathiolane-4-methylene-2-oxides: Potential allene oxide equivalents", *Tetrahedron*, 55: 10845-10850 (1999).

Tamaki et al., "Syntheses of (−)-(7S)- and (+)-(7R)-K252a dimers", *Tetrahedron Lett.*, 43: 379-382 (2002).

Tanaka et al., "Synthesis of flavonol derivatives as probes of biological processes", *Tetrahedron Lett.*, 41: 9735-9739 (2000).

Trost et al., "An unusual oxidative cyclization. A synthesis and absolute stereochemical assignment of (−)-rocaglamide", *J. Am. Chem. Soc.*, 112: 9022-9024 (1990).

Wender et al., "The First Synthesis of a Daphnane Diterpene: The Enantiocontrolled Total Synthesis of (+)-Resiniferatoxin", *J. Am. Chem. Soc.*, 119: 12976-12977 (1997).

Wu et al., "Cytotoxic and antiplatelet aggregation principles from *Aglaia elliptifolia*", *J. Nat. Prod.*, 60: 606-608 (1997).

Adembri et al., "Influence of the solvent on the stereoselectivity of 1,3-dipolar cycloaddition of nitrile oxides on several 4-substituted 2-cyclopentenones," *J. Chem. Res.* 2003(3):126-127 (2003).

Altava et al., "On the origin of changes in topicity observed in Diels-Alder reactions catalyzed by Ti—TADDOLates," *Tetrahedron: Asymmetry* 11(24):4885-4893 (2000).

Bader et al., "Proton transfer in 3-hydroxylavone studied by high-resolution 10 K laser-excited Shpol'skii spectroscopy," *J. Phys. Chem. A.* 106:2844-2849 (2002).

Bauer et al., "Catalytic enantioselective reactions driven by photoinduced electron transfer," *Nature* 436:1139-1140 (2005).

U.S. Appl. No. 60/802,560, filed May 22, 2009, Porco.

U.S. Appl. No. 60/555,448, filed Mar. 23, 2004, Porco et al.

U.S. Appl. No. 60/612,009, filed Sep. 22, 2004, Porco et al.

Beck et al., "Grossansätze zur Herstellung von $\alpha,\alpha,\alpha^1,\alpha^1$-Tetraaryl-1,3-dioxolan-4,5-dimethanolen (TADDOLe): Nützliche Hilfsstoffe für die EPC-Synthese und ihre Struktur im Festkörper," *Chimia* 45:238-244 (1991).

Bhasker Gondi et al., "Hydrogen Bond Catalyzed Enantioselective Vinylogous Mukaiyama Aldol Reaction,"*Org. Lett.* 7(25):5657-5660 (2005).

Brader et al., "Bisamides, lignans, triterpenes, and insecticidal Cyclopenta[b]benzofurans from *Aglaia* species," *J. Nat. Prod.* 61:1482-1490 (1998).

Burke, "Targeting IkappaB kinase for the treatment of inflammatory and other disorders," *Curr. Opin. Drug Discov. Devel.* 6:720-728 (2003).

Chaidir et al., "New Insecticidal Rocaglamide Derivatives from Flowers of *Aglaia duperreana (Meliaceae)*," *Phytochemistry* 52:837-842 (1999).

Cuenca et al., "Highly enantioselective protonation of the 3,4-dihydro-2-methylnaphthalen-1(2H)-one Li-enolate by TADDOLs," *Helv. Chim. Acta* 83:3153-3162 (2000).

Cui et al., "Novel Cytotoxic 1 H-Cyclopenta[b]Benzofuran Lignans from *Aglaia elliptica*," *Tetrahedron* 53:17625-17632 (1997).

Das et al., "A critical role for NF-kappa B in GATA3 expression and TH2 differentiation in allergic airway inflammation," *Nature Immunol.* 2:45-50 (2001).

Demchenko, "Elimination of the Hydrogen Bonding Effect on the Solvatochromism of 3-Hydrxyflavones" *J. Phys. Chem. A* 107:4211-4216 (2003).

Diedrichs et al., "A Highly Efficient Synthesis of Rocaglaols by a Novel α-Arylation of Ketones," *Eur. J. Org. Chem.* 9:1731-1735 (2005).

Dumontet et al., "New nitrogenous and aromatic derivatives from *Aglaia argentwa* and *A. forbesii*," *Tetrahedron* 52: 6931-6942 (1996).

Gagliardo et al., "Persistent Activation of Nuclear Factor-{kappa}B Signaling Pathway in Severe Uncontrolled Asthma," *Am. J. Respir. Crit. Care Med.* 168:1190-1198 (2003).

Garg and Aggarwal, "Nuclear transcription factor-κB as a target for cancer drug development," *Leukemia* 16:1053-1056 (2002).

Gerard et al., "A Biomimetic Approach to the Rocaglamides Employing Photogeneration of Oxidopyryliums Derived from 3-Hydroxyflavones," *J. Am. Chem. Soc.* 126:13620-13621 (2004).

Gerard et al., "Enantioselective Photocycloaddition Mediated by Chiral Brønsted Acids: Asymmetric Synthesis of the Rocaglamides," *J. Am. Chem. Soc.* 128:7754-7755 (2006).

Le Gourrierec et al., "Excited State Intramolecular Proton Transfer Part 2: ESIPT to Oxygen" *Prog. React. Kinet.* 19:211-275 (1994).

Greene et al., "Decarbalkoxylation of [beta]-keto esters—a new mild procedure," *Tetrahedron Lett.* 2707-2708 (1976).

Grosch et al., "'Highly Enantioselective Diels-Alder Reactions of a Photochemically Generated o-Quinodimethane and Olefins," *Angew. Chem., Int. Ed.*, 42:3693-3696 (2003).

Gussregen et al., "Insecticidal rocaglamide derivatives from *Aglaia duppereana*," *Phytochemistry* 44:1455-1461 (1997).

Hailes et al., "A biomimetic approach to the synthesis of rocaglamide based on a photochemical [2+2] cycloaddition of a cinnamate unit to a flavone," *Tetrahedron Lett.*, 34:5313-5316 (1993).

Huang et al., "Tumor necrosis factor modulates transcription of myelin basic protein gene through nuclear factor kappa B in a human oligodendroglioma cell line," *Int. J. Dev. Neurosci.* 20:289-296 (2002).

International Search Report for PCT/US2007/012062, mailed Aug. 5, 2008.

International Search Report for PCT/US2005/010005, mailed Sep. 6, 2005.

Irurre et al., "Synthesis and structure of (4R,5R)-à,à,à',à'-2,2-hexapheny1-4,5-dimethano1-1,3-dioxolane," *Tetrahedron: Asymmetry* 3:1591-1596 (1992).

Ito et al., "Preparation and structural analysis of several new alpha, alpha, alpha'-tetraaryl-1, 3-dioxolane-4, 5-dimethanols (taddols) and taddol analogs, their evaluation as titanium ligands in the enantioselective addition of methyltitanium and diethylzinc reagent," *Helvetica Chim. Acta* 77:2071-2110 (1994).

Jacobsen, "Highly Enantioselective Thiourea-Catalyzed Nitro-Mannich Reactions" *Angew. Chem., Int. Ed.* 44:466-468 (2005).

Jones et al, "NF-κB as an integrator of diverse signaling pathways," *Cardiovasc. Toxicol.* 3:229-254 (2003).

Kaltschmidt et al., "Transcription factor NF-κB is activated in primary neurons by amyloid β peptides and in neurons surrounding early plaques from patients with Alzheimer disease," *Proc. Natl. Acad. Sci. USA* 94:2642-2647 (1997).

Krishna, et al., "Studies towards the synthesis of FCRR toxin: an expedition entry into 7-5-6 ring systems via [5+2] oxidopyrylium-alkene cycloaddition." *Tetrahedron Lett.*, 45 (5) (2004).

Lei et al., "Total synthesis of the ubiquitin-activating enzyme inhibitor (+)-panepophenanthrin," *Angew. Chem., Int. Ed.* 42:3913-3917 (2003).

Legrand et al., "Synthesis, NMR conformational studies and host-guest behaviour of new (+)-tartaric acid derivatives," *Tetrahedron: Asymmetry* 16:635-640 (2005).

Lin et al., "NF-κB in cancer: a marked target," *Semin. Cancer Biol.* 13:107-114 (2003).

Liu et al., "A general protocol for the hydroxylation of C-14 in gibberellins: synthesis of 14β-hydroxy-$GA_1$ methyl ester," *Tetrahedron* 54:11637-11650 (1998).

Mattson et al., "NF-kappaB in neuronal plasticity and neurodegenerative disorders," *J. Clin. Invest.* 107:247-254 (2001).

McDougal et al., "Asymmetric Morita-Baylis-Hillman Reactions Catalyzed by Chiral Brønsted Acids," *J. Am. Chem. Soc.* 125:12094-12095 (2003).

Nugent et al., "Chiral Proton Catalysis: A Catalytic Enantioselective Direct Aza-Henry Reaction," *J. Am. Chem. Soc.* 126:3418-3419 (2004).

Nugroho et al., "Insecticidal Rocaglamide Derivatives from *Aglaia elliptica* and *A. harmisiana*," *Phytochemistry* 45:1579-1585 (1997).

Nugroho et al., "An Insecticidal Rocaglamide Derivatives and Related Compounds from *Aglaia odorata* (*Meliaceae*)," *Phytochemistry* 51:367-376 (1999).

Orlowski et al., "NF-kB as a therapeutic target in cancer," *Trends Mol. Med.* 8:385-389 (2002).

Paquette et al., "The α-Hydroxy Ketone (α-Ketol) and Related Rearrangements" *Org. React.* 62: 477-567 (2003).

Proksch et al., "Chemistry and biological activity of rocaglamide derivatives and related compounds in *Aglaia* species (*Meliaceae*)," *Curr. Org. Chem.* 5:923-938 (2001).

Quadrelli et al., "Intra- and Intermolecular Hydrogen Bonding Effects in Cycloadditions between Nitrile Oxides and 4-Benzoylamino-2-cyclopenten-1-ol and Its Derivatives," *Eur J. Org. Chem.* 13:2058-2065 (2002).

Rastogi et al., "Intramolecular excited-state proton-transfer studies on flavones in different environments," *Spectrochim. Acta, Part A* 57:299-308 (2001).

Rentzea et al., "α-ketol-umlagerung von myrsinol zum iso-myrsinol and mögliche biogenese des myrsinan-derüstes," *Tetrahedron Lett.* 23:1785-1788 (1982).

Roshak et al., "Small-molecule inhibitors of NF-κB for the treatment of inflammatory joint disease," *Curr. Opin. Pharmacol.* 2:316-321 (2002).

Roshal et al., "Flavonols and Crown-Flavonols as Metal Cation Chelators. The Different Nature of $Ba^2$ and $Mg^{2+}$ Complexes" *J. Phys. Chem.* 102:5907-5914 (1998).

Samanta et al., "Evidence of Ground-State Proton Transfer Reaction of 3-Hydroxyflavone in Neutral Alcoholic Solvents" *J. Phys. Chem. A* 107:6334-6339 (2003).

Seebach et al., "On the Ti-TADDOLate-Catalyzed Diels-Alder Addition of 3-Butenoyl-1,3-Oxazolidin-2-One to Cyclopentadiene. General Features of Ti-BINOLate- and Ti-TADDOLate-Mediated Reactions," *J. Org. Chem.* 60:1788 (1995).

Seebach et al., "Mixed β-Peptides: A unique helical secondary structure in solution. Preliminary communication," *Helv. Chim. Acta* 80:2033-2038 (1997).

Seebach et al., "TADDOLs, Their Derivatives, and TADDOL Analogues: Versatile Chiral Auxiliaries," *Angew. Chem. Int. Ed.* 40:92-138 (2001).

Shoelson et al., "Inflammation and the IKK beta/I κβ/NF-κβ axis in obesity- and diet-induced insulin resistance," *Int. J. Obes. Relat Metab. Disord.* 27 (Supp. 3):549-S52 (2003).

Tanaka et al., "Enantioselective [2 +2] photodimerization reactions of coumarins in solution," *Org. Lett.* 7:1501-1503 (2005).

Taylor et al., "Asymmetric Catalysis by Chiral Hydrogen-Bond Donors" *Angew. Chem., Int. Ed.* 45:1520-1543 (2006).

Thadani et al., "Enantioselective Diels—Alder reactions catalyzed by hydrogen bonding," *Proc. Natl. Acad. Sci. U.S.A.* 101:5846-5850 (2004).

Valen et al., "Nuclear factor kappa-B and the heart,"*J. Am. Coll. Cardiol.* 38:307-314 (2001).

Van Heel et al., "Inflammatory bowel disease is associated with a TNF polymorphism that affects an interaction between the OCT1 and NF-κB transcription factors," *Hum. Mol. Genet.* 11:1281-1289 (2002).

Wessig, "Organocatalytic Enantioselective Photoreactions" *Angew. Chem., Int. Ed.* 45:2168-2171 (2006).

Yamamoto et al., "Bronsted Acid Catalysis of Achiral Enamine for Regio- and Enantioselective Nitroso Aldol Synthesis" *J. Am. Chem. Soc.* 127:1080-1081 (2005).

Yamamoto et al., "Role of the NF-κB Pathway in the Pathogenesis of Human Disease States," *Curr. Mol., Med.* 1:287-296 (2001).

Yamamoto et al., "Therapeutic potential of inhibition of the NF-κB pathway in the treatment of inflammation and cancer" *J. Clin. Invest.* 107:135-142 (2001).

Yang et al., "Essential Role of Nuclear Factor κB in the Induction of Eosinophilia in Allergic Airway Inflammation" *J. Exp. Med.* 188:1739-1750 (1998).

A
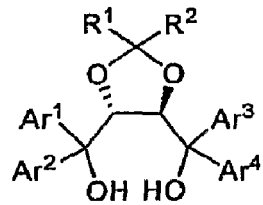 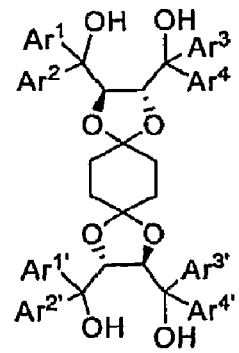
B
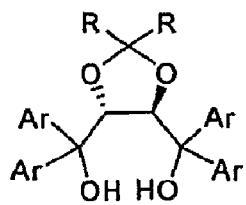
R : Me, Ar: phenyl, 7a
R : Me, Ar : napht-1-yl, 7b
R : Me, Ar : phenanthren-9-yl, 7c
R : H, Ar: phenanthren-9-yl, 7d
R : phenyl, Ar : phenanthr-9-yl, 7e
R : cyclohexyl, Ar : phenanthr-9-yl, 7f
R : cyclooctyl, Ar : pyren-1-yl, 7g
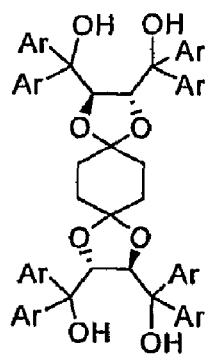
Ar : pyren-1-yl, 8a
Figure 6

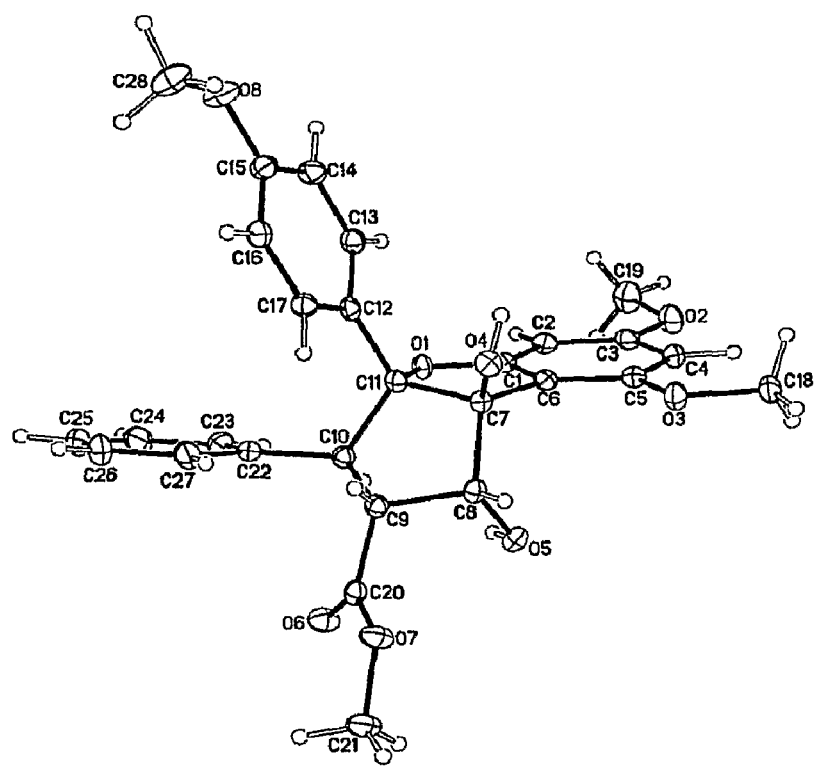
(A)
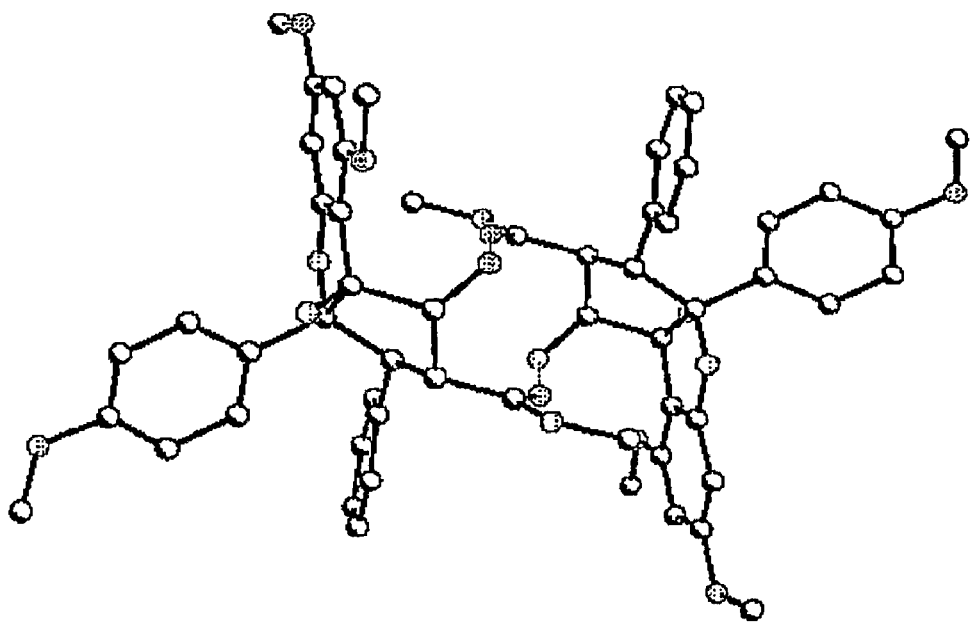
(B)
Figure 13

Crystal data and structure refinement for 1

| | |
|---|---|
| Identification code | 1 |
| Empirical formula | C28 H28 O8 |
| Formula weight | 492.50 |
| Temperature | 173(2) K |
| Wavelength | 0.71073 Å |
| Crystal system | Triclinic |
| Space group | P-1 |
| Unit cell dimensions | a = 10.0768(14) Å    $\alpha$= 109.267(2)°. |
| | b = 10.4422(7) Å    $\beta$= 106.750(3)°. |
| | c = 12.5172(8) Å    $\gamma$ = 96.752(3)°. |
| Volume | 1157.17(19) Å$^3$ |
| Z | 2 |
| Density (calculated) | 1.413 Mg/m$^3$ |
| Absorption coefficient | 0.104 mm$^{-1}$ |
| F(000) | 520 |
| Crystal size | 0.20 x 0.20 x 0.15 mm$^3$ |
| Theta range for data collection | 1.84 to 26.58° |
| Index ranges | -12<=h<=12, -12<=k<=13, -15<=l<=15 |
| Reflections collected | 25370 |
| Independent reflections | 4719 [R(int) = 0.0311] |
| Completeness to theta = 26.58° | 97.4 % |
| Absorption correction | Semi-empirical from equivalents |
| Max. and min. transmission | 0.9846 and 0.9796 |
| Refinement method | Full-matrix least-squares on F$^2$ |
| Data / restraints / parameters | 4719 / 0 / 393 |
| Goodness-of-fit on F$^2$ | 1.097 |
| Final R indices [I>2sigma(I)] | R1 = 0.0360, wR2 = 0.0934 |
| R indices (all data) | R1 = 0.0507, wR2 = 0.0991 |
| Largest diff. peak and hole | 0.251 and -0.230 e.Å$^{-3}$ |

Figure 14

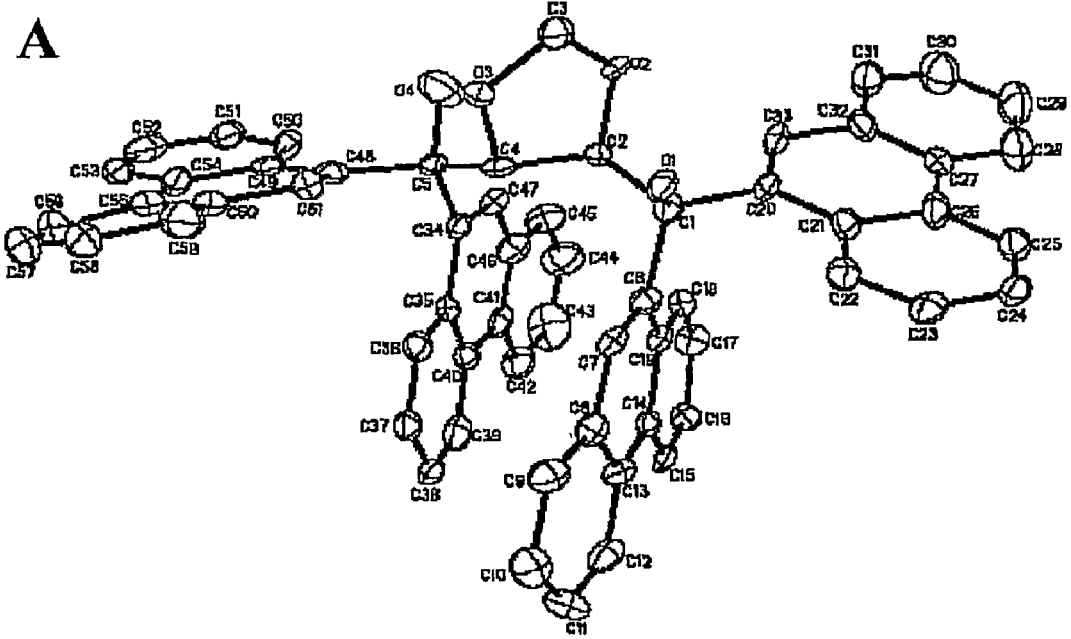
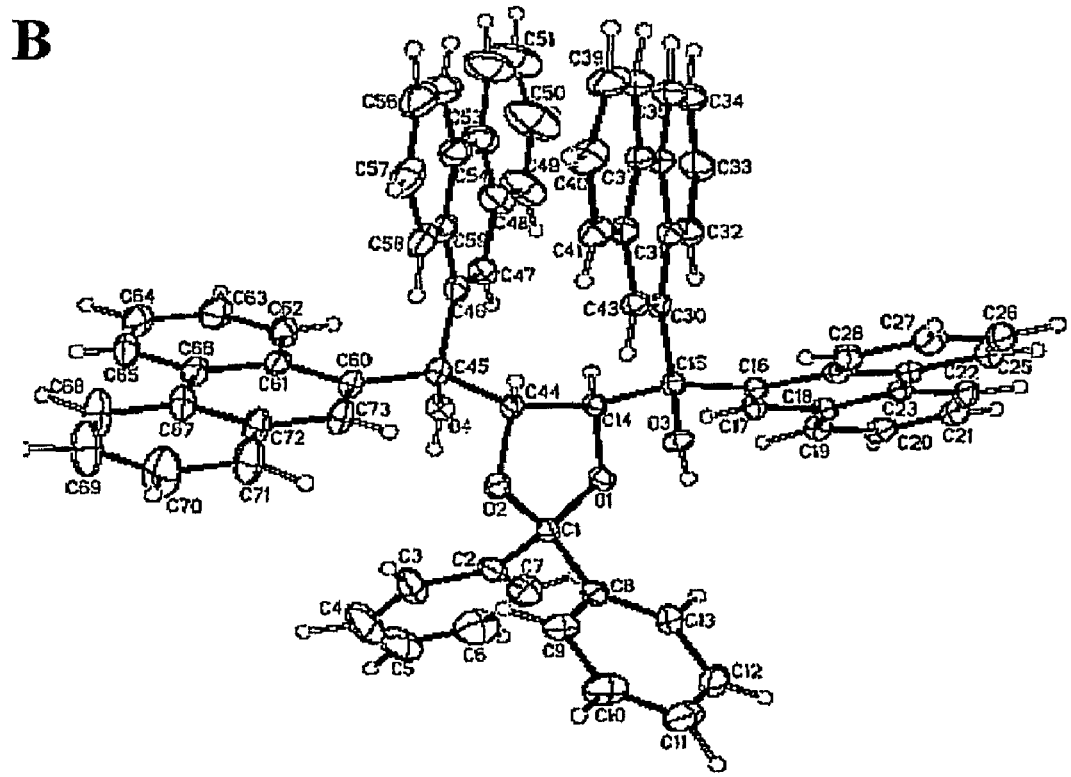
Figure 15

Crystal data and structure refinement for TADDOL 7d

| | | |
|---|---|---|
| Identification code | TADDOL 7d | |
| Empirical formula | C125 H90 CL6 O8 | |
| Formula weight | 1932.67 | |
| Temperature | 173(2) K | |
| Wavelength | 0.71073 Å | |
| Crystal system | Monoclinic | |
| Space group | C2 | |
| Unit cell dimensions | a = 25.6030(13) Å | α = 90°. |
| | b = 16.0366(10) Å | β = 99.148(2)°. |
| | c = 27.6197(16) Å | γ = 90°. |
| Volume | 11196.0(11) Å$^3$ | |
| Z | 4 | |
| Density (calculated) | 1.147 Mg/m$^3$ | |
| Absorption coefficient | 0.208 mm$^{-1}$ | |
| F(000) | 4024 | |
| Crystal size | 0.40 x 0.15 x 0.10 mm$^3$ | |
| Theta range for data collection | 1.49 to 21.49°. | |
| Index ranges | -26<=h<=22, -16<=k<=16, -28<=l<=28 | |
| Reflections collected | 34127 | |
| Independent reflections | 12712 [R(int) = 0.0450] | |
| Completeness to theta = 21.49° | 100.0 % | |
| Absorption correction | Semi-empirical from equivalents | |
| Max. and min. transmission | 0.9795 and 0.9214 | |
| Refinement method | Full-matrix least-squares on F$^2$ | |
| Data / restraints / parameters | 12712 / 1 / 1252 | |
| Goodness-of-fit on F$^2$ | 1.075 | |
| Final R indices [I>2sigma(I)] | R1 = 0.0768, wR2 = 0.2166 | |
| R indices (all data) | R1 = 0.0912, wR2 = 0.2298 | |
| Absolute structure parameter | 0.08(12) | |
| Largest diff. peak and hole | 0.682 and -0.451 e.Å$^{-3}$ | |

Figure 16

Crystal data and structure refinement for TADDOL 7e

| | | |
|---|---|---|
| Identification code | TADDOL 7e | |
| Empirical formula | C73 H50 O4 | |
| Formula weight | 991.13 | |
| Temperature | 173(2) K | |
| Wavelength | 0.71073 Å | |
| Crystal system | Monoclinic | |
| Space group | P2(1) | |
| Unit cell dimensions | a = 10.2354(6) Å | α = 90°. |
| | b = 18.0628(10) Å | β = 103.189(3)°. |
| | c = 16.1878(9) Å | γ = 90°. |
| Volume | 2913.9(3) Å$^3$ | |
| Z | 2 | |
| Density (calculated) | 1.130 Mg/m$^3$ | |
| Absorption coefficient | 0.069 mm$^{-1}$ | |
| F(000) | 1040 | |
| Crystal size | 0.60 x 0.50 x 0.40 mm$^3$ | |
| Theta range for data collection | 1.71 to 28.28°. | |
| Index ranges | -13<=h<=13, -23<=k<=17, -21<=l<=21 | |
| Reflections collected | 40710 | |
| Independent reflections | 12810 [R(int) = 0.0305] | |
| Completeness to theta = 28.28° | 99.5 % | |
| Absorption correction | Semi-empirical from equivalents | |
| Max. and min. transmission | 0.9730 and 0.9599 | |
| Refinement method | Full-matrix least-squares on F$^2$ | |
| Data / restraints / parameters | 12810 / 1 / 882 | |
| Goodness-of-fit on F$^2$ | 1.043 | |
| Final R indices [I>2sigma(I)] | R1 = 0.0453, wR2 = 0.1207 | |
| R indices (all data) | R1 = 0.0506, wR2 = 0.1237 | |
| Absolute structure parameter | 1.6(7) | |
| Largest diff. peak and hole | 0.242 and -0.291 e.Å$^{-3}$ | |

Figure 17

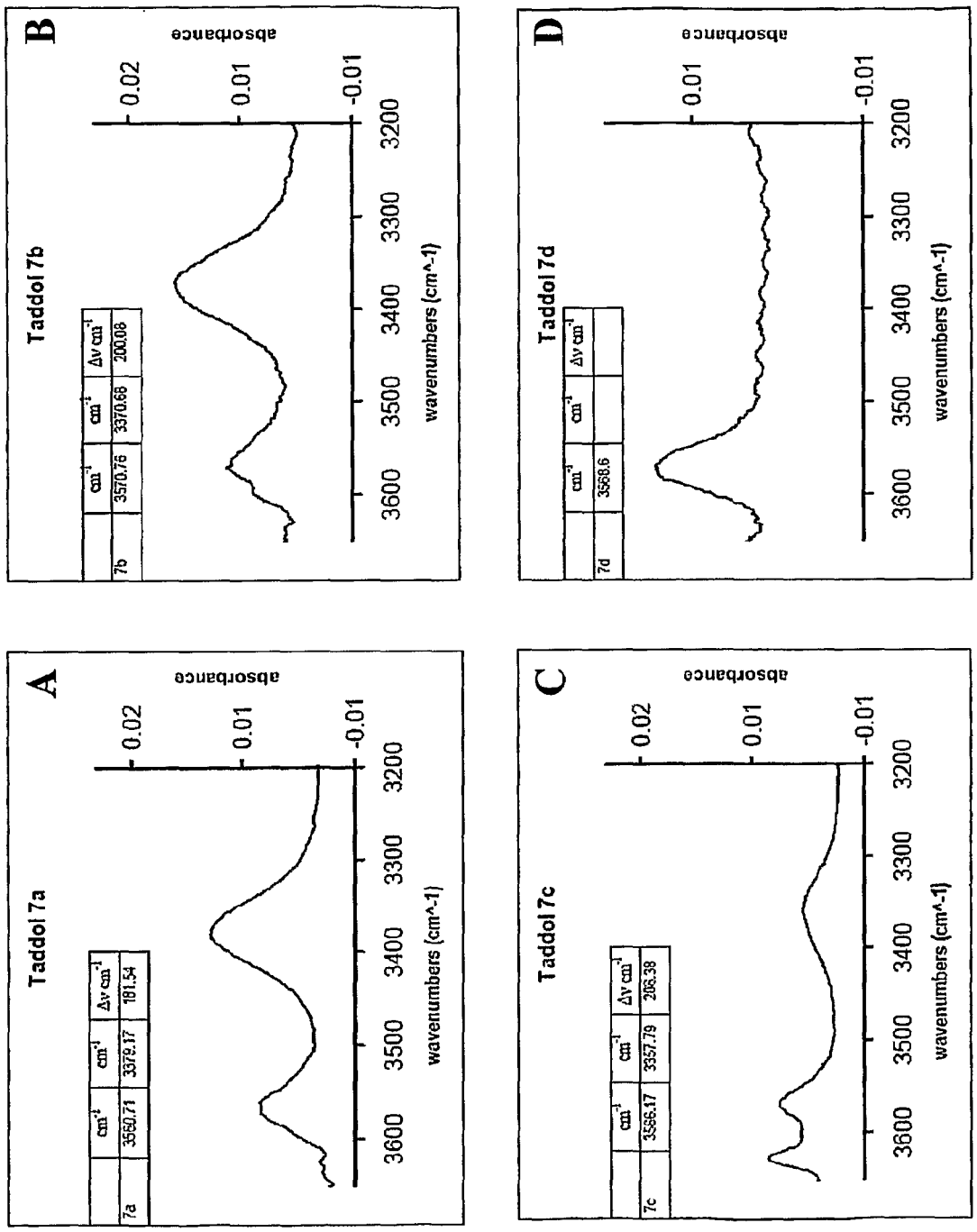
Figure 18(A-D)

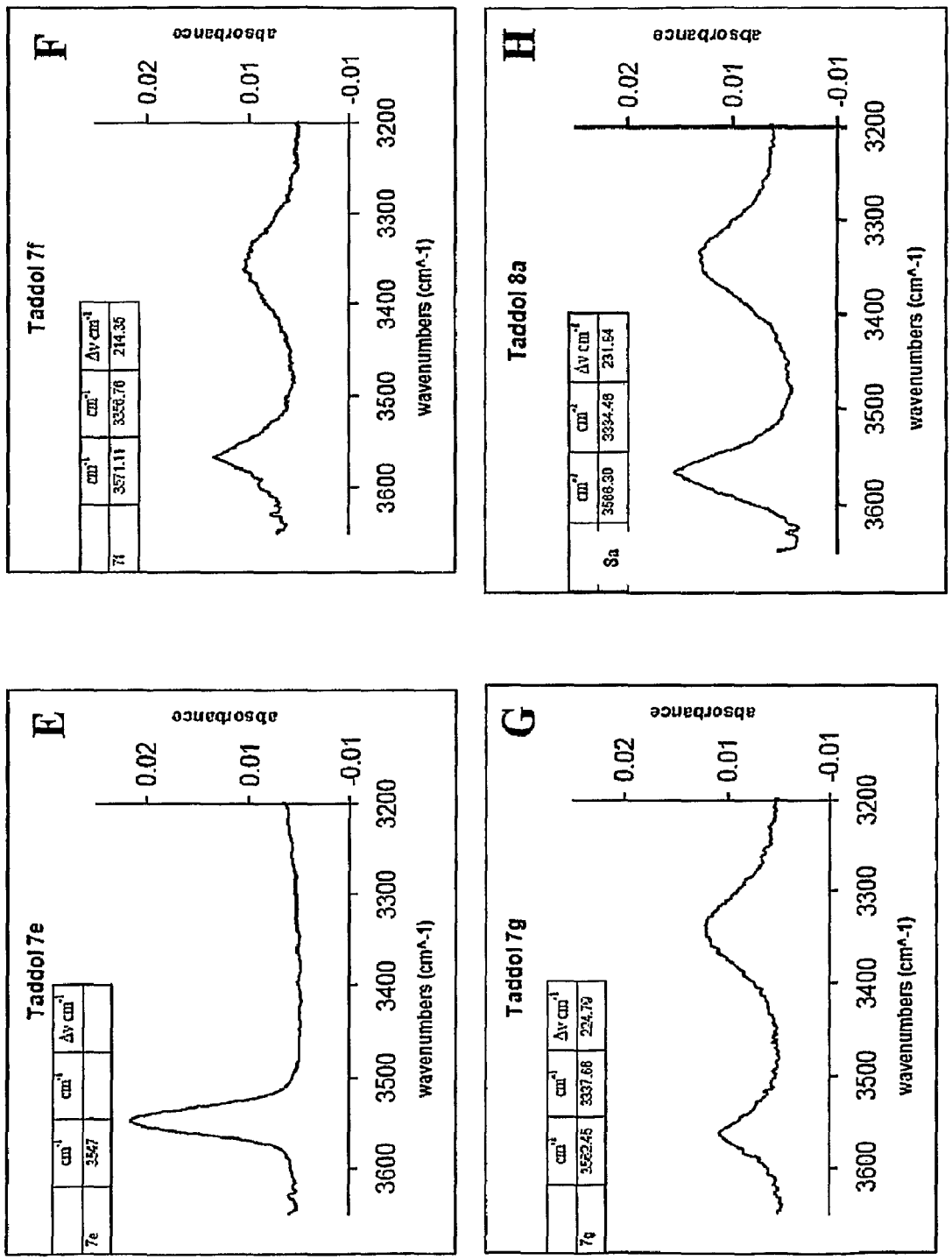
Figure 18(E-H)

ASYMMETRIC SYNTHESIS OF ROCAGLAMIDES VIA ENANTIOSELECTIVE PHOTOCYCLOADDITION MEDIATED BY CHIRAL BRøNSTED ACIDS

RELATED APPLICATIONS

The present application is a U.S. national phase application under 35 U.S.C. 371 of international PCT application no. PCT/US2007/012062, filed May 21, 2007, which claims priority to Provisional Application No. 60/802,560 filed on May 22, 2006. Each of the above-cited patent applications is incorporated herein by reference in its entirety.

GOVERNMENT SUPPORT

The work described herein was made with U.S. government support under Grant No. GM-073855, awarded by the National Institutes of Health. The United States Government has certain rights in the invention.

BACKGROUND OF THE INVENTION

The plant *Aglaia* native of the tropical rain forests of Indonesia and Malaysia is the source of a unique group of densely functionalized natural products some of which are presented on FIG. 1 (P. Proksch et al., Curr. Org. Chem., 2001, 5: 923-938). The rocaglamides, including the parent molecule (compound A; M. L. King et al., J. Chem. Soc., Chem. Commun., 1982, 1150-1151) and the recently isolated dioxanyloxy-modified derivative silvestrol (compound B; B. Y. Hwang et al., J. Org. Chem., 2004, 69: 3350-3358), possess a cyclopenta[b]tetrahydrobenzofuran ring system (presented in red on FIG. 1). The structurally related aglains (e.g., compounds C and D), which contain a cyclopenta[bc]benzopyran structure (presented in blue on FIG. 1), have also been isolated from *Aglaia* (V. Dumontet et al., Tetrahedron, 1996, 52: 6931-6942). The forbaglins (e.g., compound E) are benzo[b]oxepines (in green on FIG. 1) derived from formal oxidative cleavage of the aglain core.

The rocaglamides have been shown to exhibit potent anticancer (M. L. King et al., J. Chem. Soc., Chem. Commun., 1982, 1150-1151) and antileukemic activity (S. K. Lee et al., Chem. Biol. Interact., 1998, 115: 215-228) as well as NF-κB inhibitory activity at nanomolar concentrations in human T cells (13. Baumann et al., J. Biol. Chem., 2002, 277: 44791-44800). The rocaglate silvestrol B displays cytotoxic activity against human cancer cells comparable to the anticancer drug TAXOL® (B. Y. Hwang et al., J. Org. Chem., 2004, 69: 3350-3358).

As proposed by Proksch (P. Proksch et al., Curr. Org. Chem., 2001, 5: 923-938) and Bacher (M. Bacher et al., Phytochemistry, 1999, 52: 253-263), and as shown on FIG. 2, the rocaglamides may be biosynthetically derived from reaction of trimethoxy-substituted 3-hydroxyflavone with cinnamide derivatives to afford the aglain core, followed by skeletal rearrangement.

The rocaglamides have been the subject of a number of synthetic investigations (see, for example, G. A. Kraus and J. O, Sy, J. Org. Chem., 1989, 54: 77-83; B. Trost et al., J. Am. Chem. Soc., 1990, 112: 9022-9024), including a biomimetic approach involving a [2+2] photocycloaddition (H. C. Hailes et al., Tetrahedron Lett., 1993, 34: 5313-5316). However, syntheses of the related aglain (V. Dumontet et al., Tetrahedron, 1996, 52: 6931-6942), aglaforbesin (V. Dumontet et al., Tetrahedron, 1996, 52: 6931-6942), or forbaglins have not been reported. A unified synthetic approach to these molecules based on biosynthetic still remains to be developed.

The present Applicants have recently reported (B. Gerard et al., J. Am. Chem. Soc., 2004, 126: 13620-13621; and International Application WO 2005/092876) the synthesis of rocaglamide natural products via [3+2] dipolar cycloaddition of an oxidopyrylium species derived from excited state intramolecular proton transfer (a general synthetic scheme is presented on FIG. 3).

SUMMARY OF THE INVENTION

The present invention is directed to new strategies for the synthesis of natural products and derivatives in the rocaglamide/aglain/forbaglin family. In particular, the present invention provides methods for the preparation of chiral, nonracemic rocaglate derivatives. More specifically, the present invention encompasses the recognition that a 1,3-dipolar cycloaddition (i.e., [3+2]cycloaddition) between a photochemically generated oxidopyrylium species and a dipolarophile becomes enantioselective when carried out in the presence of a functionalized TADDOL derivative used as a chiral Brønsted acid. This enantioselective reaction was successfully employed in the synthesis of rocaglamide derivatives.

Accordingly, one aspect of the present invention relates to a method comprising steps of: photochemically generating an oxidopyrylium species from a 3-hydroxychromone derivative; and reacting the oxidopyrylium species with a dipolarophile, wherein the steps of photochemically generating the oxidopyrylium species and of reacting the oxidopyrylium species with a dipolarophile are carried out in the presence of a TADDOL derivative. In many embodiments, the step of reacting the oxidopyrylium species and the dipolarophile comprises a cycloaddition (e.g., a 1,3-dipolar cycloaddition) leading to the formation of an adduct. In certain preferred embodiments, the cycloaddition is enantioselective.

In preferred embodiments, the oxidopyrylium species is photochemically generated via a process comprising an excited state intramolecular proton transfer.

In certain embodiments, the oxidopyrylium species is photochemically generated from a 3-hydroxychromone derivative with the following chemical structure:

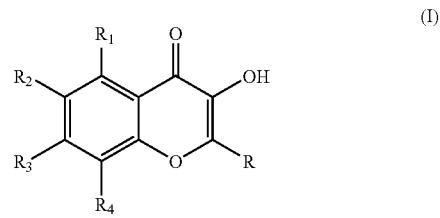

(I)

wherein $R_1$, $R_2$, $R_3$, $R_4$ and R are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, $-NO_2$, $-CN$, $-CF_3$, $-CH_2CF_3$, $-CHCl_2$, $-CH_2OH$, $-CH_2CH_2OH$, $-CH_2SO_2CH_3$, $-C(=O)R_x$, $-CO_2(R_x)$, $-C(=O)N(R_x)_2$, $-OC(=O)N(R_x)_2$, $-OC(=O)R_x$, $-OCO_2R_x$, $-S(O)R_x$, $-S(O)_2R_x$, $-NR_x(CO)R_x$, $-N(R_x)CO_2R_x$, $-N(R_x)C(=O)N(R_x)_2$, $-N(R_x)S(O)_2R_x$, and $-S(O)_2N(R_x)_2$, wherein each occurrence of $R_x$ is independently selected from the group consisting of hydrogen, aliphatic, alicyclic, heteroaliphatic, heterocyclic, aromatic, heteroaromatic, aryl, and heteroaryl.

In other embodiments, the oxidopyrylium species is photochemically generated from a 3-hydroxychromone derivative with the following chemical structure:

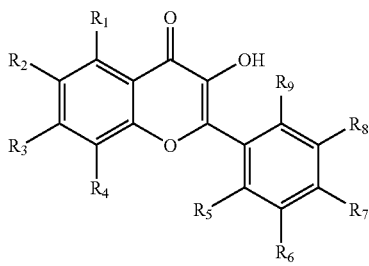

(II)

wherein $R_1$, $R_2$, $R_3$, $R_4$, $R_5$, $R_6$, $R_7$, $R_8$ and $R_9$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, $—NO_2$, $—CN$, $—CF_3$, $—CH_2CF_3$, $—CHCl_2$, $—CH_2OH$, $—CH_2CH_2OH$, $—CH_2SO_2CH_3$, $—C(=O)R_x$, $—CO_2(R_x)$, $—C(=O)N(R_x)_2$, $—OC(=O)N(R_x)_2$, $—OC(=O)R_x$, $—OCO_2R_x$, $—S(O)R_x$, $—S(O)_2R_x$, $—NR_x(CO)R_x$, $—N(R_x)CO_2R_x$, $—N(R_x)C(=O)N(R_x)_2$, $—N(R_x)S(O)_2R_x$, and $—S(O)_2N(R_x)_2$, wherein each occurrence of $R_x$ is independently selected from the group consisting of hydrogen, aliphatic, alicyclic, heteroaliphatic, heterocyclic, aromatic, heteroaromatic, aryl, and heteroaryl.

For example, the 3-hydroxyflavaone derivative may have one of the following chemical structures:

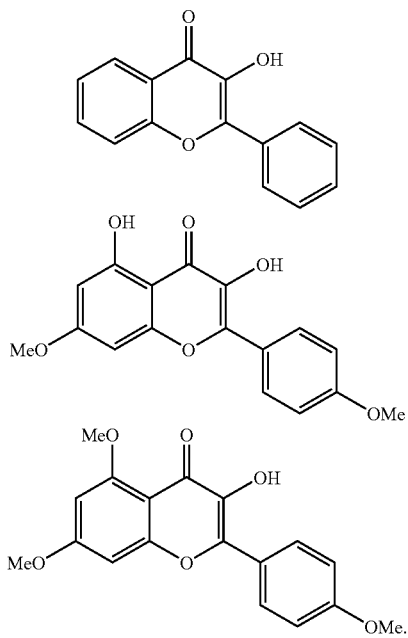

In certain embodiments, the dipolarophile is a cinnamate derivative.

In certain embodiments, the TADDOL derivative is a L-tartrate derivative. For example, in certain embodiments, the TADDOL derivative has the following structure:

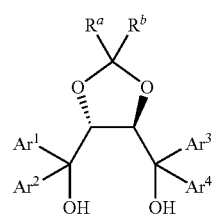

wherein $R^a$ and $R^b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, $—NO_2$, $—CN$, $—CF_3$, $—CH_2CF_3$, $—CHCl_2$, $—CH_2OH$, $—CH_2CH_2OH$, $—CH_2SO_2CH_3$, $—C(=O)R^x$, $—CO_2(R^x)$, $—C(=O)N(R^x)_2$, $—OC(=O)N(R^x)_2$, $—OC(=O)R^x$, $—OCO_2R^x$, $—S(O)R^x$, $—S(O)_2R^x$, $—NR^x(CO)R^x$, $—N(R^x)CO_2R^x$, $—N(R^x)C(=O)N(R^x)_2$, $—N(R^x)S(O)_2R^x$, and $—S(O)_2N(R^x)_2$, wherein each occurrence of $R^x$ is independently selected from the group consisting of hydrogen, aliphatic, alicyclic, heteroaliphatic, heterocyclic, aromatic, heteroaromatic, aryl, and heteroaryl; and wherein $Ar^1$, $Ar^2$, $Ar^3$, and $Ar^4$ are be identical or different and selected from the group consisting of substituted or unsubstituted aryloxy, heteroaryloxy, thioaryl, aryl, heteroaryl, arylamino, and amino aryl.

In other embodiments, the TADDOL derivative has the following structure:

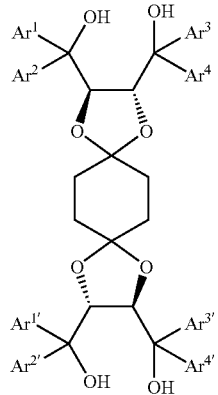

wherein $Ar^1$, $Ar^2$, $Ar^3$, $Ar^4$ $Ar^{1'}$, $Ar^{2'}$, $Ar^{3'}$, and $Ar^{4'}$ are identical or different and selected from the group consisting of substituted or unsubstituted aryloxy, heteroaryloxy, thioaryl, aryl, heteroaryl, arylamino, and amino aryl.

In certain embodiments, the steps of photochemically generating the oxidopyrylium species and of reacting the oxidopyrylium species with a dipolarophile are carried out in an aprotic solvent. The aprotic solvent may be selected from the group consisting of hexane, toluene, pentane, cyclohexane, dioxane, carbon tetrachloride, benzene, carbon disulfide, toluene, diethyl ether, chloroform, ethyl acetate, tetrahydrofuran, methylene chloride, pyridine, dimethylformamide, acetonitrile, dimethylsulfoxide, and combinations thereof.

In certain embodiments, the steps of photochemically generating the oxidopyrylium species and of reacting the oxidopyrylium species with a dipolarophile are carried out at a temperature lower than 0° C. The temperature lower than 0° C. may be comprised in a range selected from the group consisting of between −20° C. and −40° C., between −30° C. and −50° C., between −40° C. and −60° C., between −50° C. and −70° C., between −60° C. and −80° C., and between −70° C. and −90° C.

In certain embodiments, the synthetic method further comprises a step of converting the adduct formed by the cycloaddition. For example, when the adduct formed comprises an aglain core structure, converting the adduct may result in formation of a ring system selected from the group consisting of an aglain ring system, a rocaglamide ring system, and a forbaglin ring system.

In another aspect, the present invention provides a method for preparing a compound with an aglain core structure. In one embodiment, such method comprises steps of:
 producing an oxidopyrylium species ($I_T$) by photoinduced excited state intramolecular proton transfer of a 3-hydroxychromone derivative (I); and
 reacting the oxidopyrylium species with a dipolarophile (IV) to obtain the aglain core-containing compound (V), wherein compounds (I), ($I_T$), (IV) and (V) have the following chemical structures:

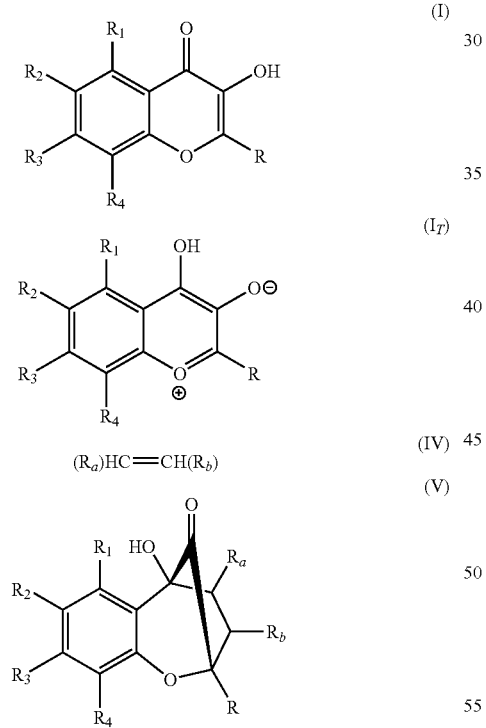

wherein $R_1$, $R_2$, $R_3$, $R_4$, R, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —C(=O)$R_x$, —$CO_2(R_x)$, —C(=O)N($R_x$)$_2$, —OC(=O)N($R_x$)$_2$, —OC(=O)$R_x$, —$OCO_2R_x$, —S(O)$R_x$, —S(O)$_2R_x$, —$NR_x$(CO)$R_x$, —N($R_x$)$CO_2R_x$, —N($R_x$)C(=O)N($R_x$)$_2$, —N($R_x$)S(O)$_2R_x$, and —S(O)$_2$N($R_x$)$_2$,
 wherein each occurrence of $R_x$ is independently selected from the group consisting of hydrogen, aliphatic, alicyclic, heteroaliphatic, heterocyclic, aromatic, heteroaromatic, aryl, and heteroaryl, and
wherein the steps of producing the oxidopyrylium species and of reacting the oxidopyrylium species with a dipolarophile are carried out in the presence of a TADDOL derivative.

In another embodiment, such method comprises steps of:
producing an oxidopyrylium species ($II_T$) by photoinduced excited state intramolecular proton transfer of a 3-hydroxyflavone derivative (II); and
reacting the oxidopyrylium species with a dipolarophile (IV) to obtain the aglain core-containing compound (V'), wherein compounds (II), ($II_T$), (IV) and (V') have the following chemical structures:

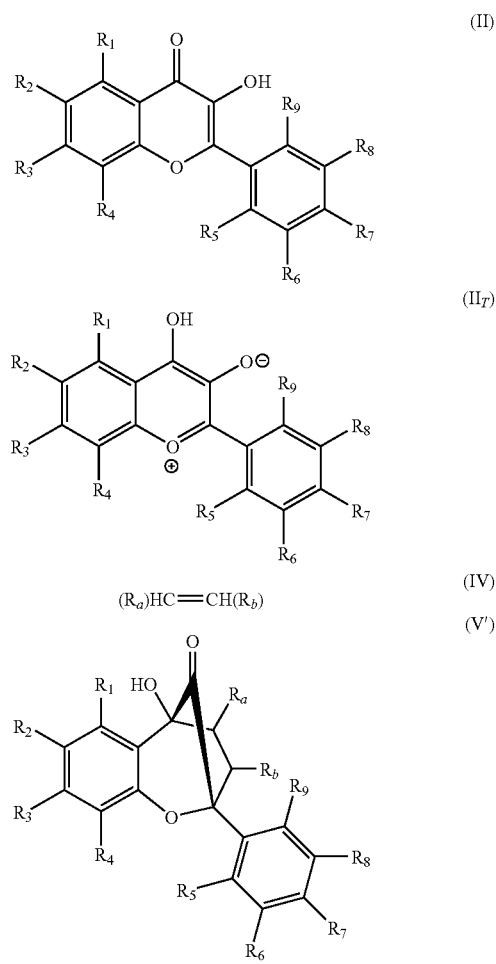

wherein $R_1$, $R_2$, $R_3$, $R_4$, $R_5$, $R_6$, $R_7$, $R_8$, $R_9$, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —$C(=O)R_x$, —$CO_2(R_x)$, —$C(=O)N(R_x)_2$, —$OC(=O)N(R_x)_2$, —$OC(=O)R_x$, —$OCO_2R_x$, —$S(O)R_x$, —$S(O)_2R_x$, —$NR_x(CO)R_x$, —$N(R_x)CO_2R_x$, —$N(R_x)C(=O)N(R_x)_2$, —$N(R_x)S(O)_2R_x$, and —$S(O)_2N(R_x)_2$, wherein each occurrence of $R_x$ is independently selected from the group consisting of hydrogen, aliphatic, alicyclic, heteroaliphatic, heterocyclic, aromatic, heteroaromatic, aryl, and heteroaryl, and wherein the steps of producing the oxidopyrylium species and reacting the oxidopyrylium species with a dipolarophile are carried out in the presence of a TADDOL derivative.

For example, the 3-hydroxyflavone derivative may have one of the following chemical structures:

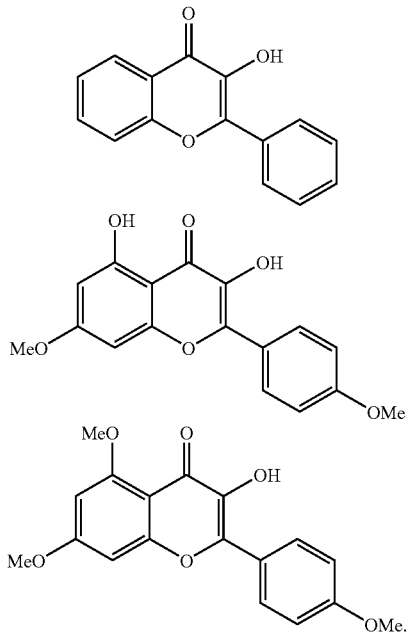

In certain embodiments of such methods, the step of reacting the oxidopyrylium species with the dipolarophile comprises a 1,3-dipolar cycloaddition. Preferably, the cycloaddition is enantioselective.

In certain embodiments of such methods, the dipolarophile (IV) is a cinnamate derivative with the following chemical structure:

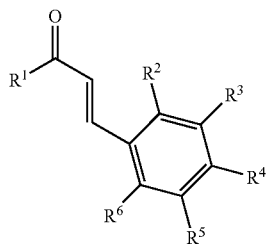

wherein $R^1$ is selected from the group consisting of hydrogen, hydroxy, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, and a protecting group; and wherein $R^2$, $R^3$, $R^4$, $R^5$, and $R^6$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —$C(=O)R_x$, —$CO_2(R_x)$, —$C(=O)N(R_x)_2$, —$OC(=O)N(R_x)_2$, —$OC(=O)R_x$, —$OCO_2R_x$, —$S(O)R_x$, —$S(O)_2R_x$, —$NR_x(CO)R_x$, —$N(R_x)CO_2R_x$, —$N(R_x)C(=O)N(R_x)_2$, —$N(R_x)S(O)_2R_x$, and —$S(O)_2N(R_x)_2$, wherein each occurrence of $R_x$ is independently selected from the group consisting of hydrogen, aliphatic, alicyclic, heteroaliphatic, heterocyclic, aromatic, heteroaromatic, aryl, and heteroaryl.

In certain embodiments of such methods, the TADDOL derivative is a L-tartrate derivative. For example, in certain embodiments, the TADDOL derivative has the following structure:

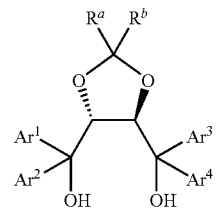

wherein $R^a$ and $R^b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —$C(=O)R^x$, —$CO_2(R^x)$, —$C(=O)N(R^x)_2$, —$OC(=O)N(R^x)_2$, —$OC(=O)R^x$, —$OCO_2R^x$, —$S(O)R^x$, —$S(O)_2R^x$, —$NR^x(CO)R^x$, —$N(R^x)CO_2R^x$, —$N(R^x)C(=O)N(R^x)_2$, —$N(R^x)S(O)_2R^x$, and —$S(O)_2N(R^x)_2$, wherein each occurrence of $R^x$ is independently selected from the group consisting of hydrogen, aliphatic, alicyclic, heteroaliphatic, heterocyclic, aromatic, heteroaromatic, aryl, and heteroaryl; and wherein $Ar^1$, $Ar^2$, $Ar^3$, and $Ar^4$ are be identical or different and selected from the group consisting of substituted or unsubstituted aryloxy, heteroaryloxy, thioaryl, aryl, heteroaryl, arylamino, and amino aryl.

In other embodiments, the TADDOL derivative has the following structure:

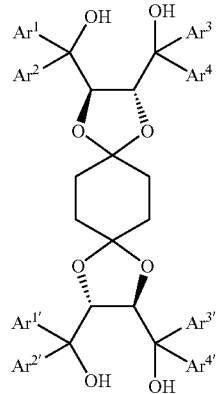

wherein $Ar^1$, $Ar^2$, $Ar^3$, $Ar^4$ $Ar^{1'}$, $Ar^{2'}$, $Ar^{3'}$, and $Ar^{4'}$ are identical or different and selected from the group consisting of substituted or unsubstituted aryloxy, heteroaryloxy, thioaryl, aryl, heteroaryl, arylamino, and amino aryl.

In certain embodiments of such methods, the steps of producing the oxidopyrylium species and of reacting the oxidopyrylium species with a dipolarophile are carried out in an aprotic solvent. The aprotic solvent may be selected from the group consisting of hexane, toluene, pentane, cyclohexane, dioxane, carbon tetrachloride, benzene, carbon disulfide, toluene, diethyl ether, chloroform, ethyl acetate, tetrahydrofuran, methylene chloride, pyridine, dimethylformamide, acetonitrile, dimethylsulfoxide, and combinations thereof.

In certain embodiments of such methods, the steps of producing the oxidopyrylium species and of reacting the oxidopyrylium species with a dipolarophile are carried out at a temperature lower than 0° C. The temperature lower than 0° C. may be comprised in a range selected from the group consisting of between −20° C. and −40° C., between −30° C. and −50° C., between −40° C. and −60° C., between −50° C. and −70° C., between −60° C. and −80° C., and between −70° C. and −90° C.

In certain embodiments, the method further comprises a step of converting the compound with an aglain core structure into a rocaglamide (VII) with the following chemical structure:

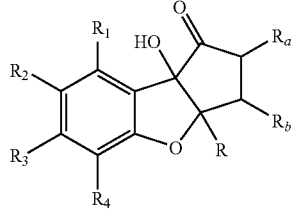

(VII)

wherein $R_1$, $R_2$, $R_3$, $R_4$, R, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —C(=O)$R_x$, —$CO_2(R_x)$, —C(=O)N($R_x$)$_2$, —OC(=O)N($R_x$)$_2$, —OC(=O)$R_x$, —$OCO_2R_x$, —S(O)$R_x$, —S(O)$_2R_x$, —$NR_x$(CO)$R_x$, —N($R_x$)$CO_2R_x$, —N($R_x$)C(=O)N($R_x$)$_2$, —N($R_x$)S(O)$_2R_x$, and —S(O)$_2$N($R_x$)$_2$,
wherein each occurrence of $R_x$ is independently selected from the group consisting of hydrogen, aliphatic, alicyclic, heteroaliphatic, heterocyclic, aromatic, heteroaromatic, aryl, and heteroaryl.

In other embodiments, the method further comprises a step of converting the compound with an aglain core structure into a rocaglamide (VII') with the following chemical structure:

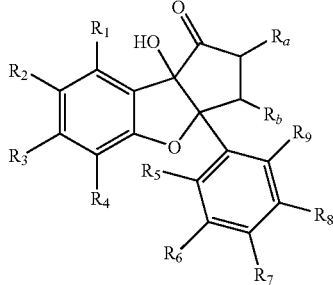

(VII')

wherein $R_1$, $R_2$, $R_3$, $R_4$, $R_5$, $R_6$, $R_7$, $R_8$, $R_9$, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —C(=O)$R_x$, —$CO_2(R_x)$, —C(=O)N($R_x$)$_2$, —OC(=O)N($R_x$)$_2$, —OC(=O)$R_x$, —$OCO_2R_x$, —S(O)$R_x$, —S(O)$_2R_x$, —$NR_x$(CO)$R_x$, —N($R_x$)$CO_2R_x$, —N($R_x$)C(=O)N($R_x$)$_2$, —N($R_x$)S(O)$_2R_x$, and —S(O)$_2$N($R_x$)$_2$,
wherein each occurrence of $R_x$ is independently selected from the group consisting of hydrogen, aliphatic, alicyclic, heteroaliphatic, heterocyclic, aromatic, heteroaromatic, aryl, and heteroaryl.

Converting the compound with an aglain core structure into a rocaglamide derivative may comprise an α-ketol (acyloin) rearrangement, for example, a base-mediated α-ketol (acyloin) rearrangement.

In certain embodiments, the method further comprises a step of converting the compound with an aglain core structure into a rocaglamide derivative (VIII) with the following chemical structure:

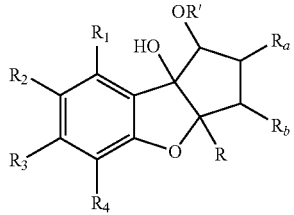

(VIII)

wherein $R_1$, $R_2$, $R_3$, $R_4$, R, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —C(=O)$R_x$, —$CO_2(R_x)$, —C(=O)N($R_x$)$_2$, —OC(=O)N($R_x$)$_2$, —OC(=O)$R_x$, —$OCO_2R_x$, —S(O)$R_x$, —S(O)$_2R_x$, —$NR_x$(CO)$R_x$, —N($R_x$)$CO_2R_x$, —N($R_x$)C(=O)N($R_x$)$_2$—N($R_x$)S(O)$_2R_x$, and —S(O)$_2$N($R_x$)$_2$,
wherein each occurrence of $R_x$ is independently selected from the group consisting of hydrogen, aliphatic, alicyclic, heteroaliphatic, heterocyclic, aromatic, heteroaromatic, aryl, and heteroaryl; and
wherein R' is selected from the group consisting of hydrogen, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, a protecting group, —$CH_2OH$, —$CH_2CH_2OH$, —$CH_2SO_2CH_3$, —C(=O)$R_x$, —$CO_2(R_x)$, —C(=O)N($R_x$)$_2$, —S(O)$R_x$, —$NR_x$(CO)$R_x$, —N($R_x$)$CO_2R_x$, —N($R_x$)C(=O)N($R_x$)$_2$, and —N($R_x$)S(O)$_2R_x$,
wherein each occurrence of $R_x$ is independently selected from the group consisting of hydrogen, aliphatic, alicyclic, heteroaliphatic, heterocyclic, aromatic, heteroaromatic, aryl, and heteroaryl.

In other embodiments, the method further comprises a step of converting the compound with an aglain core structure into a rocaglamide derivative (VIII') with the following chemical structure:

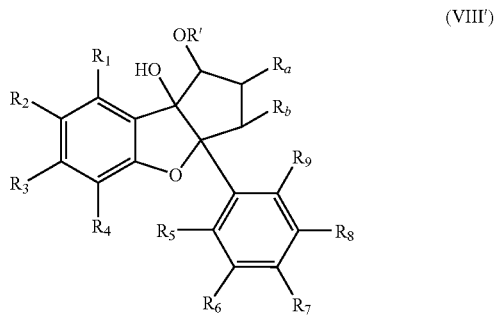

(VIII')

wherein $R_1$, $R_2$, $R_3$, $R_4$, $R_5$, $R_6$, $R_7$, $R_8$, $R_9$, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —C(=O)$R_x$, —$CO_2(R_x)$, —C(=O)N$(R_x)_2$, —OC(=O)N$(R)_2$, —OC(=O)$R_x$, —$OCO_2R_x$, —S(O)$R_x$, —S(O)$_2R_x$, —$NR_x$(CO)$R_x$, —N$(R_x)CO_2R_x$, —N$(R_x)$C(=O)N$(R_x)_2$, —N$(R_x)$S(O)$_2R_x$, and —S(O)$_2$N$(R_x)_2$, wherein each occurrence of $R_x$ is independently selected from the group consisting of hydrogen, aliphatic, alicyclic, heteroaliphatic, heterocyclic, aromatic, heteroaromatic, aryl, and heteroaryl; and wherein R' is selected from the group consisting of hydrogen, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, a protecting group, —$CH_2OH$, —$CH_2CH_2OH$, —$CH_2SO_2CH_3$, —C(=O)$R_x$, —$CO_2(R_x)$, —C(=O)N$(R_x)_2$, —S(O)$R_x$, —$NR_x$(CO)$R_x$, —N$(R_x)CO_2R_x$, —N$(R_x)$C(=O)N$(R_x)_2$, and —N$(R_x)$S(O)$_2R_x$, wherein each occurrence of $R_x$ is independently selected from the group consisting of hydrogen, aliphatic, alicyclic, heteroaliphatic, heterocyclic, aromatic, heteroaromatic, aryl, and heteroaryl.

In such embodiments, converting the compound with an aglain core structure into a rocaglamide derivative may comprises an α-ketol (acyloin) rearrangement and a hydroxyl-directed reduction.

In certain embodiments, the method comprises a mixture of endo and exo isomers of the rocaglamide derivative such that the mixture comprises more endo isomer than exo isomer.

Another aspect of the present invention relates to aglain core containing compounds (V) and (V'), and rocaglamide derivatives (VII), (VII'), (VIII) and (VIII') prepared by the methods disclosed herein.

Another aspect of the present invention relates to the use of these compounds and derivatives for the manufacture of medicaments for use in the treatment of disease states including cancer or cancerous conditions, conditions associated with cellular proliferation, and NF-κB-associated conditions.

For example, cancer and cancerous conditions that may be treated by such medicaments include leukemia, sarcoma, breast, colon, bladder, pancreatic, endometrial, head and neck, mesothelioma, myeloma, oesophageal/oral, testicular, thyroid, cervical, bone, renal, uterine, prostate, brain, lung, ovarian, skin, liver and bowel and stomach cancers, tumors and melanomas. Conditions associated with cellular hyperproliferation that can be treated using the inventive medicaments may be selected from the group consisting of atherosclerosis, restenosis, rheumatoid arthritis, osteoarthritis, inflammatory arthritis, psoriasis, periodontal disease and virally induced cellular proliferation. NF-κB associated conditions that can be treated using the medicaments disclosed herein may be selected from the group consisting of immunological disorders, septic shock, transplant rejection, radiation damage, reperfusion injuries after ischemia, artherioesclerosis and neurodegenerative diseases.

BRIEF DESCRIPTION OF THE DRAWING

FIG. 6(A) shows the general chemical structure of TADDOL derivatives and dimeric TADDOL derivatives that can be used in methods of the present invention. FIG. 6(B) shows chemical structures of some of the functionalized TADDOL derivatives used by the present Applicants.

Table 1 shows reaction yields and ee values for rocaglamate preparation according to methods of the present invention, where the [3+2] photocycloaddition was carried out in the absence (entry 1) and in the presence (entries 2 to 12) of different functionalized TADDOL derivatives.

Table 2 shows results of experiments carried out to determine the influence of temperature and solvent on the enantioselectivity of a rocaglamate preparation according to methods of the present invention, where the [3+2] photocycloaddition was carried out in the presence of a functionalized TADDOL derivative.

Table 3 shows results of experiments carried out to determine the influence of stoichiometry and concentration on the enantioselectivity of a rocaglamate preparation according to methods of the present invention, wherein the [3+2] photocycloaddition was carried out in the presence of a functionalized TADDOL derivative.

Figure 7:
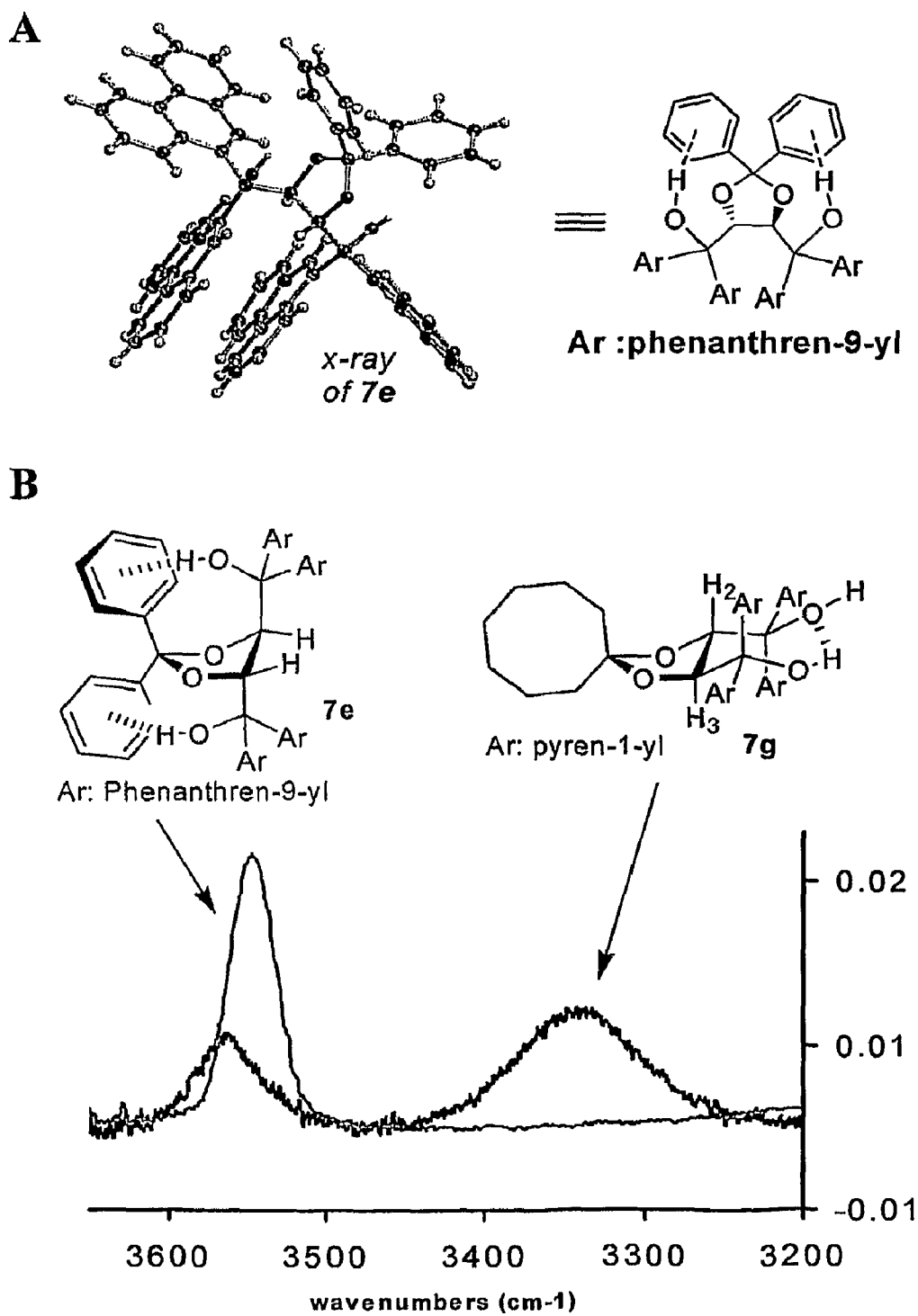

FIG. 7(A) shows a conformer of 7e involving intramolecular H-binding between the hydroxyl groups and the π system of the phenanthrene ring (i.e., no or weak intramolecular OH/OH hydrogen bond). FIG. 7(B) shows the IR hydroxyl stretching frequencies of compound 7e (wherein no or weak intramolecular OH/OH hydrogen bonding takes place) and of compound 7g (wherein intramolecular OH/OH hydrogen bonding takes place).

Figure 8:
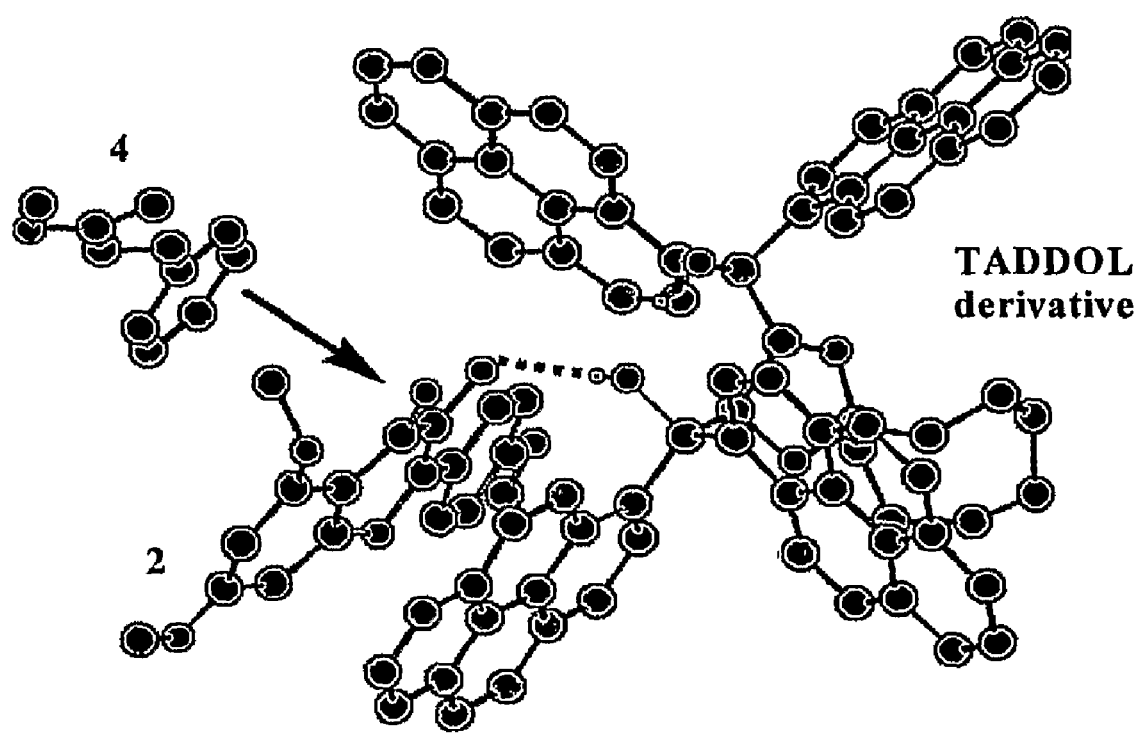

FIG. 8 shows the proposed arrangement for enantioselective [3+2] photocycloaddition in the presence of a TADDOL derivative according to the present invention.

Figure 9:
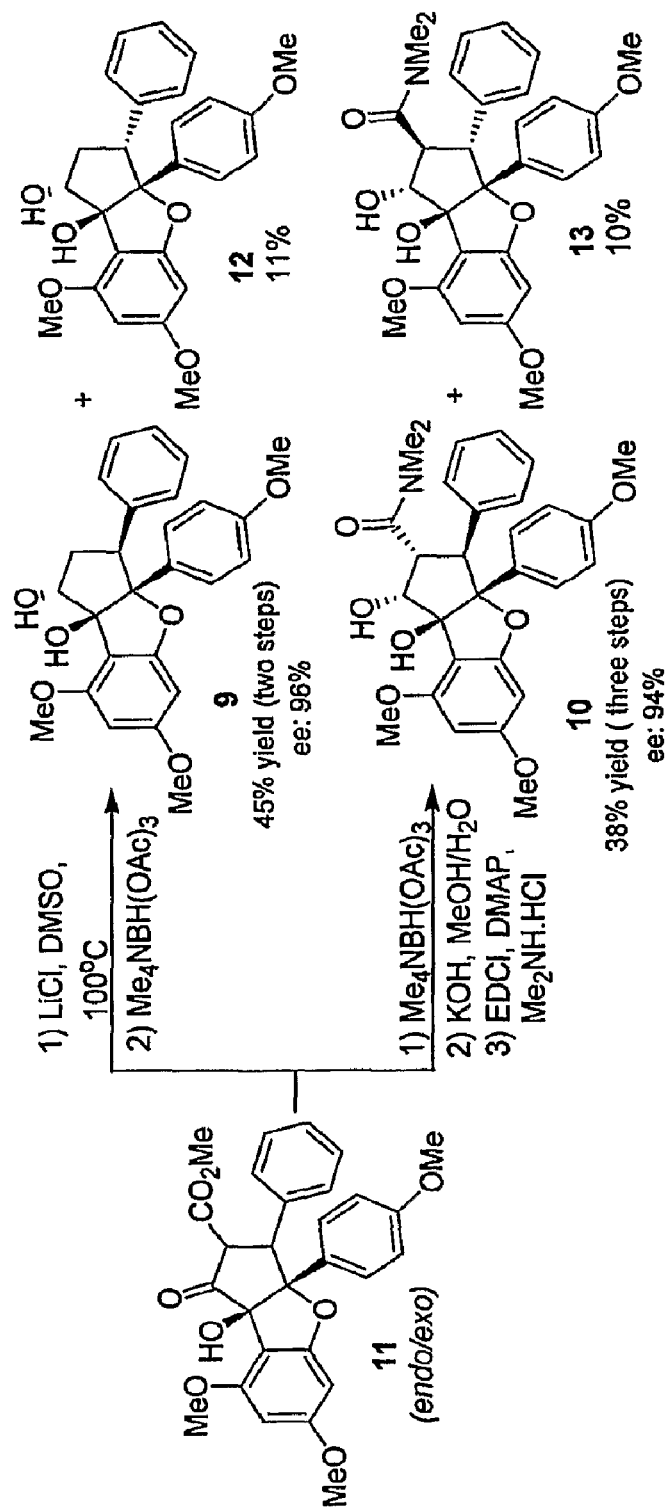

FIG. 9 shows a scheme for the enantioselective synthesis of rocaglamide and rocaglaol according to the present invention.

Figure 10:
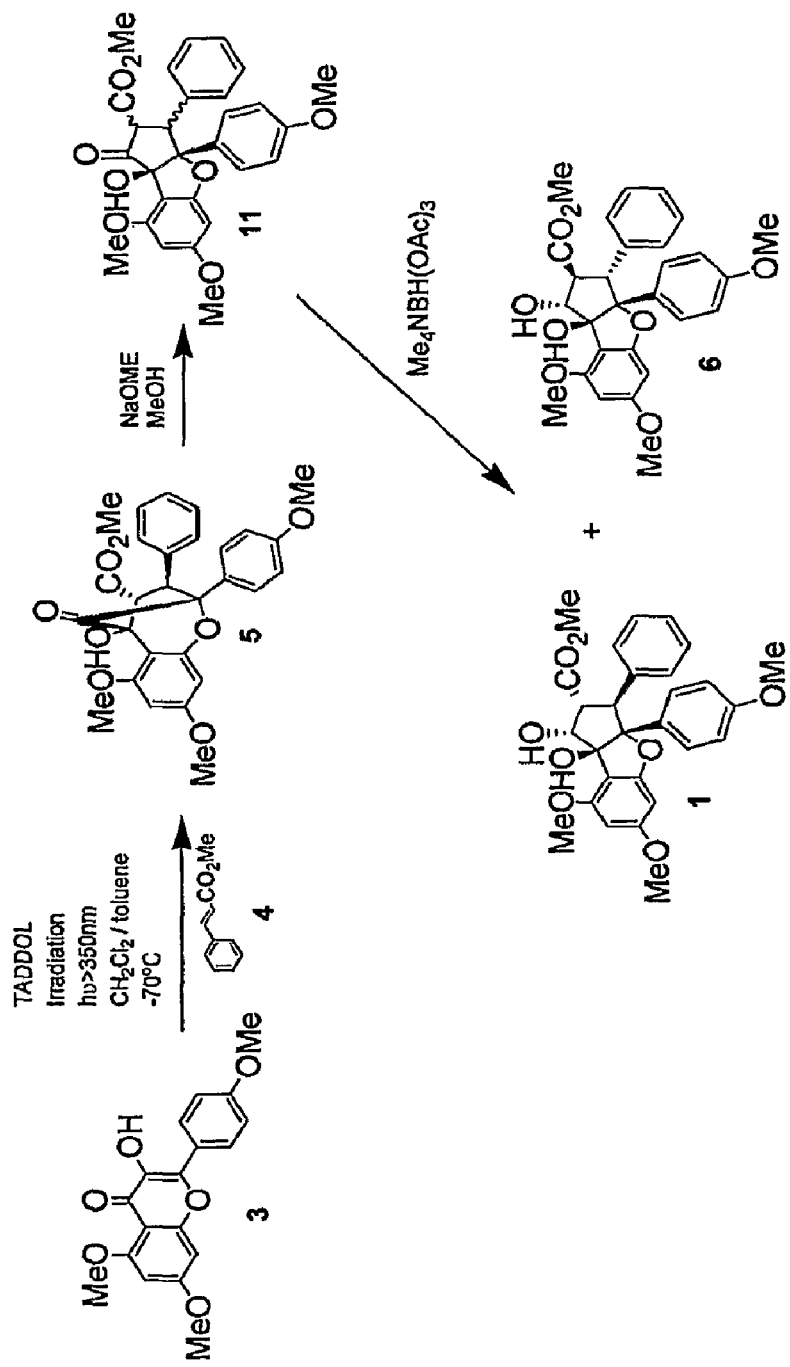

FIG. 10 shows a general reaction scheme for the enantioselective photocycloaddition reaction and preparation of methyl rocaglate according to the present invention.

Figure 11:
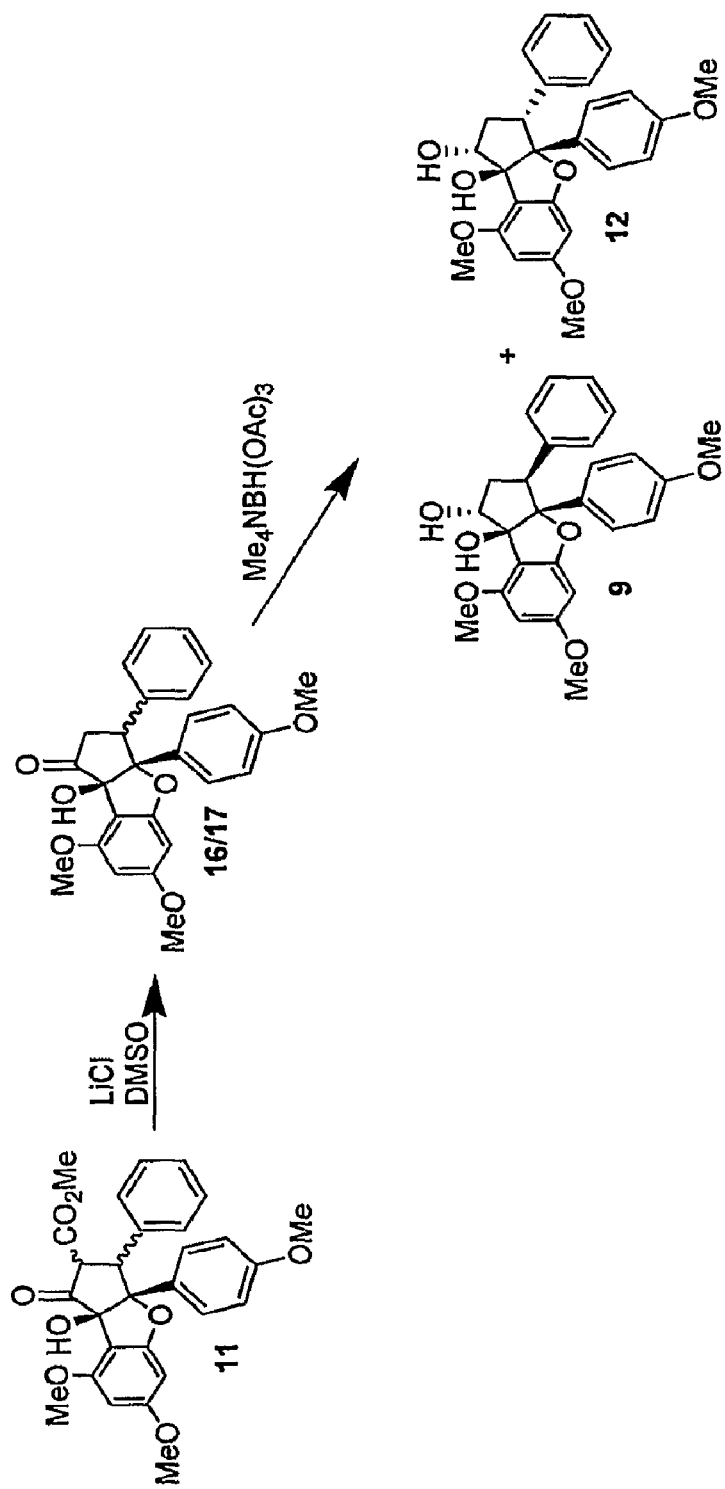

FIG. 11 shows a general reaction scheme for the preparation of rocaglaol according to the present invention.

Figure 12:
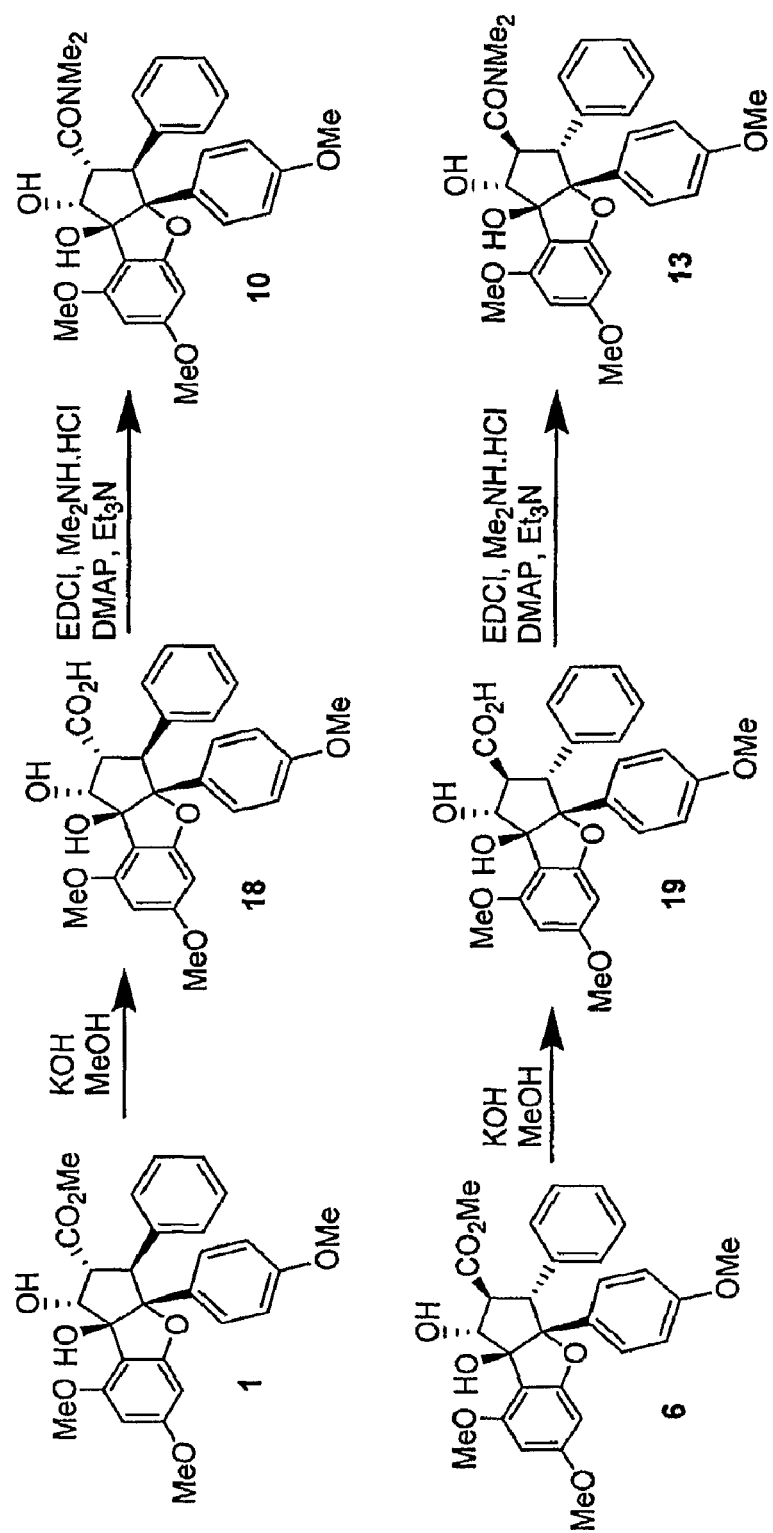

FIG. 12 shows a general reaction scheme for the preparation of rocaglamides according to the present invention.

FIG. 13(A) shows the X-ray crystal structure of compound 1, and FIG. 13(B) shows a unit cell representation of the centrosymmetric racemate 1.

FIG. 14 is a table presenting crystal data and structure refinement for compound 1.

FIG. 15(A) shows the X-ray crystal structure of compound 7d, and FIG. 15(B) shows the X-ray crystal structure of compound 7e.

FIG. 16 is a table presenting crystal data and structure refinement for compound 7d.

FIG. 17 is a table presenting crystal data and structure refinement for compound 7e.

FIG. 18 shows the IR spectrum of TADDOL derivatives (5 mM in $CH_2Cl_2$), (A) compound 7a, (B) compound 7b, (C) compound 7c, (D) compound 7d, (E) compound 7e, (F) compound 7f, (G) compound 7g, and (H) compound 7h.

DEFINITIONS

Throughout the specification, several terms are employed that are defined in the following paragraphs.

The term "chiral", as used herein to characterize a chemical compound, refers to a compound that contains an asymmetric center (chiral atom or chiral center) and thus can occur in two non-superimposable mirror-image forms (enantiomers).

The term "stereoisomers", as used herein, refers to compounds which have identical chemical constitution, but differ with regard to the arrangement of their atoms or groups in space.

The term "enantiomers", as used herein, refers to two stereoisomers of a compound which are non-superimposable mirror images of one another.

The term "enantioselective", when used herein to characterize a process, refers to a process which favors production of one of the two possible enantiomers of a reaction product. The process is said to produce an "enantioselectively-enriched product" when the yield of a particular enantiomer of the product is greater by a statistically significant amount relative to the yield of that enantiomer resulting from the same reaction run in the absence of a chiral catalyst. Enantioselectivity is generally quantified as "enantiomeric excess or ee" defined as follows: % Enantiomeric Excess A (ee)=(% Enantiomer A)−(% Enantiomer B), where A and B are the enantiomers formed. Additional terms that are used in conjunction with enantioselectivity include "optical purity" or "optical activity". An enantioselective reaction yields a product with an ee greater than zero. Preferred enantioselective reactions yield a product with an ee greater than about 5%, greater than about greater 10%, greater than about 30%, greater than about 40%, greater than about 50%, greater than about 60%, greater than about 70%, or greater than about 80%.

The term "catalytic amount" is recognized in the art and means a substoichiometric amount relative to a reactant. As used herein, a catalytic amount ranges from 0.0001 to 90 mole percent relative to a reactant, more preferably from 0.001 to 50 mole percent, still more preferably from 0.01 to 10 mole percent, and even more preferably from 0.1 to 5 mole percent relative to a reactant.

The term "non-racemic", when used herein in respect to a mixture of compounds, refers to a mixture of compounds having greater than 50% of a given enantiomer, more preferably at least 75%. The term "substantially non-racemic", when used herein in respect to a mixture of compounds, refers to a mixture of compounds having greater than 90% ee for a given enantiomer, more preferably greater than 95% ee.

As used herein, the term "Brønsted acid" refers to a chemical species which acts as a source of one or more protons, i.e., as a proton donor (see, for example, the McGraw-Hill Dictionary of Scientific and Technical Terms, 1984, $3^{rd}$ Ed., page 220; A. J. Gordon and R. A. Ford, "*The Chemists Companion*", 1972, Wiley: New York). Examples of Brønsted acids include, but are not limited to, carboxylic acid, sulfonic, and phosphoric acids.

The terms "oxidopyrylium species" and "oxidopyrylium ylide species" are used herein interchangeably. An oxidopyrylium species is a dipolar entity, i.e., an electrically neutral molecule carrying a positive charge and a negative charge in one of its major canonical descriptions. In the context of the present invention, an oxidopyrylium species preferably comprises the following chemical group/motif:

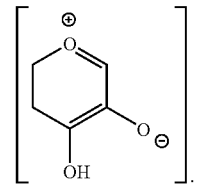

In certain embodiments of the present invention, preferred oxidopyrylium species have chemical structures ($I_T$) or ($II_T$). In many of the inventive methods provided herein, an oxidopyrylium species is photochemically generated and used as an intermediate in a chemical reaction.

The terms "photochemically generated" and "generated in a photochemical reaction" are used herein interchangeably to characterize a chemical entity whose formation is caused/initiated by absorption of ultraviolet, visible, or infrared radiation. Similarly, a chemical process or reaction is "photoinduced" if it is caused/initiated by absorption of ultraviolet, visible, or infrared radiation. A wide variety of chemical processes/reactions may be photoinduced including, but not limited to, additions, cyclizations, eliminations, enolizations, rearrangements, isomerizations, oxidations, reductions, substitutions, and the like.

As used herein, the term "intermediate" refers to a molecular entity with a lifetime appreciably longer than a molecular vibration that is formed (directly or indirectly) from one or more reactants and reacts further to give (either directly or indirectly) the product(s) of a chemical reaction.

The term "cycloaddition", as used herein, refers to a chemical reaction in which two or more π-electron systems (e.g., unsaturated molecules or different parts of the same unsaturated molecules) combine to form a cyclic product in which there is a net reduction of the bond multiplicity. In a cycloaddition, the π-electrons are used to form new σ bonds. The product of a cycloaddition is called an "adduct" or a "cycloadduct". Different types of cycloaddition are known in the art including, but not limited to, 1,3-dipolar cycloadditions and Diels-Alder reactions. When a cycloaddition is caused/initiated by ultraviolet, visible or infrared radiation, the cycloaddition is called a photocycloaddition.

As used herein, the term "converting" refers to a process or reaction that is aimed at modifying a chemical compound. A variety of processes or reactions can be used to convert or modify a chemical compound including, but not limited to, additions, eliminations, substitutions, oxidations, reductions, enolizations, rearrangements, isomerizations, and the like.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, the term "aliphatic" is intended herein to include, but is not limited to, alkyl, alkenyl, or alkynyl moieties. As used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms. "Lower alkenyl" and "lower alkynyl" respectively include corresponding 1-6 carbon moieties.

In certain embodiments, the alkyl, alkenyl and alkynyl groups employed in the invention contain 1-20; 2-20; 3-20; 4-20; 5-20; 6-20; 7-20 or 8-20 aliphatic carbon atoms. In certain other embodiments, the alkyl, alkenyl, and alkynyl groups employed in the invention contain 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl, alkenyl, and alkynyl groups employed in the invention contain 1-6; 2-6; 3-6; 4-6 or 5-6 aliphatic carbon atoms. In yet other embodiments, the alkyl, alkenyl, and alkynyl groups employed in the invention contain 1-4; 2-4 or 3-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include, but are not limited to, monocyclic, or polycyclic aliphatic hydrocarbons and bridged cycloalkyl compounds, which are optionally substituted with one or more functional groups. As will be appreciated by one of ordinary skill in the art, the term "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl, cyclohexyl, —CH$_2$-cyclohexyl, cyclohexenylethyl, cyclohexanylethyl, norborbyl moieties and the like, which again, may bear one or more substituents.

The term "alkoxy" or "alkyloxy", as used herein refers to a saturated (i.e., O-alkyl) or unsaturated (i.e., O-alkenyl and O-alkynyl) group attached to the parent molecular moiety through an oxygen atom. In certain embodiments, the alkyl group contains 1-20; 2-20; 3-20; 4-20; 5-20; 6-20; 7-20 or 8-20 aliphatic carbon atoms. In certain other embodiments, the alkyl group contains 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl group contains 1-6; 2-6; 3-6; 4-6 or 5-6 aliphatic carbon atoms. In yet other embodiments, the alkyl group contains 1-4; 2-4 or 3-4 aliphatic carbon atoms. Examples of alkoxy groups, include but are not limited to, methoxy, ethoxy, propoxy, isopropoxy, n-butoxy, i-butoxy, sec-butoxy, tert-butoxy, neo-pentoxy, n-hexoxy and the like.

The term "thioalkyl", as used herein, refers to a saturated (i.e., S-alkyl) or unsaturated (i.e., S-alkenyl and S-alkynyl) group attached to the parent molecular moiety through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of thioalkyl groups include, but are not limited to, methylthio, ethylthio, propylthio, isopropylthio, n-butylthio, and the like.

The term "alkylamino" refers to a group having the structure —NHR$_a$ wherein R$_a$ is aliphatic or alicyclic, as defined herein. The term "amino alkyl" refers to a group having the structure NH$_2$R$_a$—, wherein R$_a$ is aliphatic or alicyclic, as defined herein. In certain embodiments, the aliphatic or alicyclic group contains 1-20 aliphatic carbon atoms. In certain other embodiments, the aliphatic or alicyclic group contains 1-10 aliphatic carbon atoms. In still other embodiments, the aliphatic or alicyclic group contains 1-6 aliphatic carbon atoms. In yet other embodiments, the aliphatic or alicyclic group contains 1-4 aliphatic carbon atoms. In yet other embodiments, R$_a$ is an alkyl, alkenyl, or alkynyl group containing 1-8 aliphatic carbon atoms. Examples of alkylamino groups include, but are not limited to, methylamino, ethylamino, iso-propylamino and the like.

Some examples of substituents (or functional groups) of the above-described aliphatic (and other) moieties of compounds of the invention include, but are not limited to aliphatic, alicyclic, heteroaliphatic, heterocyclic, aromatic, heteroaromatic, aryl, heteroaryl, alkylaryl, heteroalkylaryl, alkylheteroaryl, heteroalkylheteroaryl, alkoxy, aryloxy, heteroalkoxy, heteroaryloxy, alkylthio, arylthio, heteroalkylthio, heteroarylthio, F, Cl, Br, I, —OH, —NO$_2$, —CN, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, —C(=O)R$_x$, —CO$_2$(R$_x$), —C(=O)N(R$_x$)$_2$, —OC(=O)R$_x$, —OCO$_2$R$_x$, —OC(=O)N(R$_x$)$_2$, —N(R$_x$)$_2$, —OR$_x$, —SR$_x$, —S(O)R$_x$, —S(O)$_2$R$_x$, —NR$_x$(CO)R$_x$, —N(R$_x$)CO$_2$R$_x$, —N(R$_x$)S(O)$_2$R$_x$, —N(R$_x$)C(=O)N(R$_x$)$_2$, —S(O)$_2$N(R$_x$)$_2$, wherein each occurrence of R$_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl groups described above and herein may be substituted or unsubstituted, branched or unbranched, saturated or unsaturated, and wherein any of the aryl or heteroaryl substituents described above and herein may be substituted or unsubstituted.

In general, the term "aromatic moiety" or "aromatic", as used herein, refers to a stable mono- or poly-cyclic, unsaturated moiety having preferably 3-14 carbon atoms, each of which may be substituted or unsubstituted. In certain embodiments, the term "aromatic moiety" refers to a planar ring having π-orbitals perpendicular to the plane of the ring at each ring atom and satisfying the Huckel rule where the number of π electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaromatic", as used herein, refers to a stable mono- or polycyclic, unsaturated moiety having preferably 3-14 carbon atoms, each of which may be substituted or unsubstituted; and comprising at least one heteroatom selected from O, S and N within the ring (i.e., in place of a ring carbon atom). In certain embodiments, the term "heteroaromatic moiety" refers to a planar ring comprising at least one heteroatom, having π-orbitals perpendicular to the plane of the ring at each ring atom, and satisfying the Huckel rule where the number of π electrons in the ring is (4n+2) wherein n is an integer.

It will also be appreciated that aromatic and heteroaromatic moieties, as defined herein may be attached via an alkyl or heteroalkyl moiety and thus also include -(alkyl)aromatic, -(heteroalkyl)aromatic, -(heteroalkyl)heteroaromatic, and -(heteroalkyl)-heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl) hetero-aromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, the term "aryl" refers to a mono- or bicyclic carbocyclic ring system having one or two aromatic rings including, but not limited to, phenyl, naphthyl, tetrahydronaphthyl, indanyl, indenyl and the like.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon atoms, the radical being joined to the rest of the molecule via any of the ring atoms, such as, for example, pyridyl, pyrazinyl, pyrimidinyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more substituents. Suitable substituents include, but are not limited to, any of the previously mentioned substituents, i.e., the substituents recited for aliphatic moieties, or for other moieties as disclosed herein, resulting in the formation of a stable compound.

The term "cycloalkyl", as used herein, refers specifically to groups having three to seven, preferably three to ten carbon atoms. Suitable cycloalkyls include, but are not limited to, cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with any of the previously mentioned substituents.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more of the previously mentioned substituents.

The term "heterocycloalkyl", "heterocycle" or "heterocyclic", as used herein, refers to compounds which combine the properties of heteroaliphatic and cyclic compounds and include, but are not limited to, saturated and unsaturated mono- or polycyclic cyclic ring systems having 5-16 atoms wherein at least one ring atom is a heteroatom selected from O, S and N (wherein the nitrogen and sulfur heteroatoms may optionally be oxidized), wherein the ring systems are optionally substituted with one or more functional groups, as defined herein. In certain embodiments, the term "heterocycloalkyl", "heterocycle" or "heterocyclic" refers to a non-aromatic 5-, 6- or 7-membered ring or a polycyclic group wherein at least one ring atom is a heteroatom selected from O, S and N (wherein the nitrogen and sulfur heteroatoms may optionally be oxidized), including, but not limited to, a bi- or tri-cyclic group, comprising fused six-membered rings having between one and three heteroatoms independently selected from oxygen, sulfur and nitrogen, wherein (i) each 5-membered ring has 0 to 2 double bonds, each 6-membered ring has 0 to 2 double bonds and each 7-membered ring has 0 to 3 double bonds, (ii) the nitrogen and sulfur heteroatoms may optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, pyrazolyl, imidazolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. The term "heterocycle, or heterocycloalkyl or heterocyclic" also encompasses heterocycle, or heterocycloalkyl or heterocyclic groups that are substituted by the independent replacement of one, two or three of the hydrogen atoms thereon with any of the previously mentioned substituents. Additionally, it will be appreciated that any of the alicyclic or heterocyclic moieties described above and herein may comprise an aryl or heteroaryl moiety fused thereto.

The terms "halo" and "halogen", as used herein, refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "amino", as used herein, refers to a primary (—$NH_2$), secondary (—$NHR_x$), tertiary (—$NR_xR_y$) or quaternary (—$N^+R_xR_yR_z$) amine, where $R_x$, $R_y$ and $R_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "acyl", as used herein, refers to a group having the general formula —C(=O)R$_b$, where R$_b$ is an aliphatic, alicyclic, heteroaliphatic, heterocyclic, aromatic or heteroaromatic moiety, as defined herein.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like encompass both substituted and unsubstituted groups.

By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen and carbon protecting groups may be utilized. For example, oxygen protecting groups include, but are not limited to, methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. Nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. It will be appreciated that the present invention is not intended to be limited to these protecting groups; rather, a variety of additional equivalent protecting groups can be readily identified using the above criteria and utilized in the present invention. Additionally, a variety of protecting groups are described in "*Protective Groups in Organic Synthesis*" T. W. Greene and P. G. Wuts (Eds.), John Wiley & Sons: New York, 1999 (3$^{rd}$ Ed), the entire contents of which are incorporated herein by reference.

As used herein, the term "medicament" refers to any substance or combination of substances that has a beneficial and/or therapeutic effect. In certain embodiments of the present invention, the manufacture of a medicament comprises the use of at least one derivative of the rocaglamide/aglain/forbaglin family prepared by methods provided herein. For example, a medicament according to the present invention may comprise one or more derivatives of the rocaglamide natural product family as active ingredient(s). A medicament may further comprise one or more other active ingredients, such as drugs or therapeutic agents known in the art or newly discovered agents whose activity is to be tested, and/or one or more pharmaceutically acceptable carriers.

As used herein, the term "pharmaceutically acceptable carrier" refers to a carrier medium which does not interfere with the effectiveness of the biological activity of the active ingredient(s) and which is not excessively toxic to the hosts at the concentrations at which it is administered. The term includes solvents, dispersion media, coatings, antibacterial and antifungal agents, isotonic agents, absorption delaying agents, and the like. The use of such media and agents for pharmaceutically active substances is well known in the art (see, for example, Remington's Pharmaceutical Sciences, E. W. Martin, 18$^{th}$ Ed., 1990, Mack Publishing Co.: Easton, Pa.).

The term "treatment" is used herein to characterize a method or process that is aimed at (1) delaying or preventing the onset of a disease or condition; or (2) slowing down or stopping the progression, aggravation, or deterioration of the symptoms of the disease or condition; or (3) bringing about ameliorations of the symptoms of the disease or condition; or (4) curing the disease or condition. The treatment may be administered prior to the onset of the disease, for a prophylactic or preventive action. Alternatively or additionally, the treatment may be administered after initiation of the disease or condition, for a therapeutic action.

DETAILED DESCRIPTION OF CERTAIN PREFERRED EMBODIMENTS

Figure 4:
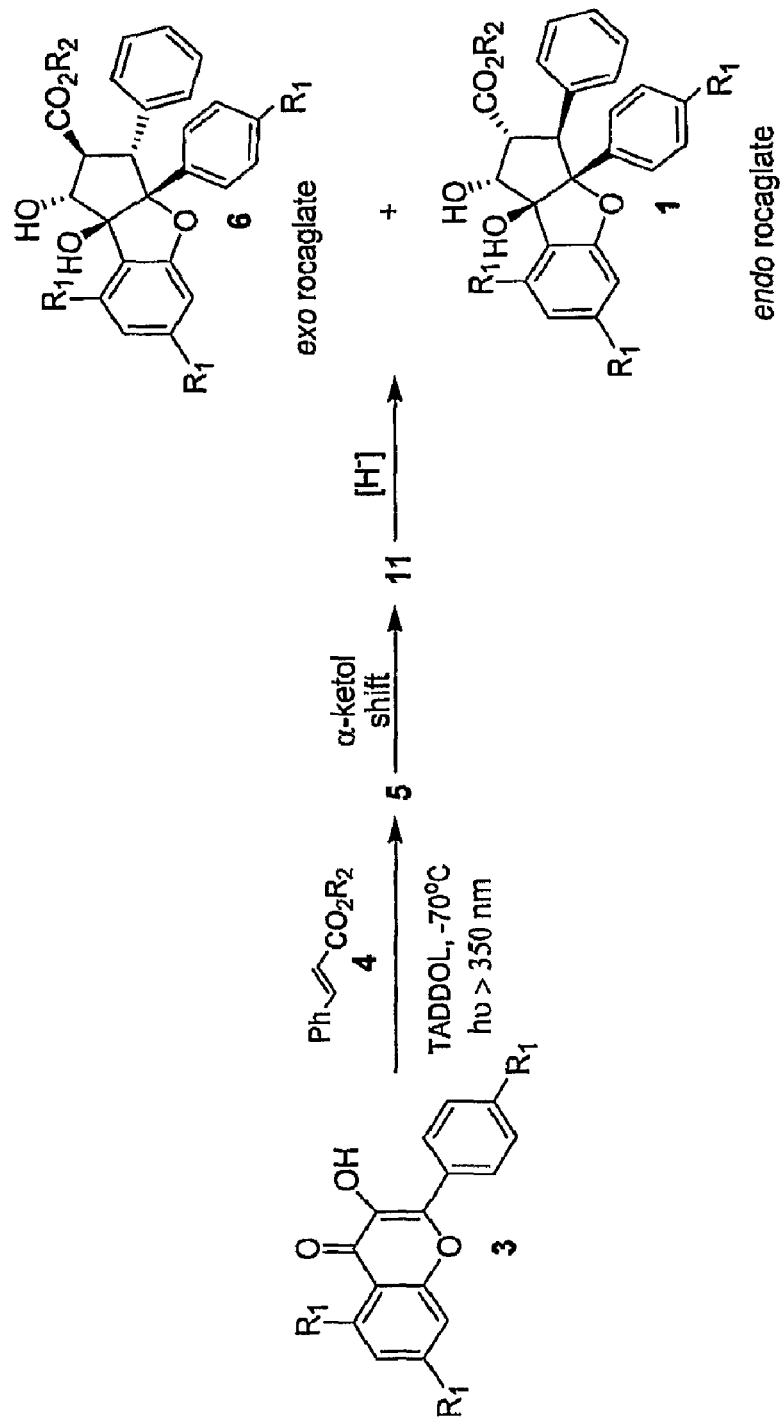
FIG. 4 shows an embodiment of the inventive synthetic approach to the formation of rocaglamides.

The present invention relates to a new strategy to the synthesis of rocaglamides and related aglains and forbaglins. In particular, the present invention provides a new synthetic approach for the preparation of chiral, nonracemic rocaglate derivatives. An embodiment of this new approach is outlined in FIG. 4.

Generally, the inventive synthetic methods involves enantioselective [3+2] photocycloaddition mediated by a functionalized TADDOL derivative, used as a chiral Brønsted acid. More specifically, as exemplified on FIG. 4, an inventive synthetic method generally includes photochemical generation of an oxidopyrylium species (compound 2) via excited state intramolecular protein transfer (ESIPT) of a 3-hydroxyflavone derivative 3 followed by 1,3-dipolar cycloaddition (i.e., [3+2]cycloaddition) of the oxidopyrylium species to a dipolarophile, such as a cinnamate derivative (compound 4), in the presence of a functionalized TADDOL derivative. This reaction results in the formation of the adduct 5, which contains an aglain core structure. Core structure 5 can be converted to the hydrorocaglate derivative 11 by α-ketol (acyloin) rearrangement; and hydroxyl-directed reduction of 11 affords the endo 1 and exo 6 rocaglate derivatives.

I. Excited State Intramolecular Proton Transfer (ESIPT)

An ESIPT phenomenon involves a very fast intramolecular transfer of a proton. In some cases, this process takes place in only tens or hundreds of femtoseconds (M. Kasha, J. Chem. Soc. Faraday Trans. 2, 1986, 82: 2379-2392; B. J. Schwartz et al., J. Phys. Chem., 1992, 96: 3591-3598; F. Laermer et al., Chem. Phys. Lett., 1988, 148: 119-124).

Literature reports have documented excited state intramolecular proton transfer (see, for example, P.-T. Chou, J. Chin. Chem. Soc., 2001, 48: 651-682; A. D. Roschal et al., J. Phys. Chem. A, 1998, 102: 5907-5914; A. Bader et al., J. Phys. Chem. A, 2002, 106: 2844-2849 and references therein; A. Samanta et al., J. Phys. Chem. A, 2003; 107: 6334-6339; A. P. Demchenko, J. Phys. Chem. A, 2003, 107: 4211-4216; R. Rastogi et al., Spectrochem. Acta, Part A, 2001, 57: 299-308) of 3-hydroxyflavone derivatives leading to the formation of an oxidopyrylium species (J. Hendrickson and J. S. Farina, J.

Org. Chem., 1980, 45: 3359-3361; P. G. Sammes et al., J. Chem. Soc. Perkin Trans. I, 1983, 1261-1265; P. A. Wender et al., J. Am. Chem. Soc., 1997, 119: 12976-12977; J. E. Baldwin et al., Tetrahedron Lett., 2003; 44: 4543-4545).

Figure 5:
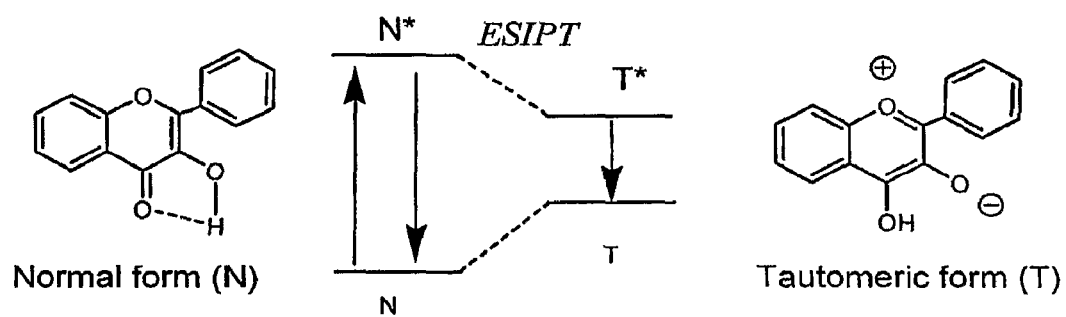
FIG. 5 is a scheme showing the excited state intramolecular proton transfer (ESIPT) process and fluorescence emission taking place upon photoirradiation of 3-hydroxyflavone.

The overall ESIPT process (shown on FIG. 5 in the case of the parent molecule, 3-hydroxyflavone, 3-HF) involves generation of a putative tautomeric form of 3-HF, where the proton of the hydroxy group at position C3 migrates to the ketone group at position C4 to give an oxidopyrylium species (tautomeric form T).

Although ESIPT processes of 3-HF derivatives have been reported in the literature to produce excited species such as the oxidopyrylium, there are no reports of chemical reactions using these species. The present invention encompasses the recognition by the Applicants that the reactivity of such oxidopyrylium species can be advantageously exploited in chemical reactions.

Accordingly, one aspect of the present invention relates to the use of photochemically generated oxidopyrylium species as intermediates in chemical reactions. Preferably, the oxidopyrylium species is photochemically generated via a process comprising an excited state intramolecular proton transfer.

As will be appreciated by one of ordinary skill in the art, any organic molecule which can produce an oxidopyrylium species upon photochemical excitation is suitable for use in the practice of the present invention. Particularly suitable compounds comprise a 5-hydroxyl-pyran-4-one group/motif, including, but not limited to, 5-hydroxy-2,3-dihydro-pyran-4-one derivatives, 3-hydroxychromone derivatives (M. Itoh, Pure and Applied Chemistry, 1993, 65: 1629-1634; A. S. Klymchenko et al., New J. Chem., 2004, 28: 687-692) and 3-hydroxyflavone derivatives. When the photochemically generated oxidopyrylium species is used in the preparation of rocaglamides and related aglains and forbaglins according to the new synthetic approach provided herein, the oxidopyrylium species is preferably generated by photochemical excitation of a 3-hydroxychromone derivative of chemical structure (I) or 3-hydroxyflavone derivative of chemical structure (II).

Methods for photochemically exciting organic molecules are known in the art. Procedures for the photochemical irradiation of 3-hydroxyflavone according to the present invention are described in the Examples section.

II. Cycladdition Reactivity of Oxidopyrylium Species

In certain methods of the present invention, the photochemically generated oxidopyrylium species is used as a reactive intermediate in a cycloaddition, such as a 1,3-dipolar cycloaddition. In certain preferred embodiments, the oxidopyrylium species is reacted with a dipolarophile in the presence of a functionalized TADDOL derivative. As already mentioned above, in the presence of a functionalized TADDOL derivative, the [3+2]cycloaddition is enantioselective.

Functionalized TADDOL Derivatives as Chiral Brønsted Acids

During studies toward the synthesis of (±)-methyl rocaglate (B. Gerard et al., J. Am. Chem. Soc., 2004, 126: 13620-13621) (see FIG. 3), the present Applicants found that the photochemical [3+2]cycloaddition required polar protic solvents, such as methanol, in order to proceed. It has been proposed that ESIPT may be enhanced in such solvents due to the formation of solvated complexes involving "double proton transfer" (D. Le Gourrierec et al., Prog. React. Kinet., 1994, 19: 211-275).

To access chiral, non-racemic rocaglate derivatives, the Applicants investigated the use of chiral Brønsted acids (N. T. McDougal and S. E. Schaus, J. Am. Chem. Soc., 2003, 125: 12094-12095; A. N. Thadani et al., Proc. Natl. Acad. Sci. U.S.A., 2004, 101: 5846-5850; B. N. Nugent et al., J. Am. Chem. Soc., 2004, 126: 3418-3419; H. Yamamoto et al., J. Am. Chem. Soc., 2005, 127: 1080-1081; V. Bhasker et al. Org. Lett., 2005, 7: 5657-5660; T. P. Yoon and E. N. Jacobsen, Angew. Chem., Int. Ed., 2005, 44: 466-468; M. S. Taylor et al., Angew. Chem., Int. Ed., 2006, 45: 1520-1543) in aprotic solvents as host-guest complexes (B. Grosch et al., Angew. Chem., Int. Ed., 2003, 42: 3693-3696; S. Legrand et al., Tetrahedron: Asymmetry, 2005, 16: 635-640; A. Bauer et al., Nature, 2005, 436: 1139-1140; K. Tanaka et al., Org. Lett., 2005, 7: 1501-1503; P. Wessig, Angew. Chem., Int. Ed., 2006, 45: 2168-2171) to mediate photochemical cycloaddition.

After screening a number of hydrogen-bonding additives, TADDOL reagents (N. T. McDougal and S. E. Schaus, J. Am. Chem. Soc., 2003, 125: 12094-12095; A. N. Thadani et al., Proc. Natl. Acad. Sci. U.S.A., 2004, 101: 5846-5850; B. N. Nugent et al., J. Am. Chem. Soc., 2004, 126: 3418-3419; H. Yamamoto et al., J. Am. Chem. Soc., 2005, 127: 1080-1081; V. Bhasker et al., Org. Lett., 2005, 7: 5657-5660; T. P. Yoon and E. N. Jacobsen, Angew. Chem., Int. Ed., 2005, 44: 466-468; M. S. Taylor et al., Angew. Chem., Int. Ed., 2006, 45: 1520-15435) were identified as chiral mediators. As shown in Table 1, photochemical cycloaddition of 3 (where $R_1$=OCH$_3$) with methyl cinnamate 4 (where $R_2$=CH$_3$) using 1-phenyl TADDOL 7a (1 equivalent) in toluene at 0° C. afforded a 24% overall yield and 7% ee of (−)-methyl rocaglate 1 (where $R_1$=OCH$_3$ and $R_2$=CH$_3$) after ketol shift and reduction (entry 2). Use of naphthyl TADDOL derivative 7b led to an increase in enantiomeric excess up to 25% (see entries 2 and 3 of Table 1). On the basis of optical rotation data, the use of TADDOL derivatives derived from L-tartrate was shown to favor the natural (−)-enantiomer 1.

The TADDOLs are a class of chiral ligands which have attracted considerable attention in the last two decades or so. They have been used for more than 20 years in asymmetric synthesis (D. Seebach et al., J. Org. Chem., 1995, 60: 1788; Dahinden et al in "*Encyclopedia of Reagents for Organic Synthesis*", Paquette, L. A., Ed.; John Wiley & Sons, Chichester, 1995; D. Seebach et al., Helv. Chim. Acta, 1997, 80: 2515; D. Seebach et al., Angew. Chem. Int. Ed., 2001, 40: 92-138; and references cited therein, each of which is incorporated herein by reference in its entirety) for a number of asymmetric reactions. TADDOLs are α,α,α',α'-tetraaryl-1,3-dioxolane-4,5-dimethanol derivatives, i.e., compounds that comprise two adjacent diarylhydroxymethyl groups in a trans relationship on a 1,3-dioxolane ring.

TADDOLs suitable for use in the present invention may be any of those known in the art (see, for example, include any of the D. Seebach et al., Angew. Chem. Int. Ed., 2001, 40: 92-138, and U.S. Pat. No. 6,099,751). A general chemical structure of TADDOLs suitable for use in the present invention is presented in FIG. 6(A). In this chemical structure, $R^1$ and $R^2$ may be identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —NO$_2$, —CN, —CF$_3$, —CH$_2$CF$_3$, —CHCl$_2$, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —OC(=O)N(R$_x$)$_2$, —OC(=O)R$_x$, —OCO$_2$R$_x$, —S(O)R$_x$, —S(O)$_2$R$_x$, —NR$_x$(CO)R$_x$, —N(R$_x$)CO$_2$R$_x$, —N(R$_x$)C(=O)N(R$_x$)$_2$, —N(R$_x$)S(O)$_2$R$_x$, and —S(O)$_2$N(R$_x$)$_2$, wherein each occurrence of R$_x$ is independently selected from the group consisting of hydrogen, aliphatic, alicyclic, heteroaliphatic, heterocyclic, aromatic, heteroaromatic, aryl, and heteroaryl. $Ar^1$, $Ar^2$, $Ar^3$, and $Ar^4$ may be identical or different and selected from the group consisting of substituted or unsubstituted aryloxy, heteroaryloxy, thioaryl, aryl, heteroaryl, arylamino, and amino aryl. TADDOLs suitable for use in the present invention may, alternatively, be dimeric TADDOLs, the general chemical structure of which is presented on FIG. 6(A). In this chemical structure, $Ar^1$, $Ar^2$, $Ar^3$, $Ar^4$ $Ar^{1'}$, $Ar^{2'}$, $Ar^{3'}$, and $Ar^{4'}$ may be identical or different and selected from the group consisting of substituted or unsubstituted aryloxy, heteroaryloxy, thioaryl, aryl, heteroaryl, arylamino, and amino aryl. Examples of aryl groups include, but are not limited to, phenyl, naphthyl, anthracenyl, phenanthrenyl, biphenylenyl, styryl, benzyl, naphthylmethyl, biphenyl, naphthyl-phenyl-, phenyl-naphthyl-, benzyloxyphenyl-, benzyloxy-naphthyl-, phenoxy-phenyl-, biphenyl-phenyl-, benzyloxy-biphenyl, and the like.

Methods for the synthesis of TADDOLs are known in the art (see, for example, Helvetica Chim. Acta, 1994, 77: 2071-2110; D. Seebach et al., J. Org. Chem., 1995, 60: 1788; and D. Seebach et al., Angew. Chem. Int. Ed., 2001, 40: 92-138). For example, TADDOLs can be prepared from acetals or ketals of tartrate esters by reaction of the latter with aromatic Grignard reagents. Procedures for the preparation of TADDOLs are described in the Examples section of the present application.

Structures of some of the TADDOL derivatives evaluated by the Applicants are presented on FIG. 6(B). The effect of temperature on the enantioselectivity of the [3+2] photocycloaddition (and subsequent α-ketol rearrangement/reduction sequence) was investigated. Results are presented in Table 1 and Table 2 (entries 2 and 4, and 3 and 5). A decrease in temperature was found to lead to a noticeable improvement in the enantioselectivity of the cycloaddition. Accordingly in certain preferred embodiments of the present invention, the [3+2]cycloaddition is performed at a temperature below 0° C., for example below about −10° C., below about −20° C., below about −30° C., below about −40° C., below about −50° C., below about −60° C., below about −70° C., below about −80° C., below about −90° C., or below about −100° C.

The TADDOL complexing agent could be recovered in high yield by precipitation from methanol. A control experiment involving addition of 7g and 5 equivalents of methanol (see entry 10 of Table 1) led to a loss of enantioselectivity presumably due to achiral background reactions promoted by the protic cosolvent (P. Quadrelli et al., Eur J. Org. Chem., 2002, 13: 2058-2065; G. Adembri et al., J. Chem. Res., 2003, 3: 126-127). Accordingly, in certain preferred embodiments of the present invention, the [3+2]cycloaddition is carried out in aprotic solvents or mixtures thereof. The term "aprotic", when used herein to characterize a solvent (or mixture of solvents), refers to a solvent that is unable to donate protons. Examples of aprotic solvents include, but are not limited to, hexane, toluene, pentane, cyclohexane, dioxane, carbon tetrachloride, benzene, carbon disulfide, toluene, diethyl ether, chloroform, ethyl acetate, tetrahydrofuran, methylene chloride ($CH_2Cl_2$), pyridine, dimethylformamide, acetonitrile, dimethylsulfoxide, and the like.

The effects of stoichiometry and concentrations on the enantioselectivity of the [3+2] photocycloaddition were also investigated. The results of these experiments are presented in Table 3.

The effects of the chemical structure of TADDOL derivatives on the [3+2] photocycloaddition enantioselectivity was then evaluated under identical conditions (at low temperature, i.e., −70° C.; and using a mixed solvent system, i.e., 2:1, toluene:$CH_2Cl_2$, to avoid low viscosity and poor substrate solubility). It was found that the nature of both the aryl substituent and acetal side chain was important for high enantioselectivity. Results of this experiment are presented in Table 1. For example, use of TADDOL derivative 7f, which bears a 9-phenanthrenyl substituent and a cyclohexyl acetal (entry 9) afforded 1 in 71% ee (53% overall yield). The highest enantioselectivity obtained in the experiments performed was achieved using dimeric TADDOL 8a (89% ee, entry 12) but low conversion was observed. Recrystallization of 1 obtained from using TADDOL 7g led to the formation of centrosymmetric racemate crystals (X. Lei et al., Angew. Chem., Int. Ed., 2003, 42: 2913-3917 and references therein) and isolation of 1 (94% ee, 86% recovery) from the mother liquor. Unexpectedly, when diphenyl TADDOL acetal (7e, entry 8 in Table 1) was employed as additive, methyl rocaglates 1 and 6 were obtained as racemates. X-ray crystal structure analysis of 7e showed the presence of a TADDOL conformer (J. Irurre et al., Tetrahedron: Asymmetry, 1992, 3: 1591-1596) involving intramolecular H-bonding between the hydroxyl groups and the π system of the phenanthrene ring. The relevance of this conformer in solution was further confirmed by infrared spectroscopy (FIG. 7), in which the hydroxyl stretching frequencies corresponding to intramolecular hydrogen bonding between the two hydroxyl groups (additive 7g) (A. K. Beck et al., Chimia, 1991, 45: 238-244; D. Seebach et al., J. Org. Chem., 1995, 60: 1788-1799) are red-shifted in comparison to frequencies for the weakly hydrogen-bonded additive 7e.

Without wishing to be bound by any particular theory, it is noted that one possible explanation for the enantioselectivity observed in the [3+2] photocycloaddition in the presence of a TADDOL derivative is an assembly involving the oxidopyrylium species 2 and TADDOL 7g (FIG. 8). The well-defined arrangement of TADDOL may form a hydrogen bond with the oxidopyrylium via its free hydroxyl group, which may stabilize the dipole (X. Lei et al., Angew. Chem., Int. Ed., 2003, 42: 2913-3917 and references therein). A computational study (B3LYP/6-31+G*) (P. Quadrelli et al., Eur J. Org. Chem., 2002, 13: 2058-2065; G. Adembri et al., J. Chem. Res., 2003, 3: 126-127) of the oxidopyrylium intermediate indicated a high degree of electron density on the phenoxide oxygen, suggesting this site as a strong point of interaction for hydrogen bonding. The stereofacial approach of the dipolarophile may be controlled by shielding of the aryl group at the pseudoequatorial position of the seven-membered ring formed by an intramolecular H-bond between the two hydroxyl groups (N. T. McDougal and S. E. Schaus, J. Am. Chem. Soc., 2003, 125: 12094-12095).

Conversion of the Cycloadduct 5

Figure 3:
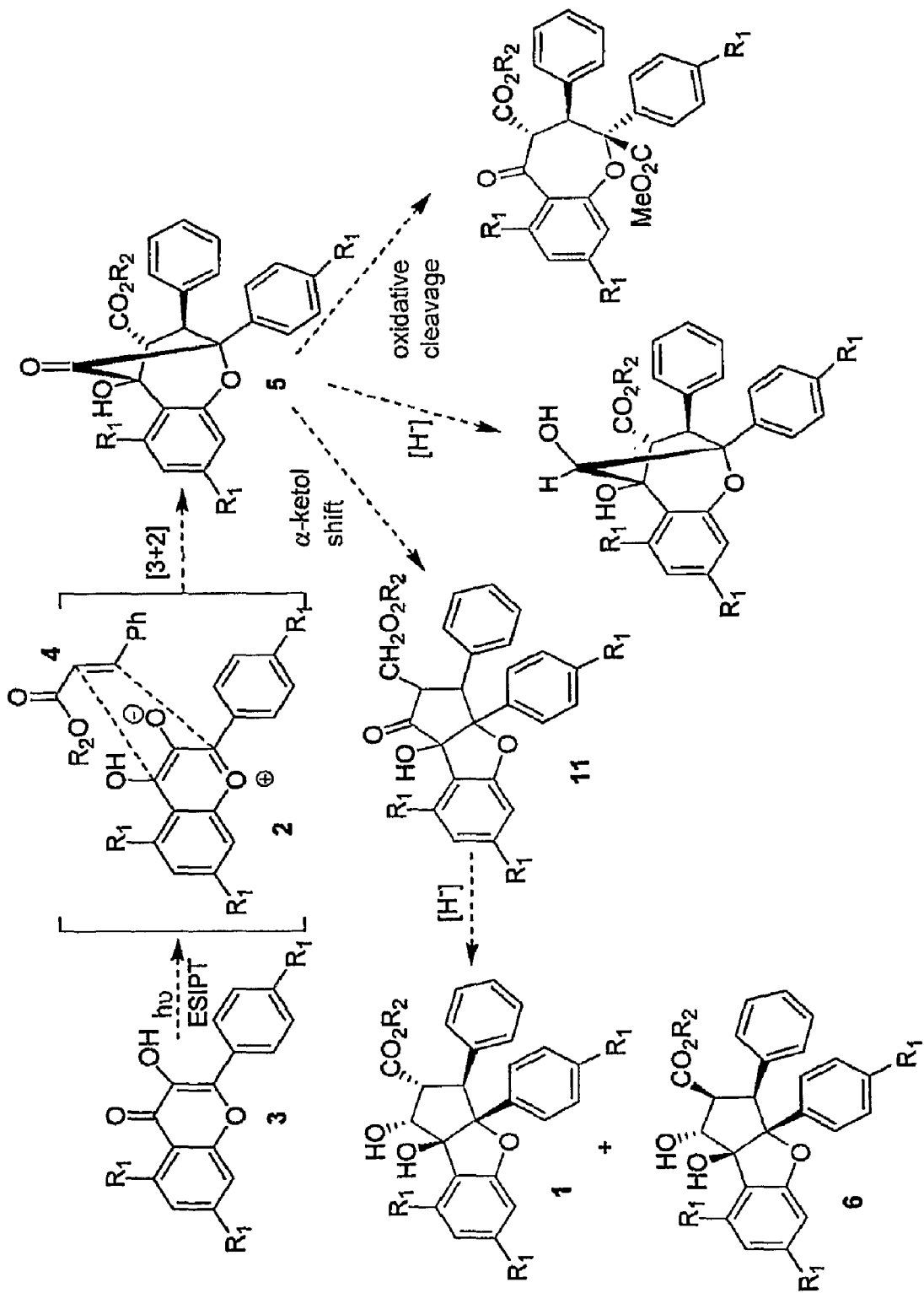
FIG. 3 shows a general reaction scheme designed and developed by the present Applicants (3. Gerard et al., J. Am. Chem. Soc., 2004, 126: 13620-13621; and International Application WO 2005/092876) for the synthesis of rocaglamide natural products.

As shown on FIG. 3, photocycloadduct 5, which contains an aglain core system, can be converted to compounds containing rocaglamide and forbaglin ring systems.

For example, the aglain core structure of cycloadduct 5 can be converted to dehydrorocaglate by α-ketol (acyloin) rearrangement (L. A. Paquette and J. E. Hofferberth, Org. React., 2003, 62: 477-567; for ketol shifts in biogenesis, see, for example, M. Rentzea and E. Hecker, Tetrahedron Lett., 1982, 23: 1785-1788; and D. H. G. Crout and D. L. Rathbone, J. Chem. Soc. Chem. Commun., 1987, 290-291).

Attempted thermal acyloin rearrangement (J. Lui et al., Tetrahedron, 1998, 54: 11637-11650) of compound 5 did not afford any observable ketol shift product. Acyloin rearrangements have alternatively been conducted using acidic or basic conditions or employing metal catalysis and have been used with success in a number of natural product syntheses (for K252a, see, for example, K. Tamaki et al., Tetrahedron Lett., 2002, 43: 379-382; for Taxanes, see, for example, L. Paquette and J. E. Hofferberth, J. Org. Chem., 2003, 68: 2266-2275). Treatment of cycloadduct 5 with protic or Lewis acidic conditions ($BF_3$, $Et_2O$, $ZnCl_2$) resulted in decomposition of the starting material. However, treatment of cycloadduct 5 under basic conditions (2.5 equivalents of NaOMe, methanol) (X. Creary et al., J. Org. Chem., 1985, 50: 1932-1938), afforded compound 11. The success of basic conditions for α-ketol rearrangement may be explained by the fact that such basic conditions favor the formation of the enolate, which may drive the ketol shift equilibrium (E. Piers et al., Synlett., 1999, 7: 1082-1084) towards the rocaglamide core.

Using optimized conditions for enantioselective photocycloaddition (entry 11), the synthesis of the natural products rocaglaol 9 and rocaglamide 10 (B. M. Trost et al., J. Am. Chem. Soc., 1990, 112: 9022-9024) was achieved (see FIG. 9 and Examples section) using compound 11 as starting material. By using 4 as dipolarophile and 7g as additive, rocaglaol 9 was obtained in 96% ee after decarboxylation (A. E. Greene et al., Tetrahedron Lett., 1976, 2707-2708) and reduction of intermediate 11 (N. Diedrichs et al., Eur J. Org. Chem., 2005, 9: 1731-1735). Rocaglamide 10 could also be accessed from 11 via reduction, hydrolysis, and amide bond formation (94% ee).

Cycloadduct 5 can also be converted to compounds containing a forbaglin ring system (see B. Gerard et al., J. Am. Chem. Soc., 2004, 126: 13620-13621; and International Application WO 2005/092876). Oxidative cleavage of the aglain core to the forbaglin ring system may be conducted, for example, using Pb(OAc)$_4$ (E. Baer, J. Am. Chem. Soc., 1940, 62: 1597-1606).

III. Chemical Modifications of Aglain/Rocaglamide/Forbaglin Derivatives

As will be appreciated by those of ordinary skill in the art, initially formed aglain derivatives as well as the forbaglins and rocaglamides derived from them can be further chemically modified to obtain new derivatives of the aglain/rocaglamide/forbaglin family.

For example, chemical modifications may be performed to study structure-activity relationships with the goal of developing compounds that possess improved biological activity and that fulfill all stereoelectronic, physicochemical, pharmacokinetic, and toxicologic factors required for clinical usefulness. In such studies, molecular structure and biological activity are correlated by observing the results of systemic structural modification on defined biological endpoints. For example, comparison of the activity of structurally-related compounds may help identify positions and/or chemical motifs that play an important role in biological activity. Similarly, analysis of the effects of the stereochemistry (i.e., the arrangement of atoms in space) of these chemically modified compounds on biological endpoints may help identify conformations that are favorable to the biological activity. The present invention is intended to encompass chemically modified derivatives of the aglain/rocaglamide/forbaglin family obtained by the methods disclosed herein.

IV. Uses of Aglain/Rocaglamide/Forbaglin Derivatives

As mentioned above, compounds in the rocaglamide/aglain/forbaglin family have been demonstrated to exhibit biological activity. In particular, a number of these compounds are potent natural insecticides (B. W. Nugroho et al., Phytochemistry, 1997, 45: 1579-1585; B. W. Gussregen et al., Phytochemistry, 1997, 44: 1455-1461; G. Brader et al., J. Nat. Prod., 1998, 61: 1482-1490; J. Hiort Chaidir et al., Phytochemistry, 1999, 52: 837-842; B. W. Nugrobo et al., Phytochemistry, 1999, 51: 367-376).

Figure 1:
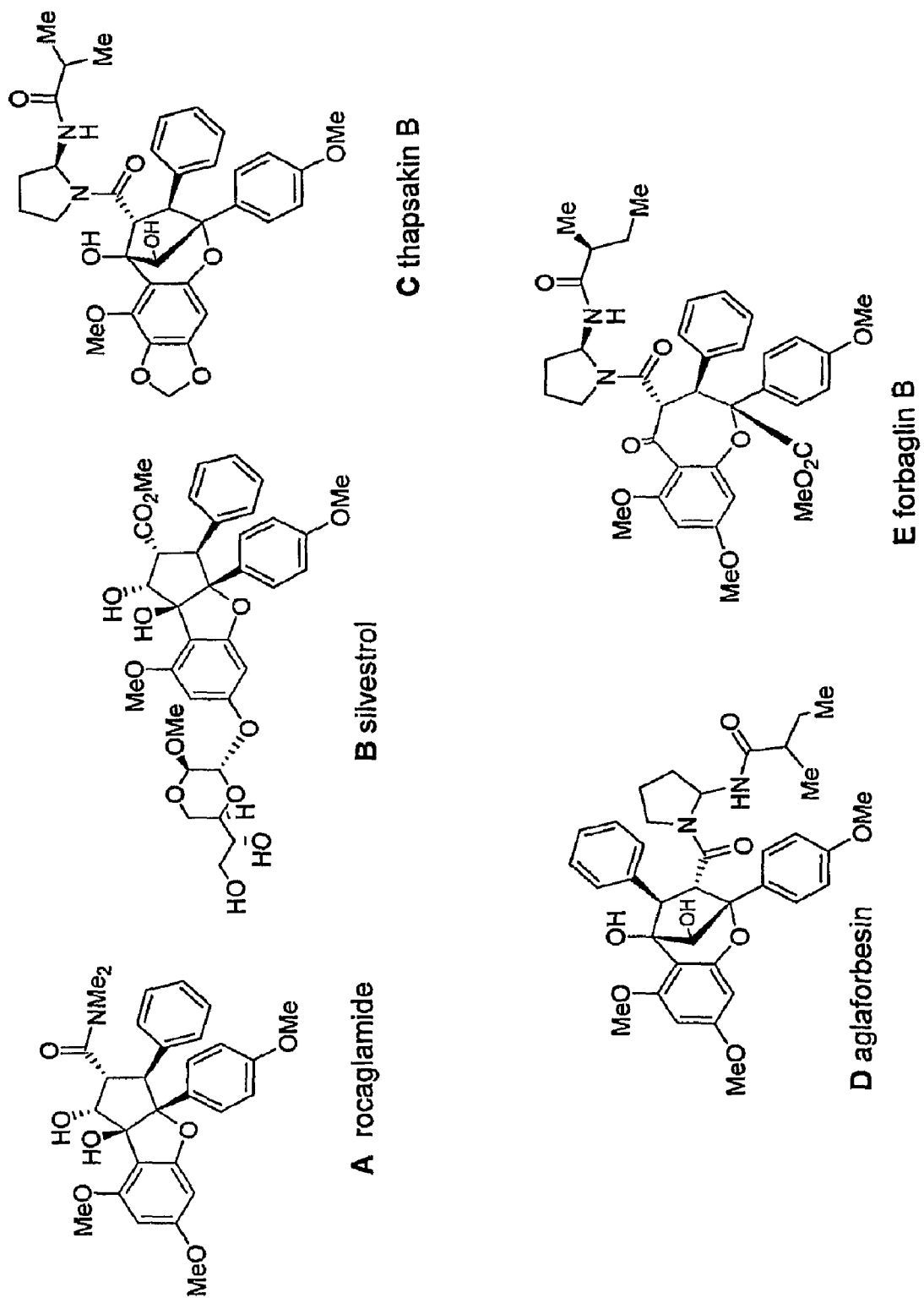
FIG. 1 shows the chemical structures of Rocaglamide and related natural compounds isolated from the plant genus *Aglaia*.
Figure 2:
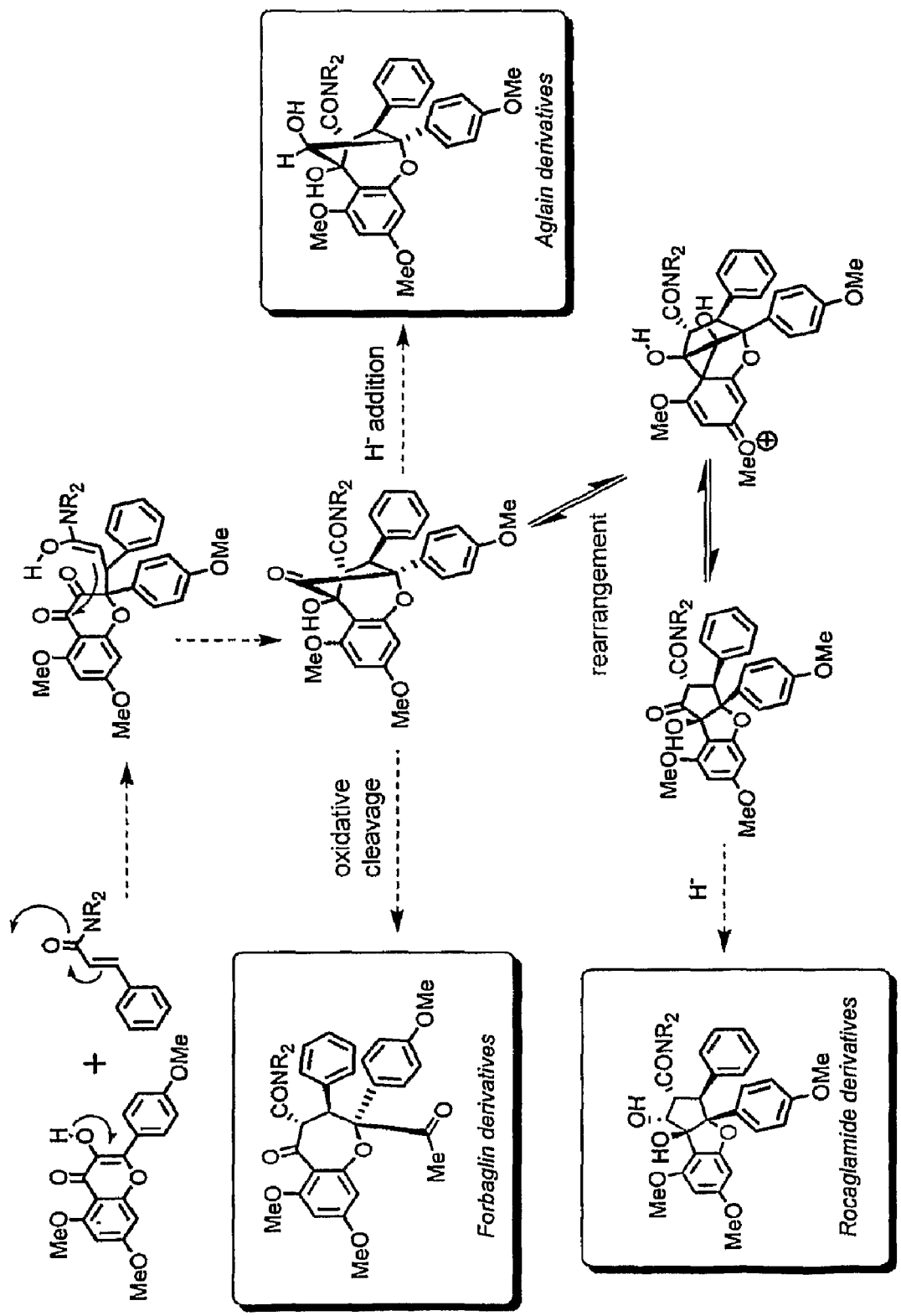
FIG. 2 shows a reaction scheme proposed by Proksch and coworkers (Curr. Org. Chem., 2001, 5: 923-938) for the biosynthetic preparation of rocaglamides.

Moreover, rocaglamide derivatives have been found to exhibit cytostatic activity in human cancer cell lines (B. Cui et al, Tetrahedron, 1997, 53: 17625-17632; T. S. Wu et al., J. Nat. Prod., 1997, 60: 606-608; S. K, Lee et al., Chem. Biol. Interact., 1998, 115: 215-228) with effects comparable to those observed with established drugs such as vinblastine sulfate and actinomycin D (F. I. Bohnenstengel et al., Z. Naturforsch. [C], 1999, 54: 55-60; F. I. Bohnenstengel et al., Z. Naturforsch. [C], 1999, 54: 1075-1083). In particular, the rocaglate silvestrol B (see FIG. 1) has been shown to display cytotoxic activity against human cancer cells comparable to the anticancer drug TAXOL® (B. Y. Hwang et al., J. Org. Chem., 2004, 69: 3350-3358). Experimental results reported in that study suggest that it induces apoptosis at nanomolar concentrations in colorectal tumor cell lines (Hausott et al., Int. J. Cancer, 2004, 109: 933-940). Furthermore, rocaglamides have been demonstrated to block protein biosynthesis (T. Ohse et al., J. Nat. Prod., 1996, 650-653) and to induce growth arrest in the G2/M phase in certain tumor cells (F. I. Bohnenstengel et al., Z. Naturforsch. [C], 1999, 54: 1075-1083).

More recently, it was shown that rocaglamides represent highly potent and specific inhibitors of TNF-α (tumor necrosis factor-alpha) and PMA (porbol 12-myristate 13 acetate)-induced NF-κB (nuclear factor-kappa B) activity in different mouse and human T cell lines. The $IC_{50}$ values observed for rocaglamide derivatives were in the nanomolar range whereas aglain derivatives proved inactive. Rocaglamide and several of its derivatives are among the strongest inhibitors of NF-κB induced gene activation known so far (B. Baumann et al., J. Biol. Chem., 2002, 277: 44791-44800).

Agents that can suppress NF-κB activation have, in principle, the potential to prevent or delay the onset of or treat NF-κB linked diseases. On activation, NF-κB induces the expression of more than 200 genes, that have been shown to suppress apoptosis, induce cellular transformation, proliferation, invasion, metastasis, chemoresistance, radioresistance, and inflammation (A. Garg and B. B. Aggarwal, Leukemia, 2002, 16: 1053-1056). The activated form of NF-κB has been found to mediate cancer (A. Garg and B. B. Aggarwal, Leukemia, 2002, 16: 1053-1056; A Lin and M. Karin, Semin. Cancer Biol., 2003, 13: 107-114; R. Z. Orlowski and A. S. Baldwin, Trends Mol. Med., 2002, 8: 385-389), artherosclerosis (G. Valen et al., J. Am. Coll. Cardiol., 2001, 38: 307-314), myocardial infraction (W. K. Jones et al., Cardiovasc. Toxicol., 2003, 3: 229-254), diabetes (S. E. Shoelson et al., Int. J. Obes. Relat. Metab. Disord., 2003, 27 (Suppl. 3): S49-52), allergies (L. Yang et al., J. Exp. Med., 1998, 188: 1739-1750; J. Das et al., Nature Immunol., 2001, 2: 45-50), asthma (R. Gagliardo et al., Am. J. Respir. Crit. Care Med., 2003, 168: 1190-1198), arthritis (A. K. Roshak et al., Curr. Opin. Pharmacol., 2002, 2: 316-321), Crohn's disease (D. A. van Heel et al., Hum. Mol. Genet., 2002, 11: 1281-1289), multiple sclerosis (C. J. Huang et al., Int. J. Dev. Neurosci., 2002, 20: 289-296), Alzheimer's disease (M. P. Mattson and S. Camandola, J. Clin. Invest., 2001, 107: 247-254; B. Kaltschmidt et al., Proc. Natl. Acad. Sci. USA, 1997, 94: 2642-2647), osteoporosis, psoriasis, septic shock, AIDS and other inflammatory diseases (J. R. Burke, Curr. Opin. Drug Discov. Devel., 2003, 6: 720-728; Y. Yamamoto and R. B. Gaynor, Curr. Mol. Med., 2001, 1: 287-296; Y. Yamamoto and R. B. Gaynor, J. Clin. Invest., 2001, 107: 135-142).

Interestingly, a synthetic derivative of the natural product rocaglaol was recently found to exhibit neuroprotective activity in vitro and in animal models of Parkinson's disease and traumatic brain injury (T. Fahrig et al., Mol. Pharmacol., 2005 67: 1544-1555). Experimental data suggest that by inhibiting NF-κB and AP-1 (activator protein-1) signaling, this rocaglaol derivative is able to reduce tissue inflammation and neuronal cell death resulting in significant neuroprotection in animal models of acute and chronic neurodegeneration.

Accordingly, another aspect of the present invention relates to the use of derivatives of rocaglamide/aglain/forbaglin family for the manufacture of medicaments for use in the treatment of various diseases, including cancer and cancerous conditions, conditions associated with cellular hyperproliferation, and NF-κB-associated conditions. Preferably, the rocaglamide derivatives used in the manufacture of the these medicaments are prepared by the inventive methods disclosed herein.

Cancer and cancerous conditions that can be treated using such medicaments may be leukemia, sarcoma, breast, colon, bladder, pancreatic, endometrial, head and neck, mesothelioma, myeloma, oesophagal/oral, testicular, thyroid, cervical, bone, renal, uterine, prostate, brain, lung, ovarian, skin, liver and bowel and stomach cancers, tumors and melanomas. Conditions associated with cellular hyperproliferation that can be treated using inventive medicaments may be selected from the group consisting of atherosclerosis, restenosis, rheumatoid arthritis, osteoarthritis, inflammatory arthritis, psoriasis, periodontal disease and virally induced cellular hyperproliferation. NF-κB associated conditions that can be treated using medicaments disclosed herein may be selected from the group consisting of immunological disorders, septic shock, transplant rejection, radiation damage, reperfusion injuries after ischemia, arteriosclerosis and neurodegenerative diseases.

Medicaments according to the present invention may be in liquid, aerosol, semi-solid or solid dosage form, and may be manufactured into any suitable formulation including, but not limited to, solutions, suspensions, micelles, emulsions, microemulsions, syrups, elixirs, aerosols, ointments, gels, suppositories, capsules, tablets, pills, dragees, and the like, as will be required for the appropriate route of administration.

Medicaments of the present invention may be administered by any suitable administration route including, but not limited to, oral, intravenous, intraperitoneal, intramuscular, subcutaneous, inhalation, intranasal, topical, rectal or other administration route known in the art. The route of administration, formulations and dosage of the medicament will be dependent upon a variety of factors including the pathological condition to be treated and the severity and/or extent of the disorder, the age, sex, weight and general health of the particular patient, the potency, bioavailability, in vivo half-life and severity of the side effects of the specific rocaglamide derivative(s) employed in the manufacture of the medicament, the time of administration, the duration of the treatment, drugs used in combination or coincidental with the specific rocaglamide derivative(s) employed, and similar factors well known in the art. These factors are readily determined in the course of therapy. Alternatively of additionally, the dosage to be administered can be determined from studies using animal models for the particular condition to be treated, and/or from animal or human data obtained for compounds which are known to exhibit similar pharmacological activities. A medicament may be formulated in such a way that the total dose required for each treatment is administered by multiple dose or in a single dose. In certain embodiments, the medicament is manufactured or formulated in dosage unit form. The expression "dosage unit form", as used herein, refers to a physically discrete unit of medicament appropriate for the condition/patient to be treated.

In certain embodiments, a medicament according to the present invention comprises one or more rocaglamide derivatives as active ingredients. In other embodiments, the medicament further comprises one or more other therapeutic agents. In certain embodiments, the nature of such additional therapeutic agent(s) will depend on the condition to be treated by administration of the medicament. The ability to determine combinations of compounds suitable to treat particular disorders is well within the capabilities of trained scientists or physicians. For example, a medicament according to the present invention for use in the treatment of cancer may further comprise approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, http://www.nci.nih.gov/, a list of the FDA approved oncology drugs at http://www.fda.gov/cder/cancer/druglistframe.htm, and The Merck Manual, 7th Ed. 1999, the entire contents of which are hereby incorporated by reference.

In addition to the active ingredient(s), a medicament of the present invention may further comprise one or more pharmaceutically acceptable carriers including, but not limited to, inert diluents, dispersion media, solvents, solubilizing agents, suspending agents, emulsifying agents, wetting agents, coatings, isotonic agents, sweetening, flavoring and perfuming agents, antibacterial and antifungal agents, absorptions delaying agents, and the like. The use of such media and agents for the manufacture of medicaments is well known in the art (see, for example, Remington's Pharmaceutical Sciences, E. W. Martin, $18^{th}$ Ed., 1990, Mack Publishing Co., Easton, Pa.).

EXAMPLES

The following examples describe some of the preferred modes of making and practicing the present invention. However, it should be understood that these examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Some of the results presented in the following Examples have been reported in B. Gerard et al., J. Am. Chem. Soc., Jun. 21, 2006, 128: 7754-7755, which is incorporated herein by reference in its entirety.

General Information

Nuclear Magnetic Resonance. $^1$H-NMR spectra were recorded at 400 MHz at ambient temperature with $CDCl_3$ as solvent unless otherwise stated. $^{13}$C-NMR spectra were recorded at 75 or 100 MHz at ambient temperature with $CDCl_3$ as solvent unless otherwise stated. $^1$H-NMR and $^{13}$C-NMR spectra of TADDOL derivatives were recorded on a 400 MHz Bruker DPX Spectrometer. The $^{13}$C resonance frequency is 100 MHz. Chemical shifts are reported in parts per million relative to $CDCl_3$ ($^1$H δ 7.24; $^{13}$C δ 77.0), DMSO-$d_6$ (1H, δ 2.49; 13C, δ 39.7) or $CD_3OD$ ($^1$H, δ 3.35, 4.78; $^{13}$C, δ 49.3). Data for $^1$H-NMR are reported as follows: chemical shift, integration, multiplicity (app=apparent, par obsc=partially obscure, ovrlp=overlapping, s=singlet, d=doublet, t=triplet, q=quartet, m=multiplet) and coupling constants. All $^{13}$C-NMR spectra were recorded with complete proton decoupling.

Infrared Spectroscopy. Infrared spectra were recorded on a Nicolet Nexus 670 FT-IR spectrophotometer. Hydroxyl (OH) stretching frequencies were recorded with a Thermo/Nicolet Nexus 470 FT-IR. The sample cell was a Crystal Labs model SL-3 FTIR NaCl 0.1 mm pathlength cell.

Mass Spectrometry. Low- and high-resolution mass spectra were obtained at the Boston University Mass Spectrometry Laboratory using a Waters Q-TOF API US instrument.

Chromatography. HPLC analyses were performed using an Agilent 1100 series HPLC (Chiracel OD, Column No. OD00CE-AI015 and Regis, Pirkle Covalent (R,R) Whelk-01 column). Analytical thin layer chromatography was performed using 0.25 mm silica gel 60-F plates. Flash chromatography was performed using 200-400 mesh silica gel (Scientific Absorbents, Inc.).

Melting Temperatures. Melting points were recorded on a Mel-Temp apparatus (Laboratory Devices).

Photochemical Irradiation. Photochemistry experiments were performed using a Hanovia 450 W medium pressure mercury lamp housed in quartz immersion coded with a Thermo Neslab-ULT 80 system circulator. Pyrex test tubes (16×100 mm) were mounted on a support approximately 0.5 cm from the immersion well lamp. An uranium filter (>350 nm) was obtained from James Glass (Hanover, Mass.).

All other reactions were carried out in oven-dried glassware under an argon atmosphere unless otherwise noted. Methylene chloride, acetonitrile, methanol, and benzene were purified by passing through two packed columns of neutral alumina (Innovative Technology, Inc., Newburyport, Mass.). Yields refer to chromatographically and spectroscopically pure materials, unless otherwise stated.

Example 1

Preparation of TADDOL Derivatives

A. Preparation of (S,S)-methylene-α-α-α'-α'-tetraphenanthren-9-yl-1,3-dioxo-lane-4,5-dimethanol 7d from (S,S)-dimethyl tartrate Compounds 7a and 7b were purchased from Strem and used without purification. Compound 7c was prepared according to a known procedure (A. Cuenca et al., Helv. Chim. Acta, 2000, 83: 3153-3162).

To a solution of L-dimethyltartrate (1 g, 5.6 mmol, 1 equiv) in EtOAc (10 mL) was added dimethoxymethane (600 μL, 6.7 mmol, 1.2 equiv) and BF$_3$.Et$_2$O (1.78 mL, 13 mmol, 2.5 equiv). The resulting mixture was then refluxed for 7 hours. The reaction was then cooled to room temperature and carefully quenched with saturated NaHCO$_3$. The organic layer was then washed with water (2×100 mL) and brine (1×10 mM). After drying over MgSO$_4$, filtration, and concentration in vacuo, the resulting yellow oil was purified on silica gel (90:10, hexane:EtOAc) to afford 0.94 g (5 mmol, 86%) of dimethyl 2,3-O-methylene-L-tartrate as a colorless oil which was spectroscopically identical to a previously reported compound (A. K. Beck et al., Chimica, 1991, 45: 238-241). A solution containing 0.8 g of 2,3-O-methylene-L-tartrate (4.2 mmol) in THF (5 mL) was added dropwise to a solution of (phenanthren-9-yl)magnesium bromide (21 mmol, prepared from 5.41 g of 9-bromophenanthrene and 0.50 g of Mg powder and a catalytic amount of iodine) in THF (80 mL) at room temperature. The reaction mixture was then stirred at room temperature for 12 hours. The reaction was quenched by careful addition of saturated NH$_4$Cl. The organic layer was separated and the aqueous layer extracted twice with ether (2×50 mL). After the combined organic layers were dried using MgSO$_4$, the solvent was removed in vacuo to afford a yellow oil. Purification via flash chromatography (80:20, hexanes:EtOAc) led to a white solid which was then submitted to precipitation using benzene/hexane (1/1, ca, 60 mL), and dried under high vacuum for 5 hours. 2.54 g (3 mmol, 72%) of 7d was isolated as a white solid.

Compound 7d. White solid, mp 237-239° C.; $[\alpha]_D^{22}$=+343° (c=1.04, CHCl$_3$); IR $\nu_{max}$ (film): 3550, 3060, 2888, 1496, 1448, 1056, 988 cm$^{-1}$; $^1$H NMR (400 MHz, DMSO-d$_6$, 421 K): δ 8.80-8.10 (8H, m), 7.90 (1H, s), 7.70-6.70 (9H, m), 6.20 (1H, s), 4.70 (1H, s) ppm; $^{13}$C NMR (100 MHz, DMSO-d$_6$, 421 K) δ 139.3, 131.9, 131.6, 131.5, 131.0, 130.8, 130.7, 129.8, 129.6, 129.2, 128.6, 127.8, 127.5, 127.4, 127.2, 126.2, 126.1, 125.8, 125.7, 123.9, 123.5, 123.2, 123.1, 98.6, 83.3 ppm; LRMS (APPI+) m/z calculated for C$_{61}$H$_{42}$O$_4$ 838.98 found 821.30 (M−18).

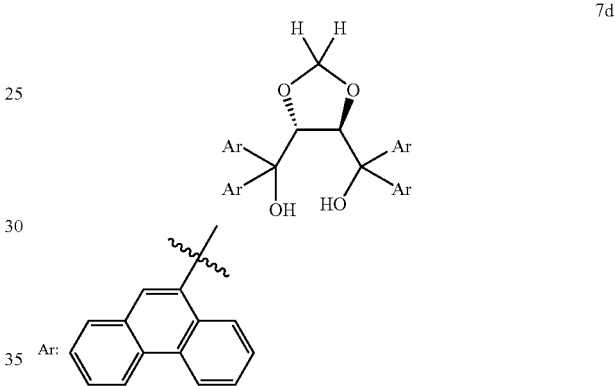

B. (S,S)-diphenyl-α-α-α'-α'-tetraphenanthren-9-yl-1,3-dioxolane-4,5-dimethanol

To a 50 mL round-bottomed flask equipped with a distillation apparatus was added L-dimethyl tartrate (0.5 g, 2.8 mmol, 1 equiv), dimethoxydiphenylmethane (0.66 g, 3.1 mmol, 1.1 equiv) and a catalytic amount of p-TsOH following by 15 mL of anhydrous benzene. The resulting mixture was refluxed until the azeotrope benzene-water was removed (~80° C.). After cooling the mixture to room temperature, the solution was diluted in EtOAc and the organic layer was washed with a saturated NaHCO$_3$ solution (1×15 mL), water (1×15 mL), and brine (1×15 mL). The organic layer was dried over MgSO$_4$, filtered, and evaporated in vacuo to afford a brown oil. The resulting oil is then purified via flash chromatography (90:10, hexane:EtOAc) to afford diphenyl acetal tartrate (0.578 g, 1.60 mmol, 60%) as a white solid which was spectroscopically identical to a previously reported compound (B. Altava et al., Tetrahedron: Asymmetry, 2000, 11: 4885-4893: J. Irrure et al., Tetrahedron: Asymmetry, 1992, 3: 1591-1596). A solution 0.72 g of 2,2-diphenyl-[1,3]dioxolane-4,5-dicarboxylic acid dimethyl ester (2.0 mmol, 1 equiv) in THF (10 mL) was added dropwise to solution of (phenanthren-9-yl)magnesium bromide (10 mmol, 5 equiv) prepared from 2.7 g of 9-bromophenanthrene and 0.25 g of Mg powder and catalytic amount of iodine) in THF (40 mL) at room temperature. The reaction mixture was then stirred at room temperature for 12 hours. The reaction was quenched by careful addition of a saturated solution of NH$_4$Cl. The organic layer was separated and the aqueous layer extracted twice with ether (2×50 mL). After the combined organic layers were dried using MgSO$_4$, the solvent was removed in vacuo to afford a yellow oil. Purification via flash chromatography (80:20 hexanes/EtOAc) afforded a white solid which was then submitted to recrystallization using benzene/hexanes (1/1 ca, 40 mL). After drying under high vacuum for 5 hours, 1.48 g (1.5 mmol, 75%) of 7e was isolated as a white solid.

Compound 7e. White solid: mp 314-317° C.; [α]$_D^{22}$=+519° (c=1.3, CHCl$_3$); IR $\nu_{max}$ (film): 3548, 3060, 1497, 1450, 1223, 1103, 896 cm$^{-1}$; $^1$H NMR (400 MHz, DMSO-d$_6$, 421 K) δ 8.70-8.20 (6H, m), 7.80 (1H, s), 7.70-7.50 (6H, m), 7.30-7.10 (4H, m), 7.0-6.70 (6H, m) ppm; $^{13}$C (100 MHz, DMSO-d$_6$, 421 K) δ 143.9, 139.8, 138.2, 131.9, 131.8, 131.7, 131.6, 131.3, 131.0, 130.9, 129.8, 129.6, 129.4, 129.0, 128.9, 128.3, 128, 127.9, 127.8, 127.5, 127.3, 126.4, 126.1, 126.0, 125.9, 125.6, 125.5, 123.6, 123.4, 123.3, 123.1, 111.3, 84.9, 81.8 ppm; HRMS (APPI+) m/z calculated for C$_{73}$H$_{50}$O$_4$ 991.1757 found 1013.3808 (M+Na).

by careful addition of a saturated NH$_4$Cl solution. The organic layer was separated and the aqueous layer was extracted twice with ether (2×50 mL). After the combined organic layers were dried using MgSO$_4$, the solvent was removed in vacuo to afford a yellow oil. Purification via flash chromatography (80:20 hexanes/EtOAc) afforded a white solid which was then precipitated using methanol/CH$_2$Cl$_2$ (1/1, ca, 40 mL). After drying under high vacuum for 5 h, 1.61 g (1.77 mmol, 46%) of 7f was isolated as a white solid.

Compound 7f. White solid: mp 275-277° C.; [α]$_D^{22}$=+79° (c=2.0, CHCl$_3$); IR $\nu_{max}$ (film): 3566, 3369, 3061, 2934, 2856, 1443, 1218, 1111, 1051, 896 cm$^{-1}$; $^1$H NMR (400 MHz, DMSO-d$_6$, 406 K) δ 8.8 8.7 (12H, m), 8.33-8.27 (4H, m), 8.08 (2H, m), 7.95 (2H, m), 7.60 (10H, m), 7.3 (4H, m), 7.06 (1H, m), 6.78 (1H, m), 5.05 (2H, s), 0.95 (4H, m), 0.55 (2H, m), 0.23 (2H, m) ppm; $^{13}$C NMR (100 MHz, DMSO-d$_6$, 406 K) δ 141.3, 138.8, 132.6, 131.9, 131.8, 131.5, 131.0, 129.8, 129.7, 129.5, 128.3, 128.0, 127.8, 127.7, 127.4, 126.6, 126.4, 126.3, 126.1, 125.6, 123.7, 123.4, 123.3, 111.2, 82.4, 81.1, 49.5, 36.8, 25.0, 24.2 ppm; HRMS (APPI+) m/z calculated for C$_{66}$H$_{50}$O$_4$ 907.1008 found 929.3607 (M+Na).

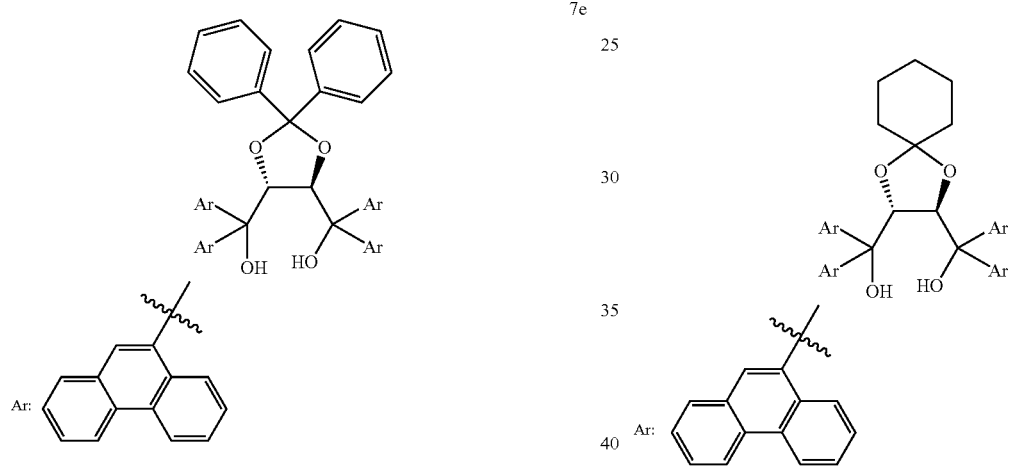

C. Preparation of (S,S)-cyclohexyl-α-α-α'-α'-tetraphenanthren-9-yl-1,3-dioxolane-4,5-dimethanol 7f from (S,S)-dimethyl tartrate To a solution of L-dimethyltartrate (2 g, 11.2 mmol, 1 equiv) in EtOAc (10 mL) was added cyclohexanone (1.39 mL, 13.5 mmol, 1.2 equiv) and BF$_3$.Et$_2$O (3.54 mL, 28 mmol, 2.5 equiv). The resulting mixture was then refluxed for 7 hours. The reaction was then cooled to room temperature and carefully quenched with a solution of a saturated aqueous NaHCO$_3$. The organic layer was then washed with water (2×10 mL) and brine (1×10 mL). After drying over MgSO$_4$, filtration, and concentration in vacuo, the resulting yellow oil was purified on silica gel (90:10, hexane:EtOAc) to afford 2.17 g (8 mmol, 75%) of dimethyl 2,3-O-cyclohexene-L-tartrate as a colorless oil which was spectroscopically identical to previously reported compound (A. K. Beck et al., Chimica, 1991, 45: 238-241). A solution containing 1.00 g of dimethyl 2,3-O-cyclohexene-L-tartrate (3.87 mmol, 1 equiv) in THF (10 mL) was added dropwise to solution of (phenanthren-9-yl)magnesium bromide (19.4 mmol, 5 equiv; prepared from 4.98 g of 9-bromophenanthrene and 0.46 g of Mg powder and catalytic amount of iodine in 70 mL of THF at room temperature). The reaction mixture was then stirred at room temperature for 12 hours. The reaction was quenched D. Preparation of Dimethyl 2,3-O-cyclooctyl-L-tartrate 14

To a solution of L-dimethyltartrate (1.5 g, 8.43 mmol, 1 equiv) in EtOAc (10 mL) was added cyclooctanone (1.22 mL, 9.27 mmol, 1.1 equiv) and BF$_3$.Et$_2$O (2.67 mL, 21.08 mmol, 2.5 equiv). The resulting mixture was then refluxed for 7 hours. The reaction was then cooled at room temperature and carefully quenched with a solution of a saturated NaHCO$_3$. The organic layer was then washed with water (2×10 mL) and brine (1×10 mL). After drying over MgSO$_4$, filtration, concentration in vacuo, the resulting yellow oil was purified on silica gel (90:10, hexane:EtOAc) to afford 2.10 g (7.3 mmol, 87%) of dimethyl 2,3-O-cyclooctene-L-tartrate 14 as a colorless oil.

Compound 14. Colorless oil; [α]$_D^{22}$=−23° (c=1.4, CHCl$_3$); IR $\nu_{max}$ (film): 2924, 2849, 1755, 1440, 1271, 1108, 966 cm$^{-1}$; $^1$H NMR (400 MHz, CDCl$_3$) δ 4.63 (2H, s), 3.68 (6H, s), 1.77 (3H, m), 1.50-1.42 (11H, m) ppm; $^{13}$C NMR (100 MHz, CDCl$_3$) δ 170.3, 118.2, 76.9, 52.8, 34.7, 27.9, 24.5, 22.1 ppm; HRMS (EI) m/z calculated for C$_{14}$H$_{22}$O$_6$ 286.1416 found 309.1427 (M+Na).

14

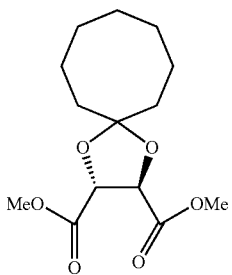

E. Preparation of (S,S)-cyclooctyl-α-α-α'-α'-tetraphenanthren-9-yl-1,3-dioxolane-4,5-dimethanol 7g A solution 0.33 g of dimethyl 2,3-Ocyclooctene-L-tartrate 13 (1.15 mmol) in THF (5 mL) was added dropwise to solution of (pyren-1-yl)magnesium bromide (5.77 mmol, prepared from 1.62 g of 1-bromopyrene and 0.14 g of Mg powder and catalytic amount of iodine in THF (15 mL) at room temperature. The reaction mixture was then stirred at room temperature for 24 hours. The reaction was quenched by careful addition of saturated aqueous NH$_4$Cl. The organic layer was separated and the aqueous layer was extracted twice with ether (2×50 mL). After the combined organic layers were dried using MgSO$_4$, the solvent was removed in vacuo to afford a yellow oil. Purification via flash chromatography (80:20 hexanes/EtOAc) afforded a white solid which was then precipitated using toluene/hexane (1/1, ca, 30 mL). After drying under high vacuum for 5 hours, 0.30 g (0.29 mmol, 25%) of 7g was isolated as a yellow white powder.

Compound 7g. Yellow white powder: mp 286° C.; [α]$_D^{22}$=−89° (c=1.2, CHCl$_3$); IR ν$_{max}$ (film): 3560, 3352, 3041, 2923, 1456, 1213, 1112, 1050, 976 cm$^{-1}$; $^1$H NMR (400 MHz, DMSO-d$_6$, 406 K) δ 9.10 (1H, m), 8.60 (1H, m), 8.40-7.80 (14H, m), 7.50 (1H, m), 7.30 (1H, m), 5.80 (1H, s), 1.20-0.5 (8H, m) ppm; $^{13}$C NMR (100 MHz, DMSO-d$_6$, 406 K) δ 142.1, 139.9, 131.9, 131.7, 131.6, 131.5, 131.0, 130.7, 130.1, 128.5, 128.2, 128.0, 126.8, 126.7, 126.6, 126.3, 126.2, 125.8, 125.6, 125.3, 125.2, 125.0, 124.7, 114.1, 82.6, 81.3, 35.7, 27.8, 24.9, 22.2 ppm; HRMS (APPI+) m/z calculated for C$_{76}$H$_{54}$O$_4$ 1031.2396 found 1053.4226 (M+Na).

7g

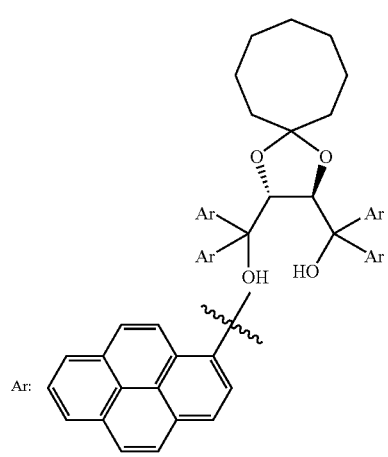

F. Preparation of 1,4,9,12-Tetraoxa-dispiro[4.2.4.2]tetradecane-2,3,10,11-tetra-carboxylic acid tetramethyl ester 15

To a solution of L-dimethyltartrate (6.675 g, 37.50 mmol, 2.1 equiv) in EtOAc (10 mL) was added cyclohexanedione (2 g, 17.85 mmol, 1.1 equiv) and BF$_3$.Et$_2$O (4.97 mL, 39.27 mmol, 2.2 equiv). The resulting mixture was then refluxed for 7 hours. The reaction was then cooled to room temperature and carefully quenched with a solution of a saturated NaHCO$_3$ solution. The organic layer was then washed with water (2×10 mL) and brine (1×10 mL). After drying over MgSO$_4$, filtration, concentration in vacuo, the resulting yellow oil was purified on silica gel (90:10, hexane:EtOAc) to afford 4.50 g (10.4 mmol, 64%) of 1,4,9,12-Tetraoxadispiro[4.2.4.2]tetradecane-2,3,10,11-tetracarboxylic acid tetramethyl ester 15 as a white solid Compound 15. White solid: mp 75-77° C.; [α]$_D^{22}$=−20° (c=1.2, CHCl$_3$); IR ν$_{max}$ (film): 2954, 1758, 1440, 1379, 1223, 1122, 969 cm$^{-1}$; $^1$H NMR (400 MHz, CDCl$_3$) δ 4.78 (1H, s), 3.78 (3H, s), 1.90 (2H, s) ppm; $^{13}$C NMR (100 MHz, CDCl$_3$) δ 170.1, 113.4, 76.9, 52.8, 32.7 ppm; HRMS (APPI+) m/z calculated for C$_{18}$H$_{24}$O$_{12}$ 432.1268 found 455.0861 (M+Na).

15

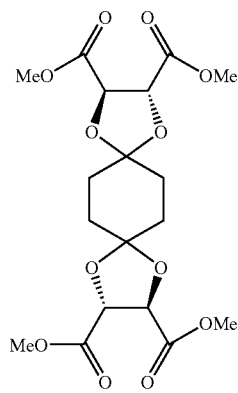

G. Preparation of (S,S,S,S)-(2)-trans,trans-2,3,10-11-tetrakis-(hydroxydipyren-1-yl-methyl)-1,4,9,12-tetraoxadispiro[4.2.4.2]tetradecane 8a A solution 0.46 g of 1,4,9,12-Tetraoxa-dispiro[4.2.4.2]tetradecane-2,3,10,11-tetracarboxylic acid tetramethyl ester (1.07 mmol, 1 equiv) in THF (5 mL) was added dropwise to solution of (pyren-1-yl)magnesium bromide (10.68 mmol) (prepared from 3 g of 1-bromopyrene and 0.256 g of Mg powder and a catalytic amount of iodine in 35 mL of THF at room temperature). The reaction mixture was then stirred at room temperature for 24 hours. The reaction was quenched by careful addition of a saturated aqueous solution of NH$_4$Cl. The organic layer was separated and the aqueous layer was extracted twice with ether (2×50 mL). After the combined organic layers were dried using MgSO$_4$, the solvent was removed in vacuo to afford a yellow oil. Purification via flash chromatography (80:20 hexanes/EtOAc) afforded a white solid which was then submitted twice to precipitation using toluene/hexane (1/1, ca, 30 mL). After drying under high vacuum for 5 hours, 0.60 g (0.35 mmol, 21%) of 8a was isolated as a yellow-white solid.

Compound 8a. Yellow white solid: mp 322° C.; $[\alpha]_D^{22}$=+86° (c=1.2, CHCl$_3$); IR $\nu_{max}$ (film): 3564, 3354, 3041, 2954, 1378, 1131, 1052, 844 cm$^{-1}$; $^1$H NMR (400 MHz, DMSO-d$_6$, 421 K) δ 9-7 (72H, m), 5.80 (4H, m), 1.48-0.33 (8H, m) ppm; $^{13}$C NMR (100 MHz, DMSO-d$_6$, 421 K) δ 141.6, 139.8, 131.4, 130.8, 130.6, 129.8, 128.2, 128.0, 127.8, 127.7, 126.5, 126.2, 125.6, 125.4, 125.3, 125.2, 124.9, 124.3, 110.6, 82.9, 81.6, 33.7 ppm; HRMS (APPI+) m/z calculated for C$_{142}$H$_{88}$O$_8$ 1920.6479 found 1884.60 (M−2×H$_2$O).

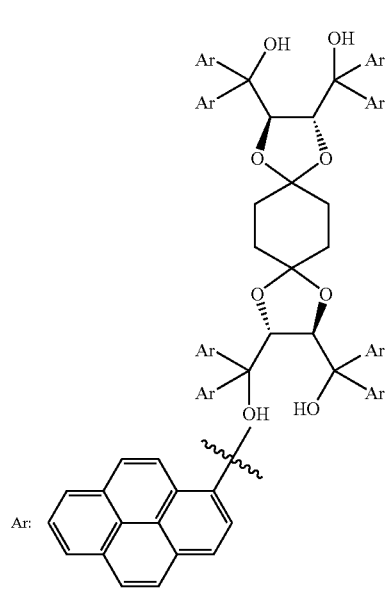

Example 2

Enantioselective Photocycloaddition Reaction and Preparation of Methyl Rocaglate A. Preparation of Trimethoxy cyclopenta[bc]benzopyran 5 by irradiation of 3-Hydroxyflavone 3 and methyl cinnamate 4 in the presence of TADDOL 7g To a 16×150 mm test tube was added 3-hydroxyflavone 3 (100 mg, 0.30 mmol) and methyl cinnamate 4 (250 mg, 1.54 mmol) and TADDOL derivative 7g (315 mg, 0.31 mmol) in 3 ml of anhydrous CH$_2$Cl$_2$ and 7 ml of anhydrous toluene. After degassing with argon for 5 minutes, the mixture was irradiated for 10 hours at −70° C. using a Hanovia UV lamp uranium filter. The solution was concentrated in vacuo to afford a yellow oil. The resulting residue was then triturated with 10 mL of MeOH to precipitate of a yellow-white solid corresponding to the TADDOL derivative 7g. After filtration, the filtrate was dried under vacuum to afford a yellow oil and near quantitative recovery of the TADDOL 7g (92%). Purification via flash chromatography (60:40 hexanes/EtOAc) afforded 87 mg (0.26 mmol, 58%) of trimethoxy cyclopenta[bc]benzopyran 5 (as a diastereomeric mixture of endo/exo cyclopenta[bc]benzopyrans) as a white solid.

Compound 5. White solid: mp 83-85° C.; IR $\nu_{max}$ (film): 3475, 3013, 2943, 2832, 1786, 1737, 1611, 1590, 1510, 1450, 1255, 1146, 1094, 828 cm$^{-1}$; $^1$H NMR (400 MHz, CDCl$_3$) δ 7.54-7.52 (2H, d, J=8.8 Hz), 7.25-7.23 (2H, d, J=8.8 Hz), 7.17-7.49 (2H, m), 7.10-7.04 (6H, m), 6.85-6.82 (2H, m), 6.64-6.60 (4H, m), 6.19-6.18 (1H, d, J=2 Hz), 6.18-6.17 (1H, d, J=2 Hz), 6.11-6.10 (1H, d, J=2 Hz), 6.08-6.07 (1H, d, J=2 Hz), 4.49-4.47 (1H, d, J=9.2 Hz), 4.191-4.168 (1H, d, J=9.2 Hz), 3.94 (1H, s), 3.84 (3H, s), 3.83 (3H, s), 3.77 (4H, m), 3.75 (3H, s), 3.71 (3H, s), 3.66 (4H, m), 3.62 (3H, s), 3.55 (3H, s), 3.29 (1H, s) ppm; $^{13}$C NMR (100 MHz, CDCl$_3$) δ 205.5, 170.7, 170.6, 161.9, 161.3, 158.8, 158.6, 158.4, 153.6, 152.8, 139.9, 138.1, 130.1, 129.8, 128.9, 128.7, 128.2, 127.8, 127.9, 127.0, 126.5, 125.6, 113.6, 112.7, 112.6, 107.7, 106.5, 97.9, 95.5, 94.4, 94.3, 93.6, 93.4, 92.7, 88.7, 83.6, 81.04, 80.7, 62.4, 57.6, 56.1, 55.9, 55.4, 55.3, 55.1, 54.5, 53.4, 52.2, 51.8 ppm; HRMS (CI/NH$_3$) m/z calculated for C$_{28}$H$_{26}$O$_8$ 490.1628 found 491.1739 (M+H).

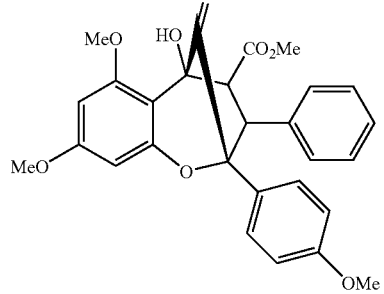

B. Preparation of Keto Rocaglate 11

To a solution of aglain 5 (87 mg, 0.18 mmol, 1 equiv) in MeOH (10 mL) was added a solution of NaOMe (24 mg, 0.44 mmol, 2.5 equiv) in MeOH (2 mL) at room temperature. The resulting solution was stirred for 20 minutes at 60° C. After quenching the reaction with saturated aqueous NH$_4$Cl, 10 mL of EtOAc was then added, and the organic layer was washed with water (2×5 mL) and brine (5 mL). The organic layer was dried over MgSO$_4$, filtered, and concentrated in vacuo to afford 83 mg (0.17 mmol, 95%) of crude ketol shift product 11 (as a diastereomeric mixture of endo/exo keto rocaglates) as yellow oil which was used without further purification.

Compound 11. IR $\nu_{max}$ (film): 501, 3006, 2947, 2926, 2839, 1762, 1734, 1615, 1513, 1450, 1440, 1255, 1213, 1146, 1033, 1076 cm$^{-1}$; $^1$H NMR (400 MHz, CDCl$_3$) δ 7.34-7.32 (2H, d, J=6.8 Hz), 7.20-7.19 (2H, m), 7.09-6.86 (15H, m), 6.65 (2H, d, J=8.8 Hz), 6.51 (2H, d, J=6.8 Hz), 6.33 (1H, d, J=1.6 Hz), 6.17 (1H, d, J=1.6 Hz), 6.13 (1H, d, J=1.6 Hz), 6.12 (1H, d, J=1.6 Hz), 6.05 (1H, d, J=1.6 Hz), 6.00 (1H, d, J=1.6 Hz), 4.46 (1H, s), 4.42 (1H, d, J=14.8 Hz), 4.36 (1H, d, J=14.8 Hz), 4.22 (1H, d, J=13.6 Hz), 4.04 (1H, d, 13.6 Hz), 3.84 (3H, s), 3.08-3.79 (9H, m), 3.77 (9H, m), 3.70 (6H, m), 3.64 (6H, m), 3.57 (3H, s), 3.30 (1H, s), 3.01 (1H, s) ppm; HRMS (EI) m/z calculated for C$_{28}$H$_{26}$O$_8$ 490.1628 found 490.9634 (M+H).

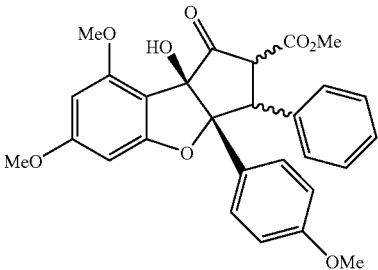

C. Preparation of Endo Methyl Rocaglate 1/Exo Methyl Rocaglate 6

To a solution of 264 mg (1.00 mmol, 6 equiv) of Me$_4$NBH(OAc)$_3$ and 112 µL (0.5 mmol, 10 equiv) of acetic acid in 3 mL of CH$_3$CN was added a solution of 82 mg (0.17 mmol, 1 equiv) of the crude ketol shift 11 product in 1 mL of CH$_3$CN. The resulting green-blue solution was stirred for 3 hours at room temperature before being quenched with 4 mL of saturated aqueous NH$_4$Cl. The solution was then treated with 3 mL of a 3 M aqueous solution of sodium/potassium tartrate and stirred at room temperature for 30 minutes. The aqueous solution was extracted with CH$_2$Cl$_2$ (2×5 mL). The combined organic layers were washed with brine, dried over MgSO$_4$, filtered and concentrated in vacuo. Purification on silica gel (40/60, hexanes/EtOAc) afforded 50 mg (0.10 mmol, 61%) of the corresponding endo methyl rocaglate 1 and 13 mg (0.03 mmol, 16%) of the corresponding exo methyl rocaglate 6.

Recrystallization of 1 (50 mg) from benzene (600 µL)/hexanes (100 µL) afforded 86% (43 mg) recovery of enantiomerically enriched 1 (94% ee) isolated from the mother liquor.

Chiral HPLC analysis of endo methyl rocaglate was performed using Regis, Pirkle Covalent (R, R) Whelk-01 column. Conditions: Gradient, 10 to 60% i-PrOH/hexanes, for 30 min, 0.8 mL/min, 210 nm. t=17.90 min (−)-methyl rocaglate, t 22.26 min (+)-methyl rocaglate, ee=94%

Compound 1. White solid: mp 92-93° C.; [α]$_D^{22}$=−42° (c 098, CHCl$_3$) (94% ee); IR ν$_{max}$ (film): 3013, 2954, 2926, 2853, 1734, 1615, 1517, 1457, 1433, 1262, 1195, 1150, 1031, 832 cm$^{-1}$; $^1$H NMR (400 MHz, CDCl$_3$) δ 7.09 (2H, d, J=9.2 Hz), 7.05-7.03 (3H, m), 6.84 (2H, m), 6.65 (2H, d, J=9.2 Hz), 6.27 (1H, d, J=2 Hz), 6.1 (1H, d, J=2 Hz), 5.01 (1H, dd, J=6.4, 1.2 Hz), 4.28 (1H, d, J=14.4 Hz), 3.80 (1H, dd, J=14.4, 6.4 Hz), 3.86 (3H, s), 3.82 (3H, s), 3.69 (3H, s), 3.63 (3H, s), 3.50 (1H, s), 1.81 (1H, br) ppm; $^{13}$C NMR (100 MHz, CDCl$_3$) δ 170.5, 164.1, 160.9, 158.8, 157.0, 137.0, 129.0, 128.4, 127.8, 127.7, 126.5, 112.7, 107.7, 101.9, 93.7, 92.7, 89.5, 79.6, 60.4, 55.8, 55.1, 55.0, 51.9, 50.6 ppm; HRMS (CI/NH3) m/z calculated for C$_{28}$H$_{28}$O$_8$ 492.1784 found 493.1891 (M+H).

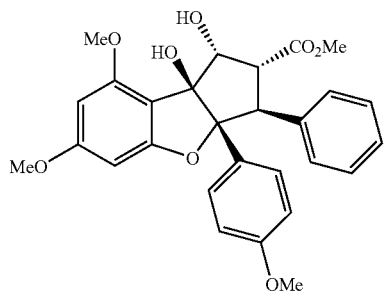

1

Compound 6. Foamy yellow solid: mp 84-85° C.; IR ν$_{max}$ (film): 3031, 3006, 2958, 2936, 2846, 1730, 1636, 1430, 1307, 1258, 1132, 103 cm$^{-1}$ (G. A. Kraus and J. O, Sy, J. Org. Chem., 1989, 54:77-83); $^1$H NMR (400 MHz, CDCl$_3$) δ 7.34 (2H, d, J=8.8 Hz), 7.17-1.15 (3H, m), 6.95-6.94 (2H, m), 6.87 (2H, d, J=8.8 Hz), 6.12 (1H, d, J=1.6 Hz), 6.06 (1H, d, J=1.6 Hz), 4.76 (1H, dd, J=10.2, 1.6 Hz), 4.02 (1H, d, J=12.8 Hz), 3.82 (3H, s), 3.78 (3H, s), 3.77 (3H, s), 3.60 (3H, s), 3.23 (1H, dd, J=12.8, 10.2 Hz), 1.81 (1H, s) ppm; $^{13}$C NMR (100 MHz, CDCl$_3$) δ 173.1, 164.1, 162.0, 159.4, 157.9, 135.0, 129.1, 128.4, 128.0, 127.3, 119.7, 113.6, 105.1, 99.5, 92.6, 91.4, 88.8, 83.9, 55.8, 55.8, 55.4, 54.8, 52.3, 50.9 ppm; HRMS (CI/NH3) m/z calculated for C$_{28}$H$_{28}$O$_8$ 492.1784 found 493.1891 (M+H).

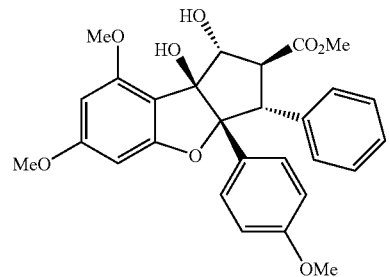

6

Example 3

Preparation of Rocaglaol

A. Preparation of Endo/Exo Cyclopentanone Derivatives 16/17

Keto rocaglate 11 intermediate (30 mg, 0.061 mol, 1 equiv) was dissolved in DMSO (1 mL). 4 mg of lithium chloride was added (0.091 mmol, 1.5 equiv) followed by 5 µL of water (0.182 mmol, 3 equiv). The resulting mixture was heated at 100° C. for 12 hours. After cooling the reaction to room temperature, water (6 mL) was added and the reaction mixture extracted with ethyl acetate (3×5 mL). The combined organic layers were washed once with brine (5 mL), dried over MgSO$_4$, and filtered. The solvent was removed in vacuo and the resulting white solid purified via silica gel (40/60, hexanes/EtOAc) to afford 18 mg (69%, 0.042 mmol) of a 4/1 mixture of endo/exo 16/17 s a white solid. White solid: mp 152° C.; IR ν$_{max}$ (film): 466, 3013, 2940, 2840, 1749, 1609, 1509, 1458, 1345, 1249, 1148, 1036, 998, 812, 756 cm$^{-1}$; HRMS (CI/NH3) m/z calculated for C$_{26}$H$_{24}$O$_6$ 432.1573 found 433.1636 (M+H).

Compound 16: $^1$H NMR (400 MHz, CDCl$_3$) δ 7.09 (3H, m), 6.96 (4H, m), 6.68 (2H, d, J=8.8 Hz), 6.34 (1H, d, J=1.6 Hz), 6.1 (1H, d, J=1.6 Hz), 3.80 (1H, m), 3.84 (3H, s), 3.81 (3H, s), 3.69 (3H, s), 3.00 (2H, m) ppm; $^{13}$C NMR (100 MHz, CDCl$_3$) δ 210.9, 164.9, 161.4, 159.0, 158.7, 137.5, 128.3, 128.2, 128.2, 128.1, 128.0, 127.0, 113.4, 101.5, 98.8, 89.9, 89.0, 55.9, 55.8, 55.7, 48.8, 40.1 ppm.

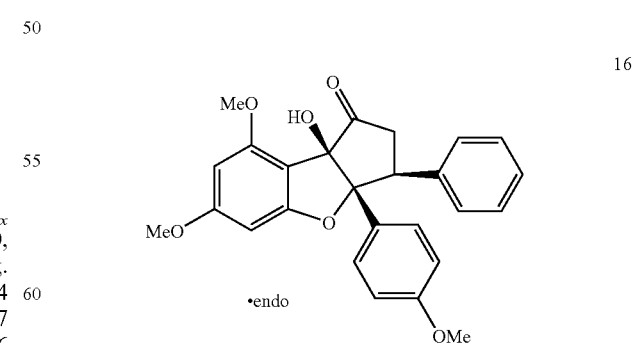

16

Compound 17: $^1$H NMR (400 MHz, CDCl$_3$) δ 7.33 (2H, d, J=8.8 Hz), 7.23 (3H, m), 7.05 (2H, m), 6.88 (2H, d, J=8.8 Hz), 6.14 (1H, d, J=2 Hz), 6.00 (1H, d, J=2 Hz), 4.05 (1H, m), 3.78 (3H, s), 3.77 (3H, s), 3.76 (3H, s), 2.60 (1H, m) ppm; $^{13}$C NMR (100 MHz, CDCl$_3$) δ 209.7, 164.4, 162.5, 159.4, 158.4, 136.0, 129.1, 128.9, 128.3, 128.3, 128.1, 126.1, 113.5, 106.7, 92.6, 88.6, 87.2, 55.8, 55.8, 55.6, 50.9, 39.4 ppm.

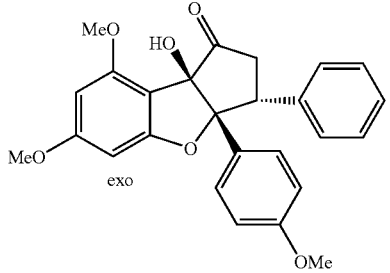

17 exo

B. Preparation of Endo Rocaglaol 9/Exo Rocagloal 12

To a solution of Me$_4$NBH(OAc)$_3$ (66 mg, 0.25 mmol, 6 equiv) and 26 μL (0.4 mmol, 10 equiv) of acetic acid in 3 mL of CH$_3$CN was added a solution of 18 mg (0.04 mmol, 1 equiv) of the crude 16/17 in 1 mL of CH$_3$CN. The resulting green-blue solution was stirred for 3 hours at room temperature before being quenched with 2 mL of saturated aqueous solution of NH$_4$Cl. The solution was then treated with 1 mL of a 3 M aqueous solution of sodium/potassium tartrate and stirred at room temperature for 30 minutes. The aqueous solution was extracted with CH$_2$Cl$_2$ (2×5 mL). The combined organic layers were washed with brine, dried over MgSO$_4$, filtered and concentrated in vacuo. Purification on silica gel (40/60, hexanes/EtOAc) afforded 12 mg (0.027 mmol, 66%) of the corresponding endo rocaglaol 9 as a colorless oil and 3 mg (0.007 mmol, 16%) of the corresponding exo rocaglaol 12 as a colorless oil.

Recrystallization of 9 (50 mg) from CH$_2$Cl$_2$ (500 μL)/isooctane (100 μL) afforded 79% (39 mg) recovery of enantiomerically enriched 9 (96%) isolated from the mother liquor (endo rocaglaol 9 crystallizes as a centrosymmetric racemate).

Chiral HPLC analysis of endo rocaglaol 9 was performed using ChiralCel OD column. Conditions: Gradient, 0 to 18% i-PrOH/hexanes, for 50 min, 0.6 mL/min, 210 nm. t=52.4 min (−)-rocaglaol, t=56.7 min (+)-rocaglaol, ee=96%. [α]$_D^{22}$=−96° (c=0.44, CHCl$_3$)$_{s4}$ (96% ee).

Compound 9: IR ν$_{max}$ (film): 3496, 3008, 2940, 2841, 1607, 1509, 1456, 1337, 1300, 1294, 1204, 1148, 1120, 817 cm$^{-1}$; $^1$H NMR (400 MHz, CDCl$_3$) δ 7.09 (5H, m), 6.97 (2H, d, J=9.2 Hz), 6.6 (2H, d, J=8.8 Hz), 6.27 (1H, d. J=2 Hz), 6.13 (1H, d, J=2 Hz), 4.80 (1H, d, J=6 Hz), 3.9 (1H, dd, J=14.4, 6.8 Hz), 3.88 (3H, s), 3.82 (3H, s), 3. 69 (3H, s), 3.30, (1H, brs), 2.73 (1H, ddd, J=14.4, 13.6, 6.0 Hz), 2.18 (1H, dd, J=13.6, 6.8 Hz) 1.56 (1H, brs); $^{13}$C NMR (100 MHz, CDCl$_3$) δ 163.8, 160.9, 158.5, 156.9, 138.5, 128.8, 127.9, 127.5, 126.6, 126.1, 112.6, 107.6, 103.4, 94.7, 92.3, 89.3, 78.9, 55.6, 55.6, 55.0, 53.1, 36.3 ppm; HRMS (CI/NH3) m/z calculated for C$_{26}$H$_{26}$O$_6$ 434.1729 found 435.1713 (M+H).

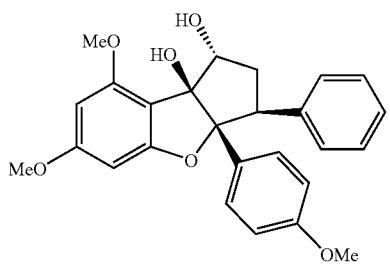

9

Compound 12: IR ν$_{max}$ (film): 3473, 3005, 2928, 2851, 1739, 1606, 1507, 1456, 1248, 1178, 1037, 757 cm$^{-1}$; $^1$H NMR (400 MHz, CDCl$_3$) δ 7.32 (2H, d, J=7.6 Hz), 7.16 (3H, m), 6.98 (2H, m), 6.87 (1H, d. J=7.6 Hz), 6.13 (1H, d, J=2 Hz), 6.06 (1H, d, J=2 Hz), 4.66 (1H, dd, J=11.2, 6 Hz), XX, 3.82 (3H, s), 3.78 (3H, s), 3.76 (3H, s), 2.45, (1H, ddd, J=11.2, 6, 5.2 Hz), 2.09 (1H, ddd, m), 2.77 (1H, dd, J=5.2, 1.2 Hz) ppm; $^{13}$C NMR (100 MHz, CDCl$_3$) δ 164.0, 162.5, 160.2, 159.1, 158.0, 137.8, 129.7, 129.0, 128.4, 127.9, 126.8, 113.6, 106.2, 101.0, 92.6, 92.5, 88.7, 81.4, 55.8, 55.4, 50.8, 34.4 ppm; HRMS (CI/NH3) m/z calculated for C$_{26}$H$_{26}$O$_6$ 434.1729 found 435.1780 (M+H).

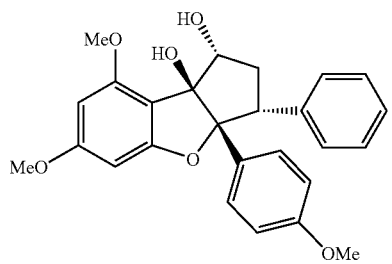

12

Example 4

Preparation of Rocaglamides

A. Preparation of Endo Rocaglic Acid 18/Exo Rocaglic Acid 19

To a solution of 50 mg (0.097 mmol, 1 equiv) of endo methyl rocaglate 1 in MeOH (1.5 mL) was added 22 mg (0.39 mmol, 4 equiv) of potassium hydroxide. The resulting yellow solution was stirred for 12 hours at 44° C. before being quenched with 2 mL of 1N HCl. The aqueous solution was then extracted with EtOAc (2×5 mL). The combined organic layer was dried over MgSO$_4$ and filtered. The solvent was removed in vacuo to afford a crude solid which was recrystallized using CHCl$_3$ to afford 46 mg (96%, 0.09 mmol) of 18 as a white solid.

Compound 18: White solid: mp 110-111° C.; [α]$_D^{22}$=−18° (c=1.16, CHCl$_3$); IR ν$_{max}$ (film): 3489, 3015, 2935, 2843, 1715, 1607, 1508, 1457, 1249, 1215, 1148, 1121, 756 cm$^{-1}$; $^1$H NMR (400 MHz, CDCl$_3$) δ 7.06 (5H, m), 6.86 (2H, m), 6.65 (2H, d, J=8.8 Hz), 6.26 (1H, d, J=2 Hz), 6.09 (1H, d, J=2 Hz), 5.03 (1H, d, J=6.4 Hz), 4.23 (1H, d, J=14 Hz), 3.89 (1H, dd, J=14, 6.8 Hz) 3.83 (3H, s), 3.81 (3H, s), 3.69 (3H, s) ppm; $^{13}$C NMR (100 MHz, CDCl$_3$) δ 175.4, 164.4, 161.0, 158.9, 157.2, 136.9, 129.1, 128.2, 128.1, 128.0, 127.9, 126.8, 126.5, 112.9, 107.7, 102.0, 93.8, 92.9, 89.7, 79.6, 55.9, 55.3, 55.0, 50.5 ppm; HRMS (CI/NH3) m/z calculated for C$_{26}$H$_{26}$O$_6$ 478.1628 found 478.1668.

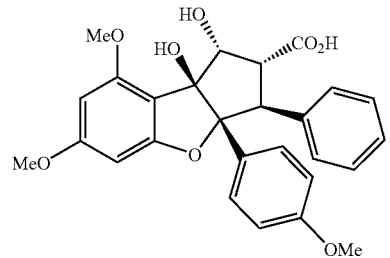

18

B. Preparation of Exo Rocaglic Acid 19

Following the previous procedure using 30 mg (0.06 mmol, 1 equiv) of exo methyl rocaglate 6 in MeOH (1.5 mL)

and 17 mg (0.30 mmol, 5 equiv) of potassium hydroxide, 27 mg (0.056 mmol, 89%) of exo rocaglic acid 19 was isolated as a white solid.

Compound 19: White solid: mp 258-259° C.; IR $v_{max}$ (film): 3446, 2941, 1709, 1603, 1506, 1456, 1250, 1198, 1125, 1006, 907 cm$^{-1}$; $^1$H NMR (400 MHz, CDCl$_3$) δ 7.33 (2H, d, J=8.8 Hz), 7.14 (3H, m), 6.99 (2H, m), 6.15 (2H, s), 4.70 (1H, d, J=10.4 Hz), 3.92 (1H, d, J=12.8 Hz), 3.79 (3H, s), 3.78 (3H, s), 3.78 (3H, s), 3.12 (1H, dd, J=12.8, 10.4 Hz) ppm; $^{13}$C NMR (100 MHz, CDCl$_3$) δ 176.5, 165.2, 163.1, 160.5, 160.2, 136.8, 131.5, 130.4, 129.6, 128.7, 128.0, 113.9, 106.8, 100.6, 93.4, 92.3, 89.1, 85.2, 56.4, 56.1, 55.9, 55.7, 52.3 ppm; HRMS (CI/NH3) m/z calculated for C$_{26}$H$_{26}$O$_6$ 478.1628 found 478.1635.

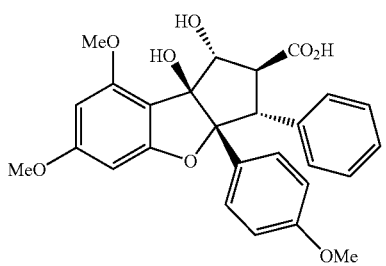

19

C. Preparation of Endo Rocaglamide 10

To a solution of 33 mg (0.069 mmol, 1 equiv) of endo rocaglic acid 18 in DMF (2 mL) was added dimethylamine hydrochloride (7 mg, 0.08 mmol, 1.2 equiv) and DMAP (9.1 mg, 0.08 mmol, 1.2 equiv). After cooling the reaction mixture to 0° C., EDCI (13 mg, 0.08 mmol, 1.2 equiv) was added portionwise over a 5 minute-period. The mixture was stirred at 0° C. for 30 minutes. A solution of triethylamine (11 µL, 0.08 mmol, 1.2 equiv) was then added and the reaction mixture stirred for an additional 1 hour and 12 hours at room temperature before being quenched with 1 mL of 1N HCL solution and diluted with water. The aqueous solution was then extracted twice with CH$_2$Cl$_2$ (2×10 mL). The collected organic layer was washed with brine (1×10 mL). After drying over MgSO$_4$, and filtration, the organic solvent was removed in vacuo to afford a yellow oil which was then purified using silica gel chromatography (95/05, CH$_2$Cl$_2$/MeOH) to afford 22 mg (0.045 mmol, 65%) of rocaglamide 10 as a white solid.

Chiral HPLC analysis of endo rocaglamide 10 was obtained using Chiracel OD column. Conditions: Gradient, 10 to 60% i-PrOH/hexanes, for 40 min, 1 mL/min, 210 nm. t=26.29 min (+)-rocaglamide, t=32.77 min (−)-rocaglamide, ee 94%.

Compound 19: White solid: mp 117-118° C.; [α]$_D^{22}$−99° (c=0.13, CHCl$_3$) (94% ee); IR $v_{max}$ (film): 3475, 2938, 2841, 1718, 1619, 1506, 1457, 1336, 1251, 1199, 1147, 1121, 1036, 997 cm$^{-1}$; $^1$H NMR (400 MHz, CDCl$_3$) δ 7.09 (2H, d, J=8.7 Hz), 7.00 (3H, m), 6.84 (2H, m), 6.65 (2H, d, J=8.7 Hz), 6.25 (1H, d, J=2.1 Hz), 6.08 (1H, d, J=2.1 Hz), 4.92 (1H, d, J=6.6 Hz), 4.53 (1H, d, J=13.5 Hz), 4.04 (1H, dd, J=13.5, 6.6 Hz), 3.83 (3H, s), 3.81 (3H, s), 3.44 (1H, s), 3.29 (3H, s), 2.92 (3H, m), 0.90 (1H, s) ppm; $^{13}$C NMR (100 MHz, CDCl$_3$) δ 169.5, 163.9, 161.1, 158.6, 157.2, 137.6, 128.8, 127.8, 127.7, 127.6, 127.1, 126.3, 112.7, 107.6, 101.7, 94.0, 92.5, 89.3, 78.6, 77.9, 55.9, 55.7, 55.1, 47.7, 37.1, 35.8 ppm; HRMS (CI/NH3) m/z calculated for C$_{29}$H$_{31}$NO$_7$ 505.2101 found 506.1982 (M+H).

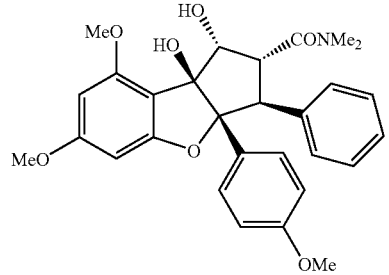

10

C. Preparation of Exo Rocaglamide 12

Following the same experimental procedure for compound 10, to 35 mg (0.07 mmol, 1 equiv) of exo rocaglic acid 18 in DMF (2 mL) was added 14 mg (0.09 mmol, 1.2 equiv) of EDCI, 10 mg (0.09 mmol, 1.2 equiv) of DMAP, 7.1 mg (0.09, 1.2 equiv) of dimethylamine hydrochloride and 13 µL (0.09 mmol, 1.2 equiv) of triethylamine. After purification using silica gel chromatography (95/05, CH$_2$Cl$_2$/MeOH), 27 mg (0.056 mmol, 63%) of the exo rocaglamide 12 was isolated as a white solid.

Compound 12: White solid: mp 181-182° C.; IR $v_{max}$ (film): 3478, 2932, 2846, 1731, 1622, 1506, 1457, 1253, 1204, 1147, 1127, 1036, 912 cm$^{-1}$; $^1$H NMR (400 MHz, CDCl$_3$) δ 7.40 (2H, d, J=8.8 Hz), 7.16 (3H, m), 7.01 (2H, m), 6.88 (2H, d, J=8.8 Hz), 6.20 (1H, d, J=2 Hz), 6.10 (1H, d, J=2 Hz), 4.82 (1H, d, J 10 Hz), 4.24 (1H, d, J=12.4 Hz), 3.83 (3H, s), 3.82 (3H, s), 3.79 (3H, s), 3.56 (1H, dd, J=10, 12.4 Hz), 2.99 (3H, s), 2.87 (3H, s), 2.00 (1H, br s) ppm; $^{13}$C NMR (100 MHz, CDCl$_3$) δ 171.7, 163.9, 162.2, 159.4, 158.1, 135.9, 129.5, 129.3, 128.6, 128.1, 127.3, 113.6, 105.9, 100.2, 92.6, 91.9, 88.8, 84.9, 55.9, 55.8, 55.4, 55.0, 47.5, 37.7, 36.2 ppm; HRMS (CI/NH3) m/z calculated for C$_{29}$H$_{31}$NO$_7$ 505.2101 found 506.2194 (M+H).

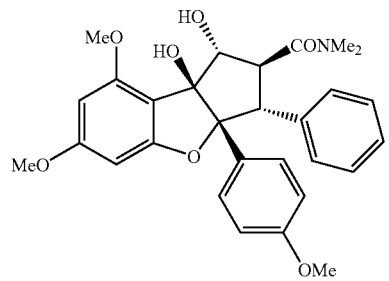

12

Example 5

X-Ray Crystallography Data

Crystals of compound 1 suitable for x-ray analysis were obtained by slow evaporation from benzene/hexanes. Crystallographic data have been deposited with the Cambridge Crystallographic Data Centre (CCDC 604104). Copies of the data can be obtained free of charge on application to the CCDC, 12 Union Road, Cambridge CB21EZ, UK (fax: (+44)-1223-336-033; e-mail: deposit@ccdc.cam.ac.uk.

FIG. 13(A) shows crystal data obtained for compound 1, and FIG. 13(B) shows a unit cell representation for the centrosymmetric racemate 1. FIG. 14 is a table presenting crystal data and structure refinement for compound 1.

Crystals of compound 7d suitable for x-ray analysis were obtained by slow evaporation from $CH_2Cl_2$/isooctane. Crystallographic data have been deposited with the Cambridge Crystallographic Data Centre (CCDC 604103). Copies of the data can be obtained as described above. FIG. 15(A) shows crystal data for compound 7d. FIG. 16 is table summarizing crystal data and structure refinement for compound 7d.

Crystals of compound 7e suitable for x-ray analysis were obtained by slow evaporation from $CH_2Cl_2$/isooctane. Crystallographic data have been deposited with the Cambridge Crystallographic Data Centre (CCDC 604102). Copies of the data can be obtained as described above. FIG. 15(B) shows crystal data for compound 7e. FIG. 17 is table summarizing crystal data and structure refinement for compound 7e.

Other Embodiments

Other embodiments of the invention will be apparent to those skilled in the art from a consideration of the specification or practice of the invention disclosed herein. It is intended that the specification and Examples be considered as exemplary only, with the true scope of the invention being indicated by the following claims.

TABLE 1

| entry | additive | yield of 5, %[b] | yield of 1/6, %[c] | ee of 1/6, %[d] |
|---|---|---|---|---|
| 1 | — | 32 | 45/19 | racemic |
| 2[e] | 7a | 60 | 41/15 | 7/5 |
| 3[e] | 7b | 61 | 49/7 | 25/18 |
| 4 | 7a | 51 | 35/4 | 15/7 |
| 5 | 7b | 92 | 52/9 | 40/36 |
| 6 | 7c | 90 | 71/14 | 60/58 |
| 7 | 7d | 70 | 69/14 | 25/22 |
| 8 | 7e | 54 | 72/22 | racemic |
| 9 | 7f | 79 | 67/19 | 71/51 |
| 10[f] | 7f | 73 | 47/9 | 53/30 |
| 11 | 7g | 58 | 61/16 | 82/68 |
| 12 | 8a | 22 | 52/7 | 89/78 |

Reactions conducted with 1 equiv of 3-HF, 1 equiv of additive, and 5 equiv. of methyl cinnamate in toluene/$CH_2Cl_2$ (2/1) at −70° C. for 12 hours.
[b]Isolated yield.
[c]Isolated yield for the α-ketol rearrangement/reduction sequence.
[d]Determined by chiral HPLC.
[e]Reaction conducted at 0° C. in toluene.
[f]Reaction conducted in the presence of anhydrous $CH_3OH$ (5 equiv).

TABLE 2

| entry | additive | temperature | Solvent | yield of 5, %[b] | yield of 1/6, %[c] | ee of 1/6, %[d] |
|---|---|---|---|---|---|---|
| 1[a] | 7a | 0° C. | Toluene | 60 | 41/15 | 7/5 |
| 2[a] | 7b | 0° C. | Toluene | 61 | 49/7 | 25/18 |
| 3[a] | 7a | −70° C. | Toluene/$CH_2Cl_2$ 2/1 | 51 | 35/4 | 15/7 |
| 4[a] | 7b | −70° C. | Toluene/$CH_2Cl_2$ 2/1 | 92 | 52/9 | 40/36 |

[a]Reactions conducted with 1 equiv of 3-HF, 1 equiv of additive, and 5 equiv. of methyl cinnamate.
[b]Isolated yield.
[c]Isolated yield for the α-ketol rearrangement/reduction sequence.
[d]Determined by chiral HPLC

TABLE 3

| entry | additive | Conditions | Conc. of 3 | Equiv of 4 | yield of 5, %[a] | yield of 1/6, %[b] | ee of 1/6, %[c] |
|---|---|---|---|---|---|---|---|
| 5 | 7c 1 equiv | Toluene/$CH_2Cl_2$ 70° C.; 2/1 | 0.03 M | 5 | 90 | 71/14 | 60/58 |
| 6 | 7c 1 equiv | $CH_2Cl_2$, −70° C. | 0.03 M | 1.5 | 56 | 66/28 | 54/48 |
| 7 | 7c 1 equiv | $CH_2Cl_2$, −70° C. | 0.1 M | 1.5 | 70 | 67/15 | 55/48 |
| 8 | 7c 1 equiv | $CH_2Cl_2$, −70° C. | 0.2 M | 1.5 | 59 | 64/17 | 45/43 |
| 9 | 7f 1 equiv | Toluene/$CH_2Cl_2$ 70° C.; 2/1 | 0.03 M | 5 | 79 | 67/19 | 70/47 |
| 10 | 7f 2 equiv | Toluene/$CH_2Cl_2$ 70° C.; 2/1 | 0.03 M | 5 | 92 | 47/15 | 71/50 |

[a]Isolated yield.
[b]Isolated yield for the α-ketol rearrangement/reduction sequence.
[c]Determined by chiral HPLC

What is claimed is:

1. A method comprising steps of: photochemically generating an oxidopyrylium species from a 3-hydroxychromone derivative; and reacting the oxidopyrylium species with a dipolarophile, wherein the steps of photochemically generating the oxidopyrylium species and of reacting the oxidopyrylium species with a dipolarophile are carried out in the presence of a TADDOL derivative.

2. The method of claim 1, wherein the oxidopyrylium species is photochemically generated via a process comprising an excited state intramolecular proton transfer.

3. The method of claim 2, wherein the step of reacting the oxidopyrylium species and the dipolarophile comprises a cycloaddition leading to the formation of an adduct.

4. The method of claim 3, wherein the cycloaddition comprises a 1,3-dipolar cycloaddition.

5. The method of claim 4, wherein the 1,3-dipolar cycloaddition is enantioselective.

6. The method of claim 2, wherein the oxidopyrylium species is photochemically generated from a 3-hydroxychromone derivative with the following chemical structure:

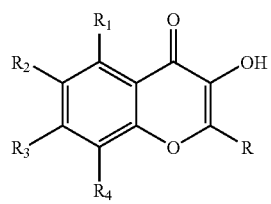

(I)

wherein $R_1$, $R_2$, $R_3$, $R_4$ and R are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —C(=O)$R_x$, —$CO_2(R_x)$, —C(=O)N($R_x$)$_2$, —OC(=O)N($R_x$)$_2$, —OC(=O)$R_x$, —$OCO_2R_x$, —S(O)$R_x$, —S(O)$_2R_x$, —$NR_x$(CO)$R_x$, —N($R_x$)$CO_2R_x$, —N($R_x$)C(=O)N($R_x$)$_2$, —N($R_x$)S(O)$_2R_x$, and —S(O)$_2$N($R_x$)$_2$, wherein each occurrence of $R_x$ is independently selected from the group consisting of hydrogen, aliphatic, alicyclic, heteroaliphatic, heterocyclic, aromatic, heteroaromatic, aryl, and heteroaryl.

7. The method of claim 2, wherein the oxidopyrylium species is photochemically generated from a 3-hydroxyflavone derivative with the following chemical structure:

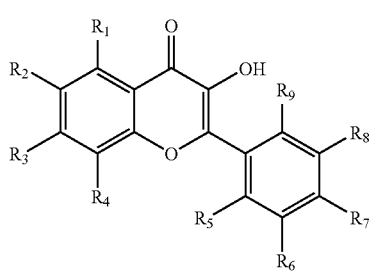

(II)

wherein $R_1$, $R_2$, $R_3$, $R_4$, $R_5$, $R_6$, $R_7$, $R_8$ and $R_9$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —C(=O)$R_x$, —$CO_2(R_x)$, —C(=O)N($R_x$)$_2$, —OC(=O)N($R_x$)$_2$, —OC(=O)$R_x$, —$OCO_2R_x$, —S(O)$R_x$, —S(O)$_2R_x$, —$NR_x$(CO)$R_x$, —N($R_x$)$CO_2R_x$, —N($R_x$)C(=O)N($R_x$)$_2$, —N($R_x$)S(O)$_2R_x$, and —S(O)$_2$N($R_x$)$_2$, wherein each occurrence of $R_x$ is independently selected from the group consisting of hydrogen, aliphatic, alicyclic, heteroaliphatic, heterocyclic, aromatic, heteroaromatic, aryl, and heteroaryl.

8. The method of claim 7, wherein the 3-hydroxyflavone derivative has one of the following chemical structures:

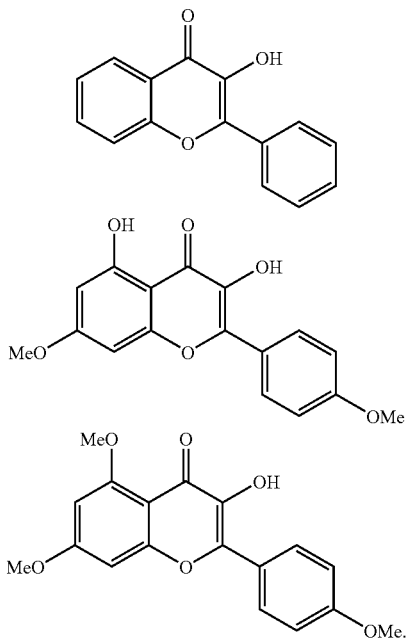

9. The method of claim 2, wherein the dipolarophile is a cinnamate derivative.

10. The method of claim 2, wherein the TADDOL derivative is a L-tartrate derivative.

11. The method of claim 2, wherein the TADDOL derivative has the following structure:

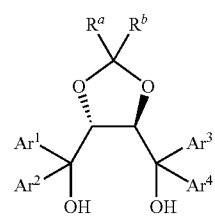

wherein $R^a$ and $R^b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —NO$_2$, —CN, —CF$_3$, —CH$_2$CF$_3$, —CHCl$_2$, —CH$_2$OH, —CH$_2$CH$_2$OH, —CH$_2$SO$_2$CH$_3$, —C(=O)R$_x$, —CO$_2$(R$^x$), —C(=O)N(R$^x$)$_2$, —OC(=O)N(R$^x$)$_2$, —OC(=O)R$^x$, —OCO$_2$R$^x$, —S(O)R$^x$, —S(O)$_2$R$^x$, —NR$^x$(CO)R$^x$, —N(R$^x$)CO$_2$R$^x$, —N(R$^x$)C(=O)N(R$^x$)$_2$, —N(R$^x$)S(O)$_2$R$^x$, and —S(O)$_2$N(R$^x$)$_2$, wherein each occurrence of R$^x$ is independently selected from the group consisting of hydrogen, aliphatic, alicyclic, heteroaliphatic, heterocyclic, aromatic, heteroaromatic, aryl, and heteroaryl; and wherein Ar$^1$, Ar$^2$, Ar$^3$, and Ar$^4$ are be identical or different and selected from the group consisting of substituted or unsubstituted aryloxy, heteroaryloxy, thioaryl, aryl, heteroaryl, arylamino, and amino aryl.

12. The method of claim 2, wherein the TADDOL derivative has the following structure:

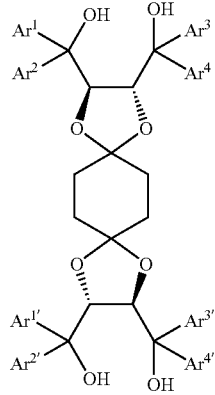

wherein Ar$^1$, Ar$^2$, Ar$^3$, Ar$^4$ Ar$^{1'}$, Ar$^{2'}$, Ar$^{3'}$, and Ar$^{4'}$ are identical or different and selected from the group consisting of substituted or unsubstituted aryloxy, heteroaryloxy, thioaryl, aryl, heteroaryl, arylamino, and amino aryl.

13. The method of claim 2, wherein the steps of photochemically generating the oxidopyrylium species and of reacting the oxidopyrylium species with a dipolarophile are carried out in an aprotic solvent.

14. The method of claim 13, wherein the aprotic solvent is selected from the group consisting of hexane, toluene, pentane, cyclohexane, dioxane, carbon tetrachloride, benzene, carbon disulfide, toluene, diethyl ether, chloroform, ethyl acetate, tetrahydrofuran, methylene chloride, pyridine, dimethylformamide, acetonitrile, dimethylsulfoxide, and combinations thereof.

15. The method of claim 2, wherein the steps of photochemically generating the oxidopyrylium species and of reacting the oxidopyrylium species with a dipolarophile are carried out at a temperature lower than 0° C.

16. The method of claim 15, wherein the temperature lower than 0° C. is comprised in a range selected from the group consisting of between –20° C. and –40° C., between –30° C. and –50° C., between –40° C. and –60° C., between –50° C. and –70° C., between –60° C. and –80° C., and between –70° C. and –90° C.

17. The method of claim 3 further comprising a step of converting the adduct formed.

18. The method of claim 17, wherein the adduct formed comprises an aglain core structure and wherein converting the adduct formed results in formation of a ring system selected from the group consisting of an aglain ring system, a rocaglamide ring system, and a forbaglin ring system.

19. A method for preparing a compound with an aglain core structure, the method comprising steps of:

producing an oxidopyrylium species (I$_T$) by photoinduced excited state intramolecular proton transfer of a 3-hydroxychromone derivative (I); and reacting the oxidopyrylium species with a dipolarophile (IV) to obtain the aglain core-containing compound (V), wherein compounds (I), (I$_T$), (IV) and (V) have the following chemical structures:

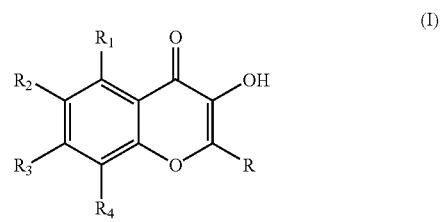

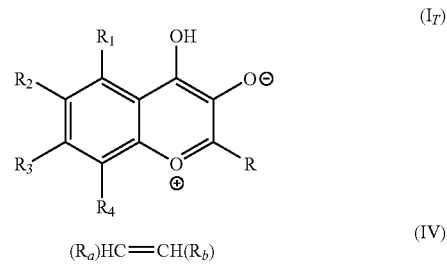

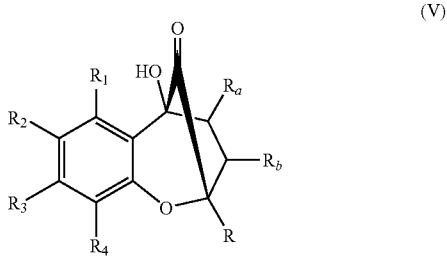

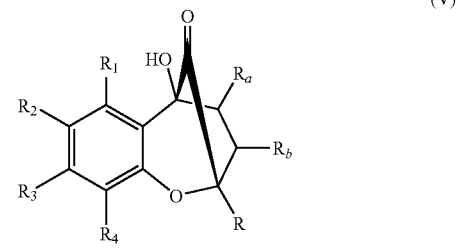

wherein R$_1$, R$_2$, R$_3$, R$_4$, R, R$_a$ and R$_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —NO$_2$, —CN, —CF$_3$, —CH$_2$CF$_3$, —CHCl$_2$, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —OC(=O)N(R$_x$)$_2$, —OC(=O)R$_x$, —OCO$_2$R$_x$, —S(O)R$_x$, —S(O)$_2$R$_x$, —NR$_x$(CO)R$_x$, —N(R$_x$)CO$_2$R$_x$, —N(R$_x$)C(=O)N(R$_x$)$_2$, —N(R$_x$)S(O)$_2$R$_x$, and —S(O)$_2$N(R$_x$)$_2$, wherein each occurrence of R$_x$ is independently selected from the group consisting of hydrogen, aliphatic, alicyclic, heteroaliphatic, heterocyclic, aromatic, heteroaromatic, aryl, and heteroaryl, and wherein the steps of producing the oxidopyrylium species and of reacting the oxidopyrylium species with a dipolarophile are carried out in the presence of a TADDOL derivative.

20. A method for preparing a compound with an aglain core structure, the method comprising steps of:
producing an oxidopyrylium species ($II_T$) by photoinduced excited state intramolecular proton transfer of a 3-hydroxyflavone derivative (II); and
reacting the oxidopyrylium species with a dipolarophile (IV) to obtain the aglain core-containing compound (V'), wherein compounds (II), ($II_T$), (IV) and (V') have the following chemical structures:

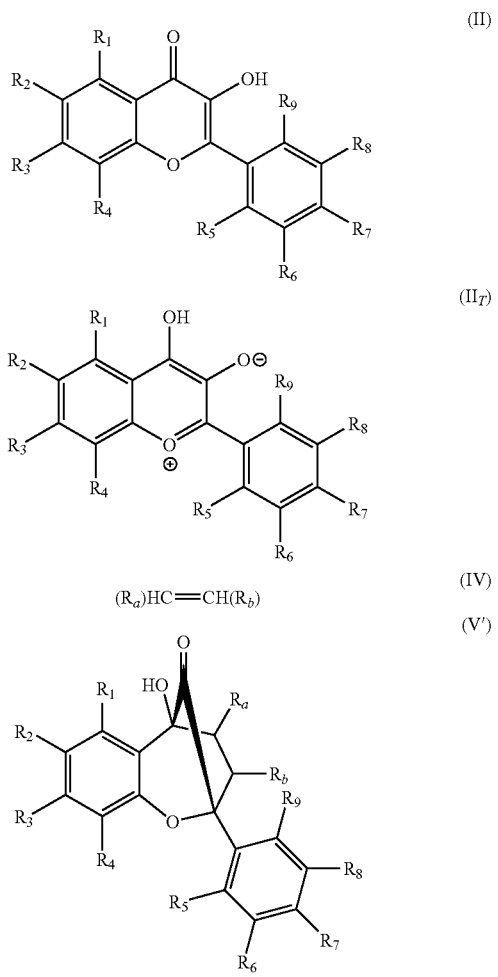

wherein $R_1$, $R_2$, $R_3$, $R_4$, $R_5$, $R_6$, $R_7$, $R_8$, $R_9$, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —C(=O)$R_x$, —$CO_2(R_x)$, —C(=O)N$(R_x)_2$, —OC(=O)N$(R_x)_2$, —OC(=O)$R_x$, —OCO$_2R_x$, —S(O)$R_x$, —S(O)$_2R_x$, —$NR_x$(CO)$R_x$, —N($R_x$)CO$_2R_x$, —N($R_x$)C(=O)N$(R_x)_2$, —N($R_x$)S(O)$_2R_x$, and —S(O)$_2$N$(R_x)_2$,
wherein each occurrence of $R_x$ is independently selected from the group consisting of hydrogen, aliphatic, alicyclic, heteroaliphatic, heterocyclic, aromatic, heteroaromatic, aryl, and heteroaryl, and wherein the steps of producing the oxidopyrylium species and reacting the oxidopyrylium species with a dipolarophile are carried out in the presence of a TADDOL derivative.

21. The method of claim 19 or 20, wherein the step of reacting the oxidopyrylium species with the dipolarophile comprises a 1,3-dipolar cycloaddition.

22. The method of claim 21, wherein the 1,3-dipolar cycloaddition is enantioselective.

23. The method of claim 20, wherein the 3-hydroxyflavone derivative has one of the following chemical structures:

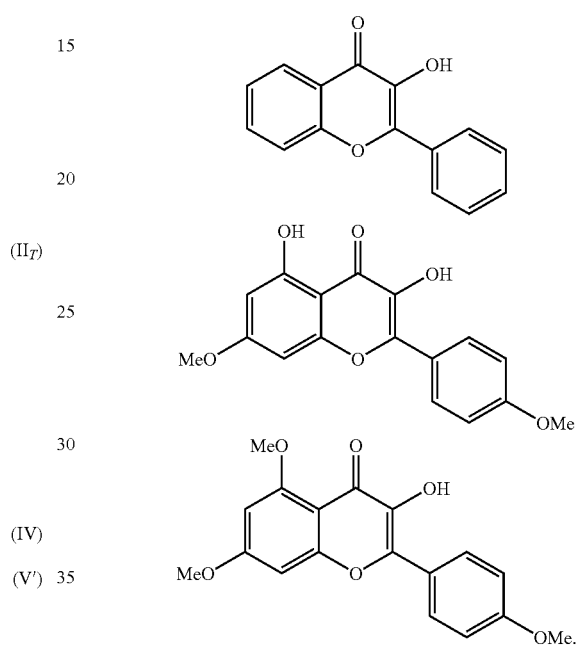

24. The method of claim 19 or 20, wherein the dipolarophile (IV) is a cinnamate derivative with the following chemical structure:

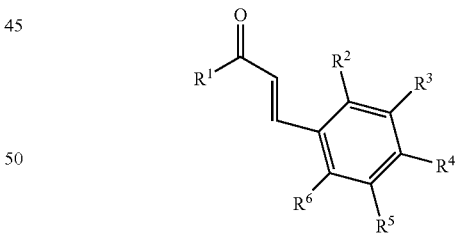

wherein $R^1$ is selected from the group consisting of hydrogen, hydroxy, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, and a protecting group; and
wherein $R^2$, $R^3$, $R^4$, $R^5$, and $R^6$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —CH$_2$CF$_3$, —CHCl$_2$, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —OC(=O)N(R$_x$)$_2$, —OC(=O)R$_x$, —OCO$_2$R$_x$, —S(O)R$_x$, —S(O)$_2$R$_x$, —NR$_x$(CO)R$_x$, —N(R$_x$)CO$_2$R$_x$, —N(R$_x$)C(=O)N(R$_x$)$_2$, —N(R$_x$)S(O)$_2$R$_x$, and —S(O)$_2$N(R$_x$)$_2$, wherein each occurrence of R$_x$ is independently selected from the group consisting of hydrogen, aliphatic, alicyclic, heteroaliphatic, heterocyclic, aromatic, heteroaromatic, aryl, and heteroaryl.

25. The method of claim 19 or 20, wherein the TADDOL derivative is a L-tartrate derivative.

26. The method of claim 19 or 20, wherein the TADDOL derivative has the following structure:

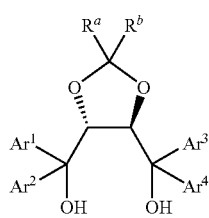

wherein R$^a$ and R$^b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —NO$_2$, —CN, —CF$_3$, —CH$_2$CF$_3$, —CHCl$_2$, —CH$_2$OH, —CH$_2$CH$_2$OH, —CH$_2$SO$_2$CH$_3$, —C(=O)R$^x$, —CO$_2$(R$^x$), —C(=O)N(R$^x$)$_2$, —OC(=O)N(R$^x$)$_2$, —OC(=O)R$^x$, —OCO$_2$R$^x$, S(O)R$^x$, S(O)$_2$R$^x$, —NR$^x$(CO)R$^x$, —N(R$^x$)CO$_2$R$^x$, —N(R$^x$)C(=O)N(R$^x$)$_2$, —N(R$^x$)S(O)$_2$R$^x$, and —S(O)$_2$N(R$^x$)$_2$, wherein each occurrence of R$^x$ is independently selected from the group consisting of hydrogen, aliphatic, alicyclic, heteroaliphatic, heterocyclic, aromatic, heteroaromatic, aryl, and heteroaryl; and wherein Ar$^1$, Ar$^2$, Ar$^3$, and Ar$^4$ are be identical or different and selected from the group consisting of substituted or unsubstituted aryloxy, heteroaryloxy, thioaryl, aryl, heteroaryl, arylamino, and amino aryl.

27. The method of claim 19 or 20, wherein the TADDOL derivative has the following structure:

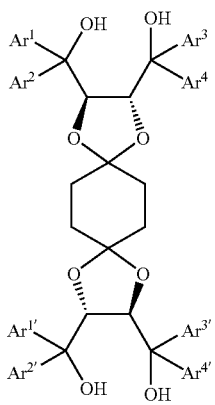

wherein Ar$^1$, Ar$^2$, Ar$^3$, Ar$^4$ Ar$^{1'}$, Ar$^{2'}$, Ar$^{3'}$, and Ar$^{4'}$ are identical or different and selected from the group consisting of substituted or unsubstituted aryloxy, heteroaryloxy, thioaryl, aryl, heteroaryl, arylamino, and amino aryl.

28. The method of claim 19 or 20, wherein the steps of producing the oxidopyrylium species and of reacting the oxidopyrylium species with a dipolarophile are carried out in an aprotic solvent.

29. The method of claim 28, wherein the aprotic solvent is selected from the group consisting of hexane, toluene, pentane, cyclohexane, dioxane, carbon tetrachloride, benzene, carbon disulfide, toluene, diethyl ether, chloroform, ethyl acetate, tetrahydrofuran, methylene chloride, pyridine, dimethylformamide, acetonitrile, dimethylsulfoxide, and combinations thereof.

30. The method of claim 19 or 20, wherein the steps of producing the oxidopyrylium species and of reacting the oxidopyrylium species with a dipolarophile are carried out at a temperature lower than 0° C.

31. The method of claim 30, wherein the temperature lower than 0° C. is comprised in a range selected from the group consisting of between –20° C. and –40° C., between –30° C. and –50° C., between –40° C. and –60° C., between –50° C. and –70° C., between –60° C. and –80° C., and between –70° C. and –90° C.

32. The method of claim 19 further comprising a step of converting the compound with an aglain core structure into a rocaglamide (VII) with the following chemical structure:

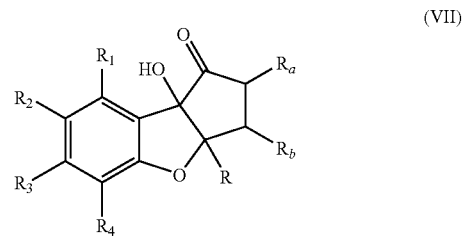

(VII)

wherein R$_1$, R$_2$, R$_3$, R$_4$, R, R$_a$ and R$_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —NO$_2$, —CN, —CF$_3$, —CH$_2$CF$_3$, —CHCl$_2$, —CH$_2$OH, —CH$_2$CH$_2$OH, —CH$_2$SO$_2$CH$_3$, —C(=O)R$_x$, —CO$_2$(R$_x$), —C(=O)N(R$_x$)$_2$, —OC(=O)N(R$_x$)$_2$, —OC(=O)R$_x$, —OCO$_2$R$_x$, —S(O)R$_x$, —S(O)$_2$R$_x$, —NR$_x$(CO)R$_x$, —N(R$_x$)CO$_2$R$_x$, —N(R$_x$)C(=O)N(R$_x$)$_2$, —N(R$_x$)S(O)$_2$R$_x$, and —S(O)$_2$N(R$_x$)$_2$, wherein each occurrence of R$_x$ is independently selected from the group consisting of hydrogen, aliphatic, alicyclic, heteroaliphatic, heterocyclic, aromatic, heteroaromatic, aryl, and heteroaryl.

33. The method of claim 20 further comprising a step of converting the compound with an aglain core structure into a rocaglamide derivative (VII') with the following chemical structure:

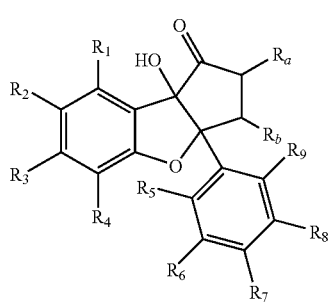

(VII')

wherein $R_1$, $R_2$, $R_3$, $R_4$, $R_5$, $R_6$, $R_7$, $R_8$, $R_9$, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —C(=O)$R_x$, —$CO_2(R_x)$, —C(=O)N$(R_x)_2$, —OC(=O)N$(R_x)_2$, —OC(=O)$R_x$, —$OCO_2R_x$, —S(O)$R_x$, —$S(O)_2R_x$, —$NR_x$(CO)$R_x$, —N$(R_x)CO_2R_x$, —N$(R_x)$C(=O)N$(R_x)_2$, —N$(R_x)S(O)_2R_x$, and —$S(O)_2N(R_x)_2$,
    wherein each occurrence of $R_x$ is independently selected from the group consisting of hydrogen, aliphatic, alicyclic, heteroaliphatic, heterocyclic, aromatic, heteroaromatic, aryl, and heteroaryl.

34. The method of claim 32 or 33, wherein converting the compound with an aglain core structure into a rocaglamide derivative comprises an α-ketol (acyloin) rearrangement.

35. The method of claim 34, wherein the α-ketol (acyloin) rearrangement comprises a base-mediated reaction.

36. The method of claim 19 further comprising a step of converting the compound with an aglain core structure into a rocaglamide derivative (VIII) with the following chemical structure:

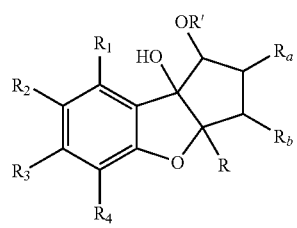

(VIII)

wherein $R_1$, $R_2$, $R_3$, $R_4$, R, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —C(=O)$R_x$, —$CO_2(R_x)$, —C(=O)N$(R_x)_2$, —OC(=O)N$(R_x)_2$, —OC(=O)$R_x$, —$OCO_2R_x$, —S(O)$R_x$, —$S(O)_2R_x$, —$NR_x$(CO)$R_x$, —N$(R_x)CO_2R_x$, —N$(R_x)$C(=O)N$(R_x)_2$, —N$(R_x)S(O)_2R_x$, and —$S(O)_2N(R_x)_2$,
    wherein each occurrence of $R_x$ is independently selected from the group consisting of hydrogen, aliphatic, alicyclic, heteroaliphatic, heterocyclic, aromatic, heteroaromatic, aryl, and heteroaryl; and
wherein R' is selected from the group consisting of hydrogen, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, a protecting group, —$CH_2OH$, —$CH_2CH_2OH$, —$CH_2SO_2CH_3$, —C(=O)$R_x$, —$CO_2(R_x)$, —C(=O)N$(R_x)_2$, —S(O)$R_x$, —$NR_x$(CO)$R_x$, —N$(R_x)CO_2R_x$, —N$(R_x)$C(=O)N$(R_x)_2$, and —N$(R_x)S(O)_2R_x$,
    wherein each occurrence of $R_x$ is independently selected from the group consisting of hydrogen, aliphatic, alicyclic, heteroaliphatic, heterocyclic, aromatic, heteroaromatic, aryl, and heteroaryl.

37. The method of claim 20 further comprising a step of converting the compound with an aglain core structure into a rocaglamide derivative (VIII') with the following chemical structure:

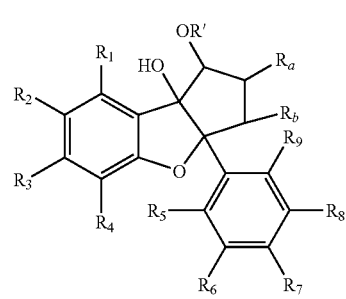

(VIII')

wherein $R_1$, $R_2$, $R_3$, $R_4$, $R_5$, $R_6$, $R_7$, $R_8$, $R_9$, $R_a$ and $R_b$ are identical or different and selected from the group consisting of hydrogen, halogen, hydroxy, alkoxy, aryloxy, heteroalkoxy, heteroaryloxy, thioalkyl, thioaryl, acyl, aliphatic, alicyclic, heteroaliphatic, heterocyclic, aromatic, heteroaromatic, aryl, heteroaryl, alkylamino, amino alkyl, arylamino, amino aryl, a protecting group, —$NO_2$, —CN, —$CF_3$, —$CH_2CF_3$, —$CHCl_2$, —$CH_2OH$, —$CH_2CH_2OH$, —$CH_2SO_2CH_3$, —C(=O)$R_x$, —$CO_2(R_x)$, —C(=O)N$(R_x)_2$, —OC(=O)N$(R_x)_2$, —OC(=O)$R_x$, —$OCO_2R_x$, —S(O)$R_x$, —$S(O)_2R_x$, —$NR_x$(CO)$R_x$, —N$(R_x)CO_2R_x$, —N$(R_x)$C(=O)N$(R_x)_2$, —N$(R_x)S(O)_2R_x$, and —$S(O)_2N(R_x)_2$,
    wherein each occurrence of $R_x$ is independently selected from the group consisting of hydrogen, aliphatic, alicyclic, heteroaliphatic, heterocyclic, aromatic, heteroaromatic, aryl, and heteroaryl; and
wherein R' is selected from the group consisting of hydrogen, alkoxy, aryloxy, heteroalkoxy, heteroaryloxy, acyl, aliphatic, alicyclic, heteroaliphatic, heterocyclic, aromatic, heteroaromatic, aryl, heteroaryl, alkylamino, amino alkyl, arylamino, amino aryl, a protecting group, —$CH_2OH$, —$CH_2CH_2OH$, —$CH_2SO_2CH_3$, —C(=O)$R_x$, —$CO_2(R_x)$, —C(=O)N$(R_x)_2$, —S(O)$R_x$, —$NR_x$(CO)$R_x$, —N$(R_x)CO_2R_x$, —N$(R_x)$C(=O)N$(R_x)_2$, and —N$(R_x)S(O)_2R_x$,
    wherein each occurrence of $R_x$ is independently selected from the group consisting of hydrogen, aliphatic, alicyclic, heteroaliphatic, heterocyclic, aromatic, heteroaromatic, aryl, and heteroaryl.

38. The method of claim 36 or 37, wherein converting the compound with an aglain core structure into a rocaglamide derivative comprises an α-ketol (acyloin) rearrangement and a hydroxyl-directed reduction.

39. The method of claim 38, wherein the α-ketol (acyloin) rearrangement comprises a base-mediated reaction.

40. The method of claim 36 or 37, wherein said method produces a mixture of endo and exo isomers of the rocaglamide derivative such that the mixture comprises more endo isomer than exo isomer.

* * * * *